US012102620B2

(12) United States Patent
Flynn et al.

(10) Patent No.: US 12,102,620 B2
(45) Date of Patent: Oct. 1, 2024

(54) COMBINATION THERAPY FOR THE TREATMENT OF MASTOCYTOSIS

(71) Applicant: Deciphera Pharmaceuticals, LLC, Waltham, MA (US)

(72) Inventors: Daniel L. Flynn, Waltham, MA (US); Bryan D. Smith, Waltham, MA (US); Anu Gupta, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 802 days.

(21) Appl. No.: 16/943,871

(22) Filed: Jul. 30, 2020

(65) Prior Publication Data

US 2020/0352920 A1 Nov. 12, 2020

Related U.S. Application Data

(63) Continuation of application No. PCT/US2019/016161, filed on Jan. 31, 2019.

(60) Provisional application No. 62/624,453, filed on Jan. 31, 2018.

(51) Int. Cl.
*A61K 31/4375* (2006.01)
*A61K 31/4184* (2006.01)
*A61K 31/4439* (2006.01)
*A61K 31/4523* (2006.01)
*A61K 31/506* (2006.01)
*A61K 31/519* (2006.01)
*A61K 45/06* (2006.01)
*A61P 43/00* (2006.01)

(52) U.S. Cl.
CPC ...... *A61K 31/4375* (2013.01); *A61K 31/4184* (2013.01); *A61K 31/4439* (2013.01); *A61K 31/4523* (2013.01); *A61K 31/506* (2013.01); *A61K 31/519* (2013.01); *A61K 45/06* (2013.01); *A61P 43/00* (2018.01)

(58) Field of Classification Search
CPC .................................................. A61K 31/4375
See application file for complete search history.

(56) References Cited

U.S. PATENT DOCUMENTS

| | | |
|---|---|---|
| 3,528,980 A | 9/1970 | Islip |
| 3,818,024 A | 6/1974 | Krenzer |
| 3,939,122 A | 2/1976 | Merten et al. |
| 3,949,002 A | 4/1976 | Feasey et al. |
| 4,093,624 A | 6/1978 | Revankar et al. |
| 4,296,237 A | 10/1981 | Cragoe, Jr. et al. |
| 4,366,189 A | 12/1982 | Burdeska et al. |
| 4,432,992 A | 2/1984 | Craqoe, Jr. et al. |
| 4,525,450 A | 6/1985 | Toh et al. |
| 4,816,454 A | 3/1989 | Zoller et al. |
| 5,103,014 A | 4/1992 | Musser et al. |
| 5,162,360 A | 11/1992 | Creswell et al. |
| 5,189,045 A | 2/1993 | Peglion et al. |
| 5,319,099 A | 6/1994 | Kamata et al. |
| 5,494,925 A | 2/1996 | Court et al. |
| 5,514,691 A | 5/1996 | Chan et al. |
| 5,614,532 A | 3/1997 | Carling et al. |
| 5,621,010 A | 4/1997 | Sueda |
| 5,658,924 A | 8/1997 | Matsuura et al. |
| 5,721,231 A | 2/1998 | Moriwaki et al. |
| 5,811,456 A | 9/1998 | Seman et al. |
| 6,020,357 A | 2/2000 | Pinto et al. |
| 6,028,085 A | 2/2000 | Bromidge |
| 6,080,763 A | 6/2000 | Regan et al. |
| 6,123,964 A | 9/2000 | Asgharnejad et al. |
| 6,147,088 A | 11/2000 | Goulet et al. |
| 6,197,599 B1 | 3/2001 | Chin et al. |
| 6,235,786 B1 | 5/2001 | Dai et al. |
| 6,294,573 B1 | 9/2001 | Curtin et al. |
| 6,319,921 B1 | 11/2001 | Cirillo et al. |
| 6,410,254 B1 | 6/2002 | Finer et al. |
| 6,500,628 B1 | 12/2002 | Robison |
| 6,525,046 B1 | 2/2003 | Cirillo et al. |
| 6,645,990 B2 | 11/2003 | Askew et al. |
| 6,763,607 B2 | 7/2004 | Beyerinck et al. |
| 6,916,924 B2 | 7/2005 | Tan et al. |
| 6,973,741 B2 | 12/2005 | Beyerinck et al. |
| 7,071,199 B1 | 7/2006 | Hirst et al. |
| 7,135,550 B2 | 11/2006 | Come et al. |
| 7,144,911 B2 | 12/2006 | Flynn et al. |
| 7,202,257 B2 | 4/2007 | Flynn et al. |
| 7,211,575 B2 | 5/2007 | Moss et al. |

(Continued)

FOREIGN PATENT DOCUMENTS

CN 101528744 A 9/2009
CN 101553232 A 10/2009

(Continued)

OTHER PUBLICATIONS

"A Safety, Tolerability and PK Study of DCC-2618 in Patients With Advanced Malignancies," ClinicalTrials.gov, Jan. 12, 2018, pp. 1-11. Retrieved from the Internet: URL: <https://clinicaltrials.gov/ct2/show/NC>.
"NHLBI LBC Computational Biophysics Scetion", CHARMM Documentation Index, http://www.lobos.nih.gov/Charmm/chmdoc.html, printed Mar. 4, 2005.
"Trilateral Project WM4—Comparative Studies in New Technologies: Report on Comparative Study on Protein 3—Dimensional Structure Related Claims—Annex 3: Comments of the USPTO", Vienna, Austria, Nov. 4-8, pp. 58-79 (2002).
Additions and Corrections, Journal of Medicinal Chemistry, 32(12):2583 (1989).

(Continued)

*Primary Examiner* — Yong S. Chong
(74) *Attorney, Agent, or Firm* — Goodwin Procter LLP

(57) ABSTRACT

The present disclosure relates to the use of 1-[4-bromo-5-[1-ethyl-7-(methylamino)-2-oxo-1,2-dihydro-1,6-naphthyridin-3-yl]-2-fluorophenyl]-3-phenylurea or 1-(5-(7-amino-1-ethyl-2-oxo-1,2-dihydro-1,6-naphthyridin-3-yl)-4-bromo-2-fluorophenyl)-3-phenylurea, or a pharmaceutically acceptable salt thereof, in combination with a MAPKAP pathway inhibitor such as for example a RAS, RAF, MEK, or ERK inhibitor for the treatment of mastocytosis.

12 Claims, 35 Drawing Sheets

(56) References Cited

U.S. PATENT DOCUMENTS

| | | |
|---|---|---|
| 7,279,576 B2 | 10/2007 | Flynn et al. |
| 7,342,037 B2 | 3/2008 | Flynn et al. |
| 7,531,566 B2 | 5/2009 | Flynn et al. |
| 7,666,895 B2 | 2/2010 | Flynn et al. |
| 7,737,283 B2 | 6/2010 | Flynn et al. |
| 7,790,756 B2 | 9/2010 | Flynn et al. |
| 7,897,762 B2 | 3/2011 | Flynn et al. |
| 8,143,293 B2 | 3/2012 | Flynn et al. |
| 8,163,756 B2 | 4/2012 | Flynn et al. |
| 8,188,113 B2 | 5/2012 | Flynn et al. |
| 8,278,331 B2 | 10/2012 | Flynn et al. |
| 8,343,550 B2 | 1/2013 | Beyerinck et al. |
| 8,461,179 B1 | 6/2013 | Flynn et al. |
| 8,486,951 B2 | 7/2013 | Flynn et al. |
| 8,569,319 B2 | 10/2013 | Flynn et al. |
| 8,586,565 B2 | 11/2013 | Flynn et al. |
| 8,637,672 B2 | 1/2014 | Flynn et al. |
| 8,669,289 B2 | 3/2014 | Li |
| 8,741,911 B2 | 6/2014 | Allgeier et al. |
| 8,828,443 B2 | 9/2014 | Beyerinck et al. |
| 8,921,565 B2 | 12/2014 | Flynn et al. |
| 8,940,756 B2 | 1/2015 | Flynn et al. |
| 9,012,635 B2 | 4/2015 | Flynn et al. |
| 9,133,183 B2 | 9/2015 | Flynn et al. |
| 9,181,223 B2 | 11/2015 | Kaufman et al. |
| 9,187,474 B2 | 11/2015 | Flynn et al. |
| 9,193,719 B2 | 11/2015 | Flynn et al. |
| 9,248,584 B2 | 2/2016 | Friesen et al. |
| 9,265,731 B2 | 2/2016 | Ray et al. |
| 9,309,224 B2 | 4/2016 | Flynn et al. |
| 9,334,267 B2 | 5/2016 | Flynn et al. |
| 9,339,467 B2 | 5/2016 | Beyerinck et al. |
| 9,382,228 B2 | 7/2016 | Flynn et al. |
| 9,387,202 B2 | 7/2016 | Flynn et al. |
| 9,457,019 B2 | 10/2016 | Flynn et al. |
| 9,545,407 B2 | 1/2017 | Shu et al. |
| 9,724,664 B2 | 8/2017 | Friesen et al. |
| 10,300,443 B2 | 5/2019 | Friesen et al. |
| 10,383,941 B2 | 8/2019 | Beyerinck et al. |
| 10,675,602 B2 | 6/2020 | Friesen et al. |
| 10,966,966 B2 | 4/2021 | Soto et al. |
| 11,103,507 B2 | 8/2021 | Flynn et al. |
| RE48,731 E | 9/2021 | Flynn et al. |
| 11,185,535 B2 | 11/2021 | Kaufman et al. |
| 11,266,635 B2 | 3/2022 | Soto et al. |
| 11,344,536 B1 | 5/2022 | Soto et al. |
| 11,395,818 B2 | 7/2022 | Kaufman et al. |
| 11,426,390 B2 | 8/2022 | Soto et al. |
| 11,433,056 B1 | 9/2022 | Soto et al. |
| 11,518,758 B2 | 12/2022 | Flynn et al. |
| 11,529,336 B2 | 12/2022 | Soto et al. |
| 11,530,206 B2 | 12/2022 | Flynn et al. |
| 11,534,432 B2 | 12/2022 | Soto et al. |
| 11,576,903 B2 | 2/2023 | Kaufman et al. |
| 11,576,904 B2 | 2/2023 | Soto et al. |
| 11,590,134 B2 | 2/2023 | Flynn et al. |
| 11,612,591 B2 | 3/2023 | Kaufman et al. |
| 11,679,110 B2 | 6/2023 | Flynn et al. |
| 11,779,572 B1 | 10/2023 | Wang et al. |
| 11,793,795 B2 | 10/2023 | Kaufman et al. |
| 11,801,237 B2 | 10/2023 | Kaufman et al. |
| 11,813,251 B2 | 11/2023 | Soto et al. |
| 2002/0058678 A1 | 5/2002 | Cirillo et al. |
| 2002/0077486 A1 | 6/2002 | Scarborough et al. |
| 2002/0165394 A1 | 11/2002 | Dumas et al. |
| 2002/0193405 A1 | 12/2002 | Askew |
| 2003/0060455 A1 | 3/2003 | Moss et al. |
| 2003/0105139 A1 | 6/2003 | Gaster et al. |
| 2003/0144278 A1 | 7/2003 | Riedl et al. |
| 2003/0181442 A1 | 9/2003 | Riedl et al. |
| 2003/0207870 A1 | 11/2003 | Dumas et al. |
| 2003/0216396 A1 | 11/2003 | Dumas et al. |
| 2003/0232865 A1 | 12/2003 | Cirillo et al. |
| 2004/0043388 A1 | 3/2004 | Come et al. |
| 2004/0067938 A1 | 4/2004 | Zhang et al. |
| 2004/0102636 A1 | 5/2004 | Miller et al. |
| 2004/0157827 A1 | 8/2004 | Pevarello et al. |
| 2004/0167224 A1 | 8/2004 | Ozaki et al. |
| 2004/0171075 A1 | 9/2004 | Flynn et al. |
| 2004/0180906 A1 | 9/2004 | Flynn et al. |
| 2004/0229937 A1 | 11/2004 | Dumas et al. |
| 2005/0014753 A1 | 1/2005 | Ding et al. |
| 2005/0148605 A1 | 7/2005 | Grotzfeld et al. |
| 2005/0165024 A1 | 7/2005 | Milanov et al. |
| 2005/0165031 A1 | 7/2005 | Grotzfeld et al. |
| 2005/0165074 A1 | 7/2005 | Grotzfeld et al. |
| 2005/0171171 A1 | 8/2005 | Mehta et al. |
| 2005/0171172 A1 | 8/2005 | Lai et al. |
| 2005/0192314 A1 | 9/2005 | Mehta et al. |
| 2005/0197371 A1 | 9/2005 | Milanov et al. |
| 2005/0256174 A1 | 11/2005 | Wood et al. |
| 2005/0261315 A1 | 11/2005 | Mehta et al. |
| 2005/0267182 A1 | 12/2005 | Milanov et al. |
| 2005/0288286 A1 | 12/2005 | Flynn et al. |
| 2006/0229337 A1 | 10/2006 | Brittelli et al. |
| 2006/0247186 A1 | 11/2006 | Carter et al. |
| 2007/0037794 A1 | 2/2007 | Ungashe et al. |
| 2007/0078121 A1 | 4/2007 | Flynn et al. |
| 2007/0155764 A1 | 7/2007 | Lang et al. |
| 2007/0179130 A1 | 8/2007 | Bannen |
| 2007/0191336 A1 | 8/2007 | Flynn et al. |
| 2007/0244120 A1 | 10/2007 | Dumas et al. |
| 2007/0293685 A1 | 12/2007 | Fritch et al. |
| 2008/0009527 A1 | 1/2008 | Dumas et al. |
| 2008/0045531 A1 | 2/2008 | Flynn et al. |
| 2008/0045706 A1 | 2/2008 | Flynn et al. |
| 2008/0064717 A1 | 3/2008 | Iyengar et al. |
| 2008/0090856 A1 | 4/2008 | Flynn et al. |
| 2008/0113967 A1 | 5/2008 | Flynn et al. |
| 2008/0114006 A1 | 5/2008 | Flynn et al. |
| 2008/0132506 A1 | 6/2008 | Flynn et al. |
| 2008/0176846 A1 | 7/2008 | Chianelli et al. |
| 2008/0187978 A1 | 8/2008 | Flynn et al. |
| 2008/0194836 A1 | 8/2008 | Gharbaoui et al. |
| 2008/0200530 A1 | 8/2008 | Unett et al. |
| 2008/0207699 A1 | 8/2008 | Hoelzemann et al. |
| 2008/0214545 A1 | 9/2008 | Lee et al. |
| 2008/0220497 A1 | 9/2008 | Flynn et al. |
| 2008/0221192 A1 | 9/2008 | Wan et al. |
| 2008/0248487 A1 | 10/2008 | Flynn et al. |
| 2008/0248548 A1 | 10/2008 | Flynn et al. |
| 2008/0300281 A1 | 12/2008 | Dumas et al. |
| 2009/0069310 A1 | 3/2009 | Flynn et al. |
| 2009/0075986 A1 | 3/2009 | Flynn et al. |
| 2009/0093526 A1 | 4/2009 | Miller et al. |
| 2009/0099190 A1 | 4/2009 | Flynn et al. |
| 2009/0105230 A1 | 4/2009 | Flynn et al. |
| 2009/0124633 A1 | 5/2009 | Jonczyk et al. |
| 2009/0137021 A1 | 5/2009 | Flynn et al. |
| 2009/0192307 A1 | 7/2009 | Michelotti et al. |
| 2009/0215799 A1 | 8/2009 | Stieber et al. |
| 2009/0281089 A1 | 11/2009 | Gunzner et al. |
| 2009/0312349 A1 | 12/2009 | Flynn et al. |
| 2009/0325945 A1 | 12/2009 | Niculescu-Duvaz et al. |
| 2010/0075971 A1 | 3/2010 | Dumas et al. |
| 2010/0160292 A1 | 6/2010 | Whitney et al. |
| 2010/0209420 A1 | 8/2010 | Lamb et al. |
| 2010/0286215 A1 | 11/2010 | Pelcman et al. |
| 2010/0298290 A1 | 11/2010 | Anand et al. |
| 2011/0077240 A1 | 3/2011 | Mannion et al. |
| 2011/0092461 A1 | 4/2011 | Gunzner et al. |
| 2011/0098293 A1 | 4/2011 | Mannion et al. |
| 2011/0112193 A1 | 5/2011 | Nilsson et al. |
| 2011/0124640 A1 | 5/2011 | Liu et al. |
| 2011/0136760 A1 | 6/2011 | Flynn et al. |
| 2011/0136809 A1 | 6/2011 | Lee et al. |
| 2011/0183997 A1 | 7/2011 | Chianelli et al. |
| 2011/0195110 A1 | 8/2011 | Smith et al. |
| 2011/0237563 A1 | 9/2011 | Costantini |
| 2012/0094980 A1 | 4/2012 | Gunzner et al. |
| 2012/0114605 A1 | 5/2012 | Li |
| 2012/0214808 A1 | 8/2012 | Bloxham et al. |
| 2012/0225057 A1 | 9/2012 | Flynn et al. |
| 2012/0270878 A1 | 10/2012 | Miller et al. |

(56) References Cited

U.S. PATENT DOCUMENTS

| | | |
|---|---|---|
| 2012/0289540 A1 | 11/2012 | Flynn et al. |
| 2013/0071403 A1 | 3/2013 | Rolland et al. |
| 2013/0225581 A1 | 8/2013 | Furuta et al. |
| 2013/0296326 A1 | 11/2013 | Pollock |
| 2014/0088075 A1 | 3/2014 | Flynn et al. |
| 2014/0107100 A1 | 4/2014 | Rice et al. |
| 2014/0147415 A1 | 5/2014 | Moussy et al. |
| 2014/0179632 A1 | 6/2014 | Mannion et al. |
| 2014/0296248 A1 | 10/2014 | Bernards et al. |
| 2014/0296267 A1 | 10/2014 | Fry et al. |
| 2014/0336210 A1 | 11/2014 | Christopher et al. |
| 2015/0031648 A1 | 1/2015 | Le Tiran et al. |
| 2015/0073141 A1 | 3/2015 | Teegarden et al. |
| 2015/0105550 A1 | 4/2015 | Gunzner et al. |
| 2015/0111879 A1 | 4/2015 | Gunzner et al. |
| 2015/0133462 A1 | 5/2015 | Singh et al. |
| 2015/0218652 A1 | 8/2015 | Doebele et al. |
| 2015/0225369 A1 | 8/2015 | Wucherer-Plietker et al. |
| 2015/0246033 A1 | 9/2015 | Flynn et al. |
| 2015/0275306 A1 | 10/2015 | Bernards et al. |
| 2015/0320759 A1 | 11/2015 | Flynn et al. |
| 2016/0009709 A1 | 1/2016 | Cheve et al. |
| 2016/0045532 A1 | 2/2016 | Roberts et al. |
| 2016/0152569 A1 | 6/2016 | Gunzner-Toste et al. |
| 2016/0166679 A1 | 6/2016 | Low et al. |
| 2016/0222012 A1 | 8/2016 | Ruan |
| 2016/0243150 A1 | 8/2016 | Wood et al. |
| 2016/0289663 A1 | 10/2016 | Kiyokawa et al. |
| 2016/0374990 A1 | 12/2016 | Teegarden et al. |
| 2017/0015627 A1 | 1/2017 | Gunzner-Toste et al. |
| 2017/0121321 A1 | 5/2017 | Crews et al. |
| 2017/0174750 A1 | 6/2017 | Lim et al. |
| 2017/0349880 A1 | 12/2017 | Doucey et al. |
| 2017/0360791 A1 | 12/2017 | Joshi-Hangal et al. |
| 2018/0000771 A1 | 1/2018 | Inoue et al. |
| 2018/0071302 A1 | 3/2018 | Abella et al. |
| 2018/0071303 A1 | 3/2018 | Abella et al. |
| 2019/0091217 A1 | 3/2019 | Flynn et al. |
| 2020/0129489 A1 | 4/2020 | Flynn et al. |
| 2020/0253973 A1 | 8/2020 | Flynn et al. |
| 2020/0352920 A1 | 11/2020 | Flynn et al. |
| 2020/0354346 A1 | 11/2020 | Flynn et al. |
| 2020/0354352 A1 | 11/2020 | Flynn et al. |
| 2021/0015801 A1 | 1/2021 | Flynn et al. |

FOREIGN PATENT DOCUMENTS

| | | | |
|---|---|---|---|
| CN | 102731385 A | 10/2012 | |
| CN | 105461699 A | 4/2016 | |
| CN | 106573002 A | 4/2017 | |
| CN | 106822128 A | 6/2017 | |
| CN | 108379591 A | 8/2018 | |
| CN | 111328283 A | 6/2020 | |
| CN | 114902895 A | 8/2022 | |
| DE | 1115350 B | 10/1961 | |
| DE | 4343831 A1 | 6/1995 | |
| EP | 0021228 A1 | 1/1981 | |
| EP | 0025232 A1 | 3/1981 | |
| EP | 0154190 A1 | 9/1985 | |
| EP | 0661276 A1 | 7/1995 | |
| EP | 0692483 A4 | 11/1995 | |
| EP | 0739884 A2 | 10/1996 | |
| EP | 0867435 A1 | 9/1998 | |
| EP | 0927555 A1 | 7/1999 | |
| EP | 928790 A1 | 7/1999 | |
| EP | 0956855 A1 | 11/1999 | |
| EP | 1281399 A2 | 2/2003 | |
| EP | 2858646 A1 | 4/2015 | |
| EP | 2827900 B1 | 3/2018 | |
| FR | 2337554 A1 | 8/1977 | |
| FR | 2396549 A2 | 2/1979 | |
| GB | 971307 A | 9/1964 | |
| GB | 1410279 A | 10/1975 | |
| GB | 2220206 A | 1/1990 | |
| JP | 59-177557 A | 8/1984 | |
| JP | 9221476 | 8/1997 | |
| JP | 2000275886 A | 10/2000 | |
| JP | 20012687 A | 1/2001 | |
| JP | 2010-506948 A | 3/2010 | |
| JP | 2015-520186 A | 7/2015 | |
| JP | 2015-532296 A | 11/2015 | |
| JP | 59-15247 B2 | 5/2016 | |
| KR | 20130065368 A | 6/2013 | |
| WO | 1991/19708 A1 | 12/1991 | |
| WO | 1992/08693 A1 | 5/1992 | |
| WO | 1994/18176 A1 | 8/1994 | |
| WO | 1994/21617 | 9/1994 | |
| WO | 1994/24095 A1 | 10/1994 | |
| WO | 1995/006044 A1 | 3/1995 | |
| WO | 1995/15954 A1 | 6/1995 | |
| WO | 1995/29902 A1 | 11/1995 | |
| WO | 1995/34540 A1 | 12/1995 | |
| WO | 1996/16046 A2 | 5/1996 | |
| WO | 1996/19477 A1 | 6/1996 | |
| WO | 1996/023783 A1 | 8/1996 | |
| WO | 1997/34900 A1 | 9/1997 | |
| WO | 1997/037989 A2 | 10/1997 | |
| WO | 1997/40028 A1 | 10/1997 | |
| WO | 1997/045400 A1 | 12/1997 | |
| WO | 1998/22103 A1 | 5/1998 | |
| WO | 1998/52558 A1 | 11/1998 | |
| WO | 1999/15164 A1 | 4/1999 | |
| WO | 1999/23091 A1 | 5/1999 | |
| WO | 1999/23093 A1 | 5/1999 | |
| WO | 1999/32106 | 7/1999 | |
| WO | 1999/32110 A1 | 7/1999 | |
| WO | 1999/32111 | 7/1999 | |
| WO | 1999/32455 | 7/1999 | |
| WO | 1999/37622 A1 | 7/1999 | |
| WO | 1999/59959 A1 | 11/1999 | |
| WO | 2000/06550 A1 | 2/2000 | |
| WO | 2000/07980 A1 | 2/2000 | |
| WO | 2000/18738 A1 | 4/2000 | |
| WO | 2000/21927 A2 | 4/2000 | |
| WO | 2000/41698 A1 | 7/2000 | |
| WO | 2000/042012 A1 | 7/2000 | |
| WO | 2000/43384 A1 | 7/2000 | |
| WO | 2000/55139 A2 | 9/2000 | |
| WO | 2000/59506 A1 | 10/2000 | |
| WO | 2000/071515 A2 | 11/2000 | |
| WO | 2001/12621 A1 | 2/2001 | |
| WO | 2001/14372 A2 | 3/2001 | |
| WO | 2001/74771 A1 | 10/2001 | |
| WO | 2001/96298 A2 | 12/2001 | |
| WO | 2002/00647 A1 | 1/2002 | |
| WO | 2002/014291 A1 | 2/2002 | |
| WO | 2002/014311 A2 | 2/2002 | |
| WO | 2002/026712 A2 | 4/2002 | |
| WO | 2002/028835 A1 | 4/2002 | |
| WO | 2002/034727 A2 | 5/2002 | |
| WO | 2002/060869 A2 | 8/2002 | |
| WO | 2002/060876 A1 | 8/2002 | |
| WO | 2002/062763 A2 | 8/2002 | |
| WO | 2002/070662 A2 | 9/2002 | |
| WO | 2003/005999 A2 | 1/2003 | |
| WO | WO-03002114 A2 * | 1/2003 | ............ A61K 31/00 |
| WO | 2003/047579 A1 | 6/2003 | |
| WO | 2003/053368 A2 | 7/2003 | |
| WO | 2003/059373 A2 | 7/2003 | |
| WO | 2003/068223 A1 | 8/2003 | |
| WO | 2003/068229 A1 | 8/2003 | |
| WO | 2003/072577 A2 | 9/2003 | |
| WO | 2003/084539 A2 | 10/2003 | |
| WO | 2004/004720 A1 | 1/2004 | |
| WO | 2004/056783 A1 | 7/2004 | |
| WO | 2004/060305 A2 | 7/2004 | |
| WO | 2004/060306 A2 | 7/2004 | |
| WO | 2004/061084 A2 | 7/2004 | |
| WO | 2004/078128 A2 | 9/2004 | |
| WO | 2004/078746 A2 | 9/2004 | |
| WO | 2004/113352 A1 | 12/2004 | |
| WO | 2005/002673 A1 | 1/2005 | |
| WO | 2005/012254 A1 | 2/2005 | |
| WO | 2005/024755 A2 | 3/2005 | |

(56) References Cited

FOREIGN PATENT DOCUMENTS

| | | |
|---|---|---|
| WO | 2005/034869 A2 | 4/2005 |
| WO | 2005/048948 A2 | 6/2005 |
| WO | 2005/103011 A1 | 11/2005 |
| WO | 2005/110994 A2 | 11/2005 |
| WO | 2006/014290 A2 | 2/2006 |
| WO | 2006/014325 A2 | 2/2006 |
| WO | 2006/018662 A2 | 2/2006 |
| WO | 2006/028958 A2 | 3/2006 |
| WO | 2006/039718 A2 | 4/2006 |
| WO | 2006/040056 A1 | 4/2006 |
| WO | 2006/046552 A1 | 5/2006 |
| WO | 2006/052936 A2 | 5/2006 |
| WO | 2006/062984 A2 | 6/2006 |
| WO | 2006/071940 A2 | 7/2006 |
| WO | 2006/072589 A2 | 7/2006 |
| WO | 2006/078610 A1 | 7/2006 |
| WO | 2006/081034 A2 | 8/2006 |
| WO | 2006/081335 A2 | 8/2006 |
| WO | 2006/099075 A2 | 9/2006 |
| WO | 2006/105844 A1 | 10/2006 |
| WO | 2007/008917 A2 | 1/2007 |
| WO | 2007/042321 A2 | 4/2007 |
| WO | 2007/064872 A2 | 6/2007 |
| WO | 2007/076473 A2 | 7/2007 |
| WO | 2007/081690 A2 | 7/2007 |
| WO | 2007/115670 A1 | 10/2007 |
| WO | 2007/125330 A1 | 11/2007 |
| WO | 2007/136465 A2 | 11/2007 |
| WO | 2007/137107 A2 | 11/2007 |
| WO | 2008/033858 A2 | 3/2008 |
| WO | 2008/033999 A2 | 3/2008 |
| WO | 2008/034008 A2 | 3/2008 |
| WO | 2008/046003 A2 | 4/2008 |
| WO | 2008/051757 A1 | 5/2008 |
| WO | 2008/131227 A1 | 10/2008 |
| WO | 2008/131253 A1 | 10/2008 |
| WO | 2008/140895 A1 | 11/2008 |
| WO | 2009/030887 A2 | 3/2009 |
| WO | 2009/076454 A2 | 6/2009 |
| WO | 2009/109035 A1 | 9/2009 |
| WO | 2009/126863 A2 | 10/2009 |
| WO | 2009/127822 A2 | 10/2009 |
| WO | 2009/138758 A2 | 11/2009 |
| WO | 2010/011837 A1 | 1/2010 |
| WO | 2010/051373 A1 | 5/2010 |
| WO | 2010/124283 A2 | 10/2010 |
| WO | 2010/135524 A1 | 11/2010 |
| WO | 2011/067306 A1 | 6/2011 |
| WO | 2011/123788 A1 | 10/2011 |
| WO | 2011/137342 A1 | 11/2011 |
| WO | 2011/139891 A1 | 11/2011 |
| WO | 2011/150198 A1 | 12/2011 |
| WO | 2012/008563 A1 | 1/2012 |
| WO | 2012/019015 A2 | 2/2012 |
| WO | 2012/035131 A1 | 3/2012 |
| WO | 2012/071519 A1 | 5/2012 |
| WO | 2012/097021 A1 | 7/2012 |
| WO | 2012/138783 A2 | 10/2012 |
| WO | 2013/036232 A2 | 3/2013 |
| WO | 2013/043569 A1 | 3/2013 |
| WO | 2013/066440 A1 | 5/2013 |
| WO | 2013/078295 A2 | 5/2013 |
| WO | 2013/134243 A1 | 9/2013 |
| WO | 2013/134252 A1 | 9/2013 |
| WO | 2013/134298 A1 | 9/2013 |
| WO | 2013/177420 A2 | 11/2013 |
| WO | 2013/184119 A1 | 12/2013 |
| WO | 2014/015056 A1 | 1/2014 |
| WO | 2014/032755 A2 | 3/2014 |
| WO | 2014/036387 A2 | 3/2014 |
| WO | 2014/037480 A1 | 3/2014 |
| WO | 2014/040242 A1 | 3/2014 |
| WO | 2014/040549 A1 | 3/2014 |
| WO | 2014/058317 A1 | 4/2014 |
| WO | 2014/102376 A1 | 7/2014 |
| WO | 2014/102377 A1 | 7/2014 |
| WO | 2014/139458 A1 | 9/2014 |
| WO | 2014/145004 A1 | 9/2014 |
| WO | 2014/145015 A2 | 9/2014 |
| WO | 2014/145023 A1 | 9/2014 |
| WO | 2014/145025 A2 | 9/2014 |
| WO | 2014/145028 A2 | 9/2014 |
| WO | 2014/145029 A2 | 9/2014 |
| WO | 2014/160183 A1 | 10/2014 |
| WO | 2014/182643 A2 | 11/2014 |
| WO | 2015/011399 A1 | 1/2015 |
| WO | WO-2015/051252 A1 | 4/2015 |
| WO | 2015/069217 A1 | 5/2015 |
| WO | 2015/069266 A1 | 5/2015 |
| WO | 2015/076213 A1 | 5/2015 |
| WO | 2015/092423 A1 | 6/2015 |
| WO | 2015/106292 A1 | 7/2015 |
| WO | 2015/106294 A1 | 7/2015 |
| WO | 2015/148620 A2 | 10/2015 |
| WO | 2015/184443 A1 | 12/2015 |
| WO | WO-2016/025621 A1 | 2/2016 |
| WO | 2016/061228 A1 | 4/2016 |
| WO | 2016/061231 A1 | 4/2016 |
| WO | 2016/096903 A1 | 6/2016 |
| WO | 2016/103223 A1 | 6/2016 |
| WO | 2016/114322 A1 | 7/2016 |
| WO | 2016/135046 A1 | 9/2016 |
| WO | 2016/154524 A1 | 9/2016 |
| WO | 2016/196141 A1 | 12/2016 |
| WO | 2017/013160 A1 | 1/2017 |
| WO | 2017/042944 A1 | 3/2017 |
| WO | WO-2017033113 A1 * | 3/2017 ......... A61K 31/4184 |
| WO | 2017/079267 A1 | 5/2017 |
| WO | 2017/117182 A1 | 7/2017 |
| WO | 2017/146794 A1 | 8/2017 |
| WO | 2017/146795 A1 | 8/2017 |
| WO | 2017/214514 A1 | 12/2017 |
| WO | 2018/005737 A1 | 1/2018 |
| WO | 2018/052053 A1 | 3/2018 |
| WO | 2018/053189 A2 | 3/2018 |
| WO | 2018/106595 A1 | 6/2018 |
| WO | 2018/195450 A1 | 10/2018 |
| WO | 2018/222173 A1 | 12/2018 |
| WO | 2018/222644 A1 | 12/2018 |
| WO | WO-2019/084462 A1 | 5/2019 |
| WO | WO-2019/152711 A1 | 8/2019 |
| WO | WO-2020/185812 A1 | 9/2020 |
| WO | WO-2021/030405 A1 | 2/2021 |

OTHER PUBLICATIONS

Aklilu, et al., "Increased PTHRP Production by a Tyrosine Kinase Oncogene, Tpr-Met: Rose of the Ras Signaling Pathway", The American Physiological Society, pp. E277-E283 (1996).

Albericio, et al., "Synthesis of a Sulfaydantion Library", J. Comb. Chem., 3:290-300 (2001).

Almerico, et al., "On the Preparation of 1-aryl-2-heteroaryl- and 2-aryl-1-heteroaryl-pyrroles as Useful Building Blocks for Biologically Interesting Heterocycles", ARKIVOC, Rudy Abramovitch Issue, pp. 129-142 (2001).

Antonescu, et al., "Acquired Resistance to Imatinib in Gastrointestinal Stromal Tumor Occurs Through Secondary Gene Mutation," Clinical cancer research : an official journal of the American Association for Cancer Research, 11(11):4182-4190 (2005).

Anzai, et al., "Alkyl- and Arylthiation of Uracil and Indole", J. Heterocyclic Chem., 16:567-569 (1979).

Askew, et al., "Molecular Recognition with Convergent Functional Groups: 6. Synthetic and Structural Studies with a Model Receptor for Nucleic Acid Components", J. Am. Chem., 111:1082-1090 (1989).

Avruch, J. et al., "Ras Activation of the Raf Kinase: Tyrosine Kinase Recmitment of the MAP Kinase Cascade," Recent Prag Harm. Res. (2001) 56: 127-155.

Bai et al., "Targeting the KITactivating switch control pocket: a novel mechanism to inhibit neoplastic mast cell proliferation and mast cell activation," Leukemia (2013), vol. 27, pp. 278-285.

(56) References Cited

OTHER PUBLICATIONS

Bais, et al., "Inhibition of Endogenous Wxalate Production: Biochemical Consideration of the Roles of Glycollate Oxidase and Lactate Dehydrogenase", Clinical Science, 76:303-309 (1989).
Baker, et al., "Irreversible Enzyme Inhibitors. 188. Inhibition of Mammalian Thymidine Phosphorylase", Journal of Medicinal Chemistry, 14:612-616 (1971).
Barker, et al., "Characterization of pp60c-src Tyrosine Kinase Activities Using a Continuous Assay: Autoactivation of the Enzyme is an Intermolecular Autophosphorylation Process", Biochemist, 35:14843-14851 (1995).
Barvian, et al., "Pyrido[2,3-d]pyrimidin-7-one Inhibitors of Cyclin-Dependent Kinases," J Med Chem. (2000) 43:4606-4616.
Bausch, et al., "Proton-Transfer Chemistry of Urazoles and Related Imides, and Diacyl H drazides", J. Org. Chem., 56:5643-5651 (1991).
Beghini, et al., "C-kit mutations in core binding factor leukemias," Blood Journal, 95(2):726-727 (2000).
Benvenuti, et al., "Crystallization of Soluble Proteins in Vapor Diffusion for X-Ray Crystallography", Nature Protocols, 2(7):1633-1651 (2007).
Blay, et al., "Ripretinib in patients with advanced gastrointestinal stromal tumours (INVICTUS): a double-blind, randomised, placebo-controlled, phase 3 trial", Lancet Oncology, 21:923-934 (2020).
Bolton, et al., "Chapter 17. Ras Oncogene Directed Approaches in Cancer Chemotherapy," Ann. Rep. Med. Chem. (1994) 29: 165-174.
Bosca, et al., "Circular Dichroism Analysis of Ligand-Induced Conformational Changes in Protein Kinase C", Biochem J., 290:827-832 (1993).
Boschelli, et al., "4-Anilino-3-quinolinecarbonitriles: An Emerging Class of Kinase Inhibitors", Current Topics in Medicinal Chemist, 2:1051-1063 (2002).
Bourdon NEC, et al., "Synthesis and Pharmacological Evaluation of New Pyrazolidine-3,5-diones as AT 1 Angiotensin II Receptor Antagonists", J. Med. Chem., 43:2685-2697 (2000).
Boyer, "Small Molecule Inhibitors of KDR (VEGFR-2) Kinase: An Overview of Structure Activit Relationships", Current Topics in Medicinal Chemist , 2:973-1000 (2002).
Brady, et al., "Fast Prediction and Visualization of Protein Binding Pockets with PASS". Journal of Computer-Aided Molecular Desi n, 14:383-401 (2000).
Branford, et al., "High Frequency of Point Mutations Clustered Within the Adenosine Triphosphate-binding Region of BCR/ABL in Patients With Chronic Myeloid Leukemia or Ph-positive Acute Lymphoblastic Leukemia Who Develop Imatinib (ST1571)resistance," Blood (2002) vol. 99, pp. 3472-3475.
Brasher, et al., "C-Abul has High Intrinsic Tyrosine Kinase Activity that is Stimulated by Mutation of the Src Homology 3 Domain and by Autophosphorylation at Two Distinct Re ulator T rosines", Journal of Biolo ical Chemistr , 275:35631-35637 (2000).
Bullock, et al., "Prospects for Kinase Activity Modulators in the Treatment of Diabetes and Diabetic Complications", Current Topics in Medicinal Chemistr , 2:915-938 (2002).
Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).
Cardillo, et al., "Su lie 1,2-difenil-3.5-dichetopirazolidine", Gazz. Chim., Ital., 9:973-985 (1966).
Carr, J. B., et al., "Isoxazolc Anthelmintics," J /'vied. Chem (1977) vol. 20, No. 7, pp. 934-939.
Chan, "Promotion of Reaction of N—H Bonds with Triarylbismuth and Cupric Acetate," Tetrahedron Letters (1996) vol. 37, No. 50, pp. 9013-9016.
Chan, et al, "New N- and O-Arylations with Phenylboronic Acids and Cupric Acetate," Tetrahedron Lett. (1998) 39:2933-2936.
Chan, et al., "Copper Promoted C—N and C—O Bond Cross-coupling With Phenyl and Pyridylboronates," Tetrahedron Letters (2003) vol. 44, pp. 3863-3865.

Chen, et al., "Biochemical Evidence for the Autophosphorylation and Transphosphorylation of Transforming Growth Factor 13 Receptor Kinases", Proc. Natl. Acad. Sci. USA, 92:1565-1569 (1995).
Cheng, et al., "Novel Solution Phase Strategy for the Synthesis of Chemical Libraries Containing Small Organic Molecules", J. Am. Chem. Soc., 118:2567-2573 (1996).
Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).
Chu, et al., "Using Affinity Capillary Electrophoresis to Determine Binding Stoichiometries of Protein-Ligand Interactions", Biochemistry, 33:10616-10621 (1994).
Cirillo, et al., "The Non-Diaryl Heterocycle Classes of p38 MAP Kinase Inhibitors", Current Topics in Medicinal Chemistry, 2:1021-1035 (2002).
Clincial trial NCT02571036—A Safety, Tolerability and PK Study of DCC-2618 in Patients With Advanced Malignancies—clinicaltrials.gov—May 25, 2017.
Clincial trial NCT02571036—A Safety, Tolerability and PK Study of DCC-2618 in Patients With Advanced Malignancies—clinicaltrials.gov—Oct. 8, 2015.
Clincial trial NCT02571036—A Safety, Tolerability and PK Study of DCC-2618 in Patients With Advanced Malignancies—clinicaltrials.gov—Sep. 17, 2018.
Clinical trial NCT03353753 Phase 3 Study of DCC-2618 vs Placebo in Advanced GIST Patients Who Have Been Treated With Prior Anticancer Therapies (invictus)—clinicaltrials.gov—Nov. 27, 2017.
Clinical trial NCT03353753 Phase 3 Study of DCC-2618 vs Placebo in Advanced GIST Patients Who Have Been Treated With Prior Anticancer Therapies (invictus)—clinicaltrials.gov—Nov. 21, 2018.
Closier, et al., "Nitrofuryl Heterocyclics. 1", Journal of Medicinal Chemistry, 13(4):638-640 (1970).
Cockerill, et al., "Small Molecule Inhibitors of the Class 1 Receptor Tyrosine Kinase Family", Current Topics in Medicinal Chemistry, 2:1001-1010 (2002).
Col Ton, et al., "Affinity Capillary Electrophoresis: A Physical-Organic Tool for Studying Interactions in Biomolecular Recognition", Electrophoresis, 19:367-382 (1998).
Corless, et al., "Biology of Gastrointestinal Stromal Tumors," Journal of Clinical Oncology, 22(18):3813-3825 (2004).
Cortes, et al., "Results of Imatinib Mesylate Therapy in Patients with Refractory or Recurrent Acute Myeloid Leukemia, High-Risk Myelodysplastic Syndrime, and Mveloproliferative Disorders", Cancer, 97(11):2760-2766 (2003).
Kwong, et al., "A General, Efficient, and Inexpensive Catalyst System for the Coupling Aryl Iodides and Thiols", Organic Letters, 4(20):3517-3520 (2002).
Laskowski, "SURFNET: A Program for Visualizing Molecular Surfaces, Cavities, and Intermolecular Interactions", Journal of Molecular Graphics, 13:323-330 (1995).
Leca, et al., "A New Practical One-Pot Access to Sulfonimidates", Organic Letters, 4(23):4093-4095 (2002).
Lefevre, et al., "Roles of Stem Cell Factor/c-Kit and Effects of Glivec®/STI571 in Human Uveal Melanoma Cell Turmorigenesis", Journal of Biological Chemistry, 279(30):31769-31779 (2004).
Lesort, et al., "Insulin Transiently Increases Tau Phosphorylation: Involvement of Glycogen Synthase Kinase-3f3 and Fyn Tyrosine Kinase", Journal of Neurochemistry, 72(2):576-584 (1999).
Leung, et al., "The Difluoromethylensulfonic Acid Groups as a Monoanionic Phosphate Surrogate for Obtaining PTP1B Inhibitors", Bioorganic & Medicinal Chemistry, 10:2309-2323 (2002).
Li, et al., "Targeting Serine/Threonine Protein Kinase B/Akt and Cell-cycle Checkpoint Kinases for Treating Cancer", Current Topics in Medicinal Chemistry, 2:939-971 (2002).
Li, et al., "The P190, {210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).

(56) References Cited

OTHER PUBLICATIONS

Lim et al., "Current research and treatment for gastrointestinal stromal tumors" World Journal of Gastroenterology (2017), 23(27), 4856-4866 Publisher: Baishideng Publishing Group Inc.
Link, et al., "Synthesis of 8-Substituted 5-Deazaflavins", J. Heterocyclic Chem, 22:841-848 (1985).
Lipinski, et al., "Experimental and Computational Approaches to Estimate Solubility and Permeability in Drug Discovery and Development Settings", Advanced Drug Delivery Reviews, 23:3-25 (1997).
Longley et al., "Somatic c-KIT activating mutation in urticaria pigmentosa and aggressive mastocytosis: establishment of clonality in a human mast cell neoplasm," Nature Genetics, 12(3):312-314 (1996).
Loren, et al., "NH-1,2,3-Triazoles from Azidomethyl Pivalate and Carbamates: Base-Labile N-Protecting Groups", SYNLETT, 18:2847-2850 (2005).
Lorenzi, et al., "Amino Acid Ester Prodrugs of 2-Bromo-5, 6-dichloro-1-([3-D-ribofuranosyl)benzimidazole Enhance Metabolic Stability In Vitro and In Vivo," The Journal of Phannaco/ogy and Experimental Therapeutics (2005) vol. 314, No. 2 pp. 883-890.
Lowinger, et al., "Design and Discovery of Small Molecules Targeting Raf-1 Kinase", Current Pharmaceutical Design, 8:2269-2278 (2002).
Ma, et al., "c-MET Mutational Analysis in Small Cell Lung Cancer: Novel Juxtamembrane Domain Mutations Regulating Cytoskeletal Functions", Cancer Research, 63:6272-6281 (2003).
Ma, et al., "c-Met: Structure, Functions and Potential for Therapeutic Inhibition", Cancer and Metastasis Reviews, 22:309-325 (2003).
Magnuson, et al, "The Raf-I serine/threonine protein kinase," Seminars in Cancer Biology. (1994) 5: 247-253.
Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).
Mamaev, et al., "Synthesis of 2,5'-Bipyrimidines from Substituted 5-Cyanopyrimidines", Khimiya Geterotsiklicheskikh Soedinenni, 24(3):371-375—(1988).
March's Advanced Organic Chemisto.::: Reactions Mechanisms and Structure Fifth Edition, Smith and March Editors, Wiley-Interscience Publication (2001).
March, et al., "Tautomerism", from March's Advanced Organic Chemisto.::, 4th Edition, WileyInterscience, pp. 69-74.
Martinez, et al., "First Non-ATP Competitive Glycogen Synthase Kinase 313 (GSK-313) Inhibitors: Thiadizolidinones (TDZD) as Potential Drugs for the Treatment of Alzheimers Disease", J. Med. Chem., 45(2002)1292-1299 (2002).
Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunoloav, pp. 4170-4177 (2000).
Mazzieri, R et al., Targeting The ANG2/TIE2 Axis Inhibits Tumor Growth And Metastasis By impairing Angiogenesis And Disabling Rebounds Of Proangiogenic Myelid Cells. Cell. Apr. 12, 2001, vol. 19, pp. 512-526; DOI: 10.1016/j.ccr.2001.02.005.
Mcpherson, "Current Approaches to Macromolecular Crystallization", Eur. J. Biochem, 189:1-23 (1990).
Medebielle, et al., "A Convenient Synthesis of Perfluoroalkylated and Fluorinated-Aryl Nitrogen Bases by Electrochemically Induced SRN1 Substitution", J. Org. Chem., 61:1331-1340 (1996).
Medebielle, et al., "A New Convenient Synthesis of 5-Aryl Uracils Using SRN1 Aromatic Nucleophilic Substitution", Tetrahedron Letters, 34(21 ):3409-3412 (1993).
Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979).
Mol, "Structural Basis for the Autoinhibition and STI-571 Inhibition of c-Kit Tyrosine Kinase," The Journal Of Biological Chemistry, 279(30):31655-31663 (2004).

Morris, et al., "Automated Docking of Flexible Ligands to Macromolecules", AutoDock Website, www.scripps.edu/mb/olson/doc/autodock/, printed March 3, (2005).
Morris, et al., "Automated Docking Using a Lamarckian Genetic Algorithm and an Empirical Binding Free Energy Function", Journal of Computational Chemistry, 19(14):1639-1662 (1998).
Morstyn, et al., "Stem Cell Factor Is a Potent Synergistic Factor in Hematopoiesis", Oncology, 51 :205-214 (1994).
Moss, et al., "Basic Terminology of Stereochemistry", Pure & Appl. Chem., 6812):2193-2222 (1996).
Muller, "Glossary of Terms Used in Physical Organic Chemistry", Pure & Appl. Chem., 66(5):1077-1184 (1994).
Muller, et al., "A General Synthesis of 4-Substituted 1, 1-Dioxo-1,2,5-thiadiazolidin-3-ones Derived from a-Amino Acids", J. Org. Chem., 54:4471-473 (1989).
Murayama, et al., "JNK (c-Jun NH2 Terminal Kinase) and p38 During Ischemia Reperfusion Injury in the Small Intestine" Transplantation, 81(9):1325-1330 (2006).
Mutlib, et al., "Disposition of 1-[3-(Aminomethyl)phenyl]-N-[3-fluoro-2'-(methylsulfonyl)-[1, 1 '-biphenyl]-4-yl]-3(trifluomethyl)-1 H-pyrazole-5-carboxamide (DPC 423) by Novel Metabolic Pathways. Characterization of Unusual Metabolites by Liquid Chromatography/Mass Spectrometry and NMR", Chem. Res. Toxicol., 15:48-62 (2002).
Mutlib, et al., "P450-Mediated Metabolism of 1-[3-(Aminomethyl)phenyl]-N-[3-fluoro-2'-(methylsulfonyl)-[1, 1 '-biphenyl]-4-yl]-3(trifluomethyl)-1 H-pyrazole-5-carboxamide (DCP 423) and Its Analogues to Aldoximes. Characterization of Glutathione Conjugates of Postulated Intermediates Derived from Aloximes", Chem. Res. Toxicol., 15:63-75 (2002).
Nagano, M. et al., "Studies on Organic Sulfur Compounds. XIV. The Reaction of N-alkoxycarbonyl-N'-(2-thiazolyl)thioureas with some oxidants." Chemical and Pharmaceutical Bulletin. vol. 21, No. 11, pp. 2408-2416. ISSN: 0009-2363. Nov. 1973.
Nagar, et al., "Crystal Structures of the Kinase Domain of c-Abl in Complex with the Small Molecule Inhibitors PD173955 and Imatinib (STI-571 )", Cancer Research, 62:4236-4243 (2002).
Nagata, et al., "Identification of a point mutation in the catalytic domain of the protooncogene c-kit in peripheral blood mononuclear cells of patients who have mastocytosis with an associated hematologic disorder," Proc. Natl. Acad. Sci. USA, 92(23):10560-10564 (1995).
Nager, et al., "Structural Basis for the Autoinhibition of c-Abl Tyrosine Kinase," Cell (Mar. 21, 2003) vol. 112, pp.859-871.
Nakopoulou, et al., "c-Met Tyrosine Kinase Receptor Expression is Associated with Abnormal !3-catenin Expression and Favourable Prognostic Factors in Invasive Breast Carcinoma", Histopatholoav, 36:313-325 (2000).
Nantaka-Namirski, et al., "Condensation Reaction of Ethyl (4-Uracil)-Acetate with Ethyl Orthoformate", ACTA Polon. Pharm XXVII, 28(5):455-463 (1971).
National Academy of Sciences, "Abstracts of Papers Presented at the Autumn Meeting, Nov. 14-16, 1960", Science, 132:1488-1501 (1960).
Nicolaou, et al., "Molecular Design and Chemical Synthesis of a Highly Potent Epothilone", ChemMedChem, 1 :41-44 (2006).
Nikolaev, et al., "Solubility Polytherm in the System HNO3-H2O-(C4H9O)PO(C4H9)2", Dokladv Akademii Nauk SSSR, 160(4):841-844 (1965).
Ning, et al., "Activating Mutations of c-Kit at Codon 816 Confer Drug Resistance in Human Leukemia Cells," Leukemia and Lymphoma, 41(5-6):513-522 (2001).
Nofal, et al., "Synthesis of Novel Uracil-5-Sulphonamide Derivatives of Possible Biological Activity", Egypt J. Chem., 33(4):375-380 (1990).
U.S. Appl. No. 11/963,740, filed Dec. 21, 2007, Patented, U.S. Pat. No. 8,163,756.
U.S. Appl. No. 11/870,388, filed Oct. 10, 2007, Patented, U.S. Pat. No. 7,790,756.
U.S. Appl. No. 12/829,561, filed Jul. 2, 2010, Patented, U.S. Pat. No. 8,586,565.
U.S. Appl. No. 11/854,354, filed Sep. 12, 2007, Patented, U.S. Pat. No. 8,188,113.

(56) References Cited

OTHER PUBLICATIONS

U.S. Appl. No. 10/746,460, filed Dec. 24, 2003, Patented, U.S. Pat. No. 7,144,911.
U.S. Appl. No. 10/886,329, filed Jul. 6, 2004, Patented, U.S. Pat. No. 7,202,257.
U.S. Appl. No. 11/450,840, filed Jun. 9, 2006, Patented, U.S. Pat. No. 7,342,037.
U.S. Appl. No. 11/336,708, filed Jan. 20, 2006, Patented, U.S. Pat. No. 7,531,566.
U.S. Appl. No. 11/450,850, filed Jun. 9, 2006, Patented, U.S. Pat. No. 7,666,895.
U.S. Appl. No. 10/746,607, filed Dec. 24, 2003, Patented, U.S. Pat. No. 7,279,576.
U.S. Appl. No. 11/854,293, filed Sep. 12, 2007, Patented, U.S. Pat. No. 7,897,762.
U.S. Appl. No. 12/105,408, filed Apr. 18, 2008, Patented, U.S. Pat. No. 8,143,293.
U.S. Appl. No. 13/590,955, filed Aug. 21, 2012, Patented, U.S. Pat. No. 8,486,951.
U.S. Appl. No. 11/450,849, filed Jun. 9, 2006, Patented, U.S. Pat. No. 7,737,283.
U.S. Appl. No. 13/785,575, filed Mar. 5, 2013, Patented, U.S. Pat. No. 8,741,911.
U.S. Appl. No. 12/608,578, filed Oct. 29, 2009, Patented, U.S. Pat. No. 8,278,331.
U.S. Appl. No. 13/098,247, filed Apr. 29, 2011, Patented, U.S. Pat. No. 8,569,319.
U.S. Appl. No. 13/559,170, filed Jul. 26, 2012, Patented, U.S. Pat. No. 8,637,672.
U.S. Appl. No. 14/214,134, filed Mar. 14, 2014, Patented, U.S. Pat. No. 9,133,183.
U.S. Appl. No. 14/383,803, filed Mar. 5, 2013, Patented, U.S. Pat. No. 9,187,474.
U.S. Appl. No. 13/491,394, filed Jun. 7, 2012, Patented, U.S. Pat. No. 8,461,179.
U.S. Appl. No. 13/801,753, filed Mar. 13, 2013, Patented, U.S. Pat. No. 8,940,756.
U.S. Appl. No. 16/387,315, filed Apr. 17, 2019, Pending.
U.S. Appl. No. 14/214,127, filed Mar. 14, 2014, Patented, U.S. Pat. No. 9,012,635.
U.S. Appl. No. 13/683,277, filed Nov. 21, 2012, Patented, U.S. Pat. No. 8,921,565.
U.S. Appl. No. 14/549,125, filed Nov. 20, 2014, Patented, U.S. Pat. No. 9,387,202.
U.S. Appl. No. 14/214,160, filed Mar. 14, 2014, Patented, U.S. Pat. No. 9,193,719.
U.S. Appl. No. 14/214,171, filed Mar. 14, 2014, Patented, U.S. Pat. No. 9,181,223.
U.S. Appl. No. 14/214,185, filed Mar. 14, 2014, Patented, U.S. Pat. No. 9,382,228.
U.S. Appl. No. 14/214,179, filed Mar. 14, 2014, Patented, U.S. Pat. No. 9,309,224.
U.S. Appl. No. 14/383,799, filed Mar. 5, 2013, Patented, U.S. Pat. No. 9,334,267.
U.S. Appl. No. 14/535,900, filed Nov. 7, 2014, Patented, U.S. Pat. No. 9,457,019.
U.S. Appl. No. 15/957,888, filed Apr. 19, 2018, Pending, US 2019-0091217 A1.
U.S. Appl. No. 16/617,721, filed Nov. 27, 2019, Pending, US 2020-0129489 A1.
U.S. Appl. No. 17/028,591, filed Sep. 22, 2020, Pending, US 2021-0015801 A1.
U.S. Appl. No. 16/943,821, filed Jul. 30, 2020, Pending.
U.S. Appl. No. 16/725,282, filed Dec. 23, 2019, Pending, US 2020-0253973 A1.
U.S. Appl. No. 16/870,384, filed May 8, 2020, Pending, US 2020-0354352 A1.
U.S. Appl. No. 16/870,418, filed May 8, 2020, Pending, US 2020-0354346 A1.
U.S. Appl. No. 16/902,989, filed Jun. 16, 2020, Pending.
U.S. Appl. No. 16/991,644, filed Aug. 12, 2020, Pending.
U.S. Appl. No. 17/028,640, filed Sep. 22, 2020, Pending.
U.S. Appl. No. 17/180,218, filed Feb. 19, 2021, Pending.
U.S. Appl. No. 17/180,234, filed Feb. 19, 2021, Pending.
U.S. Appl. No. 17/180,241, filed Feb. 19, 2021, Pending.
Nowell, et al., "A Minute Chromosome in Human Chronic Granulocytic Leukemia," Science (Nov. 18, 1960) vol. 132, p. 1497.
O'Dell, et al., "Treatment of Rheumatoid Arthritis with Methotrexate Alone, Sulfasalazine and Hydroxychloroquine, or a Combination of All Three Medications", New England J. Med., 334(20):1287-1291 (1996).
O'Neill, "Targeting Signal Transduction as a Strategy to Treat Inflammatory Diseases", Nature Review Drug Discovery, Published Online Jun. 9, 2006, www.nature.com/reviews/druqdisc.
Okano, et al., "o-Bromophenylzinc Compound: A Readily Available and Efficient Synthetic Equivalent of o-Phenylene 1-Anion 2-Cation", Tetrahedron Letters 39:3001-3004 (1998).
Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).
Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistrv, 40:15797-15804 (2001).
Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).
Okram, Barun et al: "A General Strategy for Creating "Inactive-Conformation" Ab1 Inhibitors" Chemistry&Biology (Cambridge, MA, US), 13(7), 779-786 CODEN: CBOLE2; ISSN: 1074-5521, 2006, XP002469183 table 1 the whole document.
Palmer, Brian, D. et al: "Structure-Activity Relationships For 2-Anilino-6-Phenylpyrido[2,3-d]Pyrimidin-7(8H)-Ones As Inhibitors of the Cellular Checkpoint Kinase Wee1" Bioorganic & Medicinal Chemistry Letters, 15(7), 1931-1935 CODEN: BMCLE8; ISSN: 0960-894X, 2005, XP004789411 p. 1933.
Parang, et al., "Mechanism-based Design of a Protein Kinase Inhibitor", Nature Structural Bioloav, 8( 1 ):37-41 (2001).
Pargellis, et al., "Inhibition of p38 MAP Kinase by Utilizing a Novel Allosteric Binding Site", Nature Structural Bioloav, 9(4 ):268-272 (2002).
Park, et al., "Mechanism of met Oncogene Activation", Cell, 45:895-904 (1986).
Pearlman, et al., "Assisted Model Building with Energy Refinement", Amber Home Page, amber.scripts.edu.
Pedersen, "The Preparation of Some N-Methyl-1,2,3-Triazoles", Acta Chimica Scandinavica, 13(5):888-892 (1959).
Peng, et al., "Identification of Novel Inhibitors of BCR-ABL Tyrosine Kinase via Virtual Screening", Bioorganic & Medicinal Chemistry Letters, 13:3693-3699 (2003).
Pereira, et al., "The Role of c-kit and Imatinib Mesylate in Uveal Melanoma", Journal of Carcinogenesis, 4:19 (2005), downloaded from www.carcinogenesis.com/content/4/1/19, Sep. 3, 2008.
Peyssonnaux, C. et al., "The RaflMEK/ERK pathway: new concepts of activation," Biol. Cell (2001) 93: 53-62.
Picard, et al., Inhibitors of Acyl-CoA: Cholesterol O-Acyltrasferase. 17. Structure-Activity Relationships of Several Series of Compounds.
Pierrat, et al., "Solid Phase Synthesis of Pyridine-Based Derivatives from a 2-Chloro-5-Bromopyridine Scaffold," J Comb. Chem. (2005) 7 (6): 879-886.
Pluk, et al., "Autoinhibition of c-Abl," Cell (Jan. 25, 2002) vol. 108, pp. 247-259.
Ponzetto, et al., "A Novel Recognition Motif for Phosphatidylinositol 3-Kinase Binding Mediates Its Association with the Hepatocyte Growth Factor/Scatter Factor Receptor", Molecular and Cellular Bioloav, 13(8):4600-4608 (1993).
Raimbaul T, et al., "Effects of pH and KCl on the Conformations of Creatine Kinase from Rabbit Muscle", Eur. J. Biochem., 234:570-578 (1995).

(56) References Cited

OTHER PUBLICATIONS

Ranatunge, et al, "Synthesis and Selective Cyclooxygenase-2 Inhibitory Activity of a Series of Novel, Nitric Oxide Donor-Containing Pyrazoles," J Med Chem. (2004) 47: 2180-2193.
Rebek, et al. "Convergent Functional Groups: Synthetic and Structural Studies", J. Am. Chem. Soc., 107:7476-7481 (1985).
Rebek, et al., "Convergent Functional Groups. 2. Structure and Selectivity in Olefin Epoxidation with Peracids", J. Org. Chem., 51:1649-1653 (1986).
Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).
Regan, et al., "Pyrazole Urea-Based Inhibitors of p38 MAP Kinase: From Lead Compound to Clinical Candidate", J. Med. Chem., 45:2994-3008 (2002).
Regan, et al., "Structure-Activity Relationships of the p38a MAP Kinase Inhibitor 1-(5-tert-Butyl-2-p-tolyl-2H-pyrazol-3-yl )-3-[4-(2-morpholi n-4-yl-ethoxy)naph-thalen-1-yl]urea (BI RB 796)", J. Med. Chem., 46:4676-4686 (2003).
Rooney, et al., "Inhibitors of Gylcolic Acid Oxidase. 4-Substituted 3-Hydroxy-1 H-pyrrole-2,5-dione Derivatives", J. Med. Chem., 26(5):700-714 (1983).
Roux, et al., "ERK and p38 MAPK-Activated Protein Kinases: a Family of Protein Kinases with Diverse Biological Functions", Microbiology and Molecular Biology Reviews, 68(2):320-344 (2004).
Rowley, "A New Consistent Chromosomal Abnormality in Chronic Myelogenous Leukaemia identified by Quinacrine Flourescence and Giemsa Staining," Nature (Jun. 1, 1973) vol. 243, pp. 290-293.
Rubin, et al., "Gastrointestinal stromal tumour," The Lancet Oncology, 369(9574):1731-1741 (2007).
Russell, et al., "3-[3-(Piperdin-1-yl)propyl]indoles as Highly Selective h5-HT1D Receptor", J. Med. Chem., 42:4981-5001 (1999).
Rutkowski, et al., "Gastrointestinal stromal tumours (GIST)—2018", Oncology in Clinical Practice, 14(6):399-407 (2019).
Saiga, et al., "Consecutive Cross-Coupling of o-Phenylenedizinc Compound with Acyl and/or Aryl Halides in the Presence of Pd(0)-tris(2,4,6-trimethoxyphenyl)phosphine", Tetrahedron Letters, 41 :4629-4632 (2000).
Sakamoto, et al., "Condensed Heteroaromatic Ring Systems. XIX. Synthesis and Reactions of 5-(Tributylstannyl)Isoxazoles", Tetrahedron, 4 7(28):5111-5118 (1991).
Sakuma, et al., "c-kit Gene Mutations in Intracranial Germinomas", Cancer Sci, 95(9):716-720 (2004).
Salgia, "Studies on c-Kit and c-Met in Lung Cancer with Similarities to Stem Cells," Microscopy Society of America, 11(2):1-30 (2005).
Satsangi, et al., "1-(4-Substituted-thiazol-2-yl)hydatoins as Anti-inflammatory and CNS Active Agents", Pharmazie, 38:341-342 (1983).
Sawyers, "Chronic Myeloid Leukemia," The New England Journal of Medicine (Apr. 29, 1999) vol. 340, No. 17, pp. 1330-1340.
Schindler, et al., "Structural Mechanism for STI-571 Inhibition of Abelson Tyrosine Kinase." Science (Sep. 15, 2000) vol. 289, pp. 1938-1942.
Schlosser, et al., "Regiochemically Flexible Substitutions of Di-, Tri-, and Tetrahalopy:ridines: The Trialkylsily Trick," J Org. Chem. (2005) 70: 2494-2502.
Schmidt, et al., "Germline and Somatic Mutations in the Tyrosine Kinase Domain of the MET proto-oncogene in Papillary Renal Carcinomas", Nature Genetics, 16:68-73 (1997).
Schmidt, et al., "Novel Mutations of the MET Proto-oncogene in Papillary Renal Carcinomas", Oncoqene, 18:2343-2350 (1999).
Schneeweiss Mathias, et al., "The KIT and PDGFRA switch-control inhibitor DCC-2618 blocks growth and survival of multiple neoplastic cell types in advanced mastocytosis," Haematologica (2018) vol. 103, No. 5, pp. 799-809.
Schneeweiss Mathias, et al., "The Multi-Kinase Inhibitor DCC-2618 Inhibits Proliferation and Survival of Neoplastic Mast Cells and Other Cell Types Involved in Systemic Mastocytosis," Blood (2016) vol. 128, No. 22, pp. 1965.
Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).
Seminario, et al., "Theoretical Study of a Molecular Resonant Tunneling Diode", J. Am. Chem. Soc., 122:3015-3020 (2000).
Seto, et al. "2-Substituted-4-aryl-6, 7 ,8,9-tetrahydro-5/ 1-p)'Timido [ 4, 5-b] [ 1,5 Joxazocin-5-oneasastrncturallynewNK1 antagonist," Biorg Nied Chem. Tea. (2005) 15: 1485-1488.
Shah, et al., "Circular Dichroic Studies of Protein Kinase C and its Interactions with Calcium and Lipid Vesicles", Biochimica et Biophysica Acta, 1119:19-26 (1992).
Heinrich, et al., "Molecular Correlates of Imatinib Resistance in Gastrointestinal Stromal Tumors," Journal of Clinical Oncology, 24(29):4764-4774 (2006).
Heinrich, et al., "Primary and Secondary Kinase Genotypes Correlate With the Biological and Clinical Activity of Sunitinib in Imatinib-Resistant Gastrointestinal Stromal Tumor," Journal of Clinical Oncology, 26(33):5352-5359 (2008).
Honda, et al., "Determination of the Association Constant of Monovalent Mode Protein-Sugar Interaction by Capillary Zone Electrophoresis", Journal of Chromatography, 597:377-382 (1992).
Hu, et al., "Capillary Electrophoresis for the Analysis of Biopolymers", Anal., Chem., 74:2833-2850 (2002).
Huang, et al., "Inhibition of Nucleoside Transport by Protein Kinase Inhibitors", The Journal of Pharmacolo and Experimental Therapeutics, 304 2 :753-760 (2003).
Hubbard, "Crystal Structure of the Activated Insulin Receptor Tyrosine Kinase in Complex with Peptide Substrate and ATP Analo", EMBO, 16(18):5573-5581 (1997).
Hubbard, et al., "Crystal Structure of the Tyrosine Kinase Domain of the Human Insulin Receptor", Nature, 374:746-754 (1994).
Hughes, et al., "Modulation of the Glycogen Synthase Kinase-3 Family by Tyrosine Phosphor lation", EMBO, 122 :803-808 (1993).
Huse, et al., "Crystal Structure of the Cytoplasmic Domain of the Type I TGFI3 Receptor in Complex with FKBP12", Cell, 96:425-436 (1999).
Huse, et al., "The Conformational Plasticity of Protein Kinases," Cell (May 3, 2002) vol. 109, pp. 275-282.
Huse, et al., "The TGFI3 Receptor Activation Process: An Inhibitor-to Substrate-Binding Switch", Molecular Cell, 8:671-682 (2001).
Igarashi, et al., "Antimicrobial Activities of 2-arylthio-N-alkylmaleimides", Journal of Industrial Microbiolo, 9:91-96 (1992).
International Human Genome Sequencing Consortium, "Initial Sequencing and Analysis of the Human Genome", Nature, 409:860-921 (2001).
International Search Report and Written Opinion from PCT/US2012/041378, mailed Sep. 17, 2012.
International Search Report and Written Opinion from PCT/US2017/035005, mailed Feb. 22, 2018.
International Search Report and Written Opinion from PCT/US2019/016148, mailed Apr. 17, 2019.
International Search Report and Written Opinion from PCT/US2019/016161, mailed Apr. 23, 2019.
International Search Report and Written Opinion from PCT/US2020/045876, mailed Oct. 22, 2020.
International Search Report and Written Opinion from WO2008/034008 A3, mailed Apr. 11, 2008.
International Search Report issued for PCT/US2008/060833, mailed Sep. 30, 2008.
International Search Report issued for PCT/US2008/060867, mailed Sep. 29, 2008.
International Search Report issued for PCT/US2008/060896, mailed Sep. 29, 2008.
Ishida, et al., "Molecular Arrangement and Electrical Conduction of Self-Assembled Monola ers Made from Terphen I Thiols", Surface Sciences, 514:187-193 (2002).
Islip, et al., "Nitrofuryl Heterocyclics 3", Journal of Medicinal Chemistry, 16(11 ): 1309-1310 (1973).

(56) References Cited

OTHER PUBLICATIONS

Jackson, et al., "N-Terminal Mutations Activate the Leukemogenic Potential of the M risto lated form of c-abl", EMBO, 8(2):449-456 (1989).
Jackson, et al., "Pyridinylimidazole Based p38 MAP Kinase Inhibitors", Current Topics in Medicinal Chemist, 2:1011-1020 (2002).
Janku Filip et al., "Pharmacokinetic-driven phase I study of DCC-2618 a pan-KIT and PDGFR inhibitor in patients (pts) with gastrointestinal stromal tumor (GIST) and other solid tumors," J. Clin. Oncol. (2017) No. 15, Suppl 2515.
Janku, et al., "Abstract CT058: Ripretinib (DCC-2618) pharmacokinetics (PK) in a Phase I study in patients with gastrointestinal stromal tumors (GIST) and other advanced malignancies: A retrospective evaluation of the PK effects of proton pump inhibitors (PPIs)", American Association for Cancer Research, 79(13):1-4 (2019).
Jiang, et al., "Soft Docking": Matching of Molecular Surface Cubes, J. Mol. Biol., 219:79-102 (1991).
Jiang, et al., "Synthesis and SAR Investigations for Novel Melanin-Concentrating Hormone 1 Receptor (MCH1) Antagonists Part 1. The Discovery of Arylacetamides as Viable Replacements for the Dihydropyrimidione Moiety of an HTS Hit", J. Med. Chem., 50:3870-3882 (2007).
Johnson, "Circular Dichroism Spectroscopy and The Vacuum Ultraviolet Region", Ann. Rev. Phys. Chem., 29:93-114 (1978).
Johnson, "Protein Secondary Structure and Circular Dichroism: A Practical Guide", Proteins: Structure, Function, and Genetics, 7:205-214 (1990).
Johnson, et al., "An Evaluation of the Effect of Light Stabilisers on the Exterior Durability of Polyester Powder Coatings for the Architectural Market", Surface Coatings International, 3:134-141 (1999).
Johnson, et al., "The Stereochemistry of Oxidation at Sulfur Oxidation of 2-Thiabicyclo[2.2.1 ]Hpetane", Tetrahedron, 25:5649-5653 (1969).
Katritzky, et al., "Novel Chromophoric Heterocycles Based on Maleimide and Naphthoquinone", J. Heterocyclic Chem., 26:885-892 (1989).
Kern, et al., "Synthese von Makromolekeln einheitlicher Brol3e. II Mitt: Syntheses neuer Diololigo-urethane nach dem Duplikationsverfahren", Makromolekulara Chemie, 16:89-107 (1955).
Kettle et al., "Discovery of N-(4-{[5-Fluoro-7-(2-methoxyethoxy)quinazolin-4-yl]amino}phenyl)-2-[4-(propan-2-yl)-1H-1,2,3-triazol-1-yl]acetamide (AZD3229), a Potent Pan-KIT Mutant Inhibitor for the Treatment of Gastrointestinal Stromal Tumors" Journal of Medicinal Chemistry (2018), 61(19), 8797-8810.
Kim, et al., "Solid Phase Synthesis of Benzamidine and Butylamine-Derived Hydantoin Libraries", Molecular Diversity, 3:129-132 (1998).
Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).
Kleywegt, et al., "Detection, Delineation, Measurement and Display of Cavities in Macromolecular Structures", Acta Cryst, D50:178-185 (1994).
Koch, et al., "QSAR and Molecular Modelling for a Series of Isomeric X-Sulfanilamido-1-phenylpyrazoles", Quant. Struct. Act. Relat., 12:373-382 (1993).
Kolch, W., "Meaningful relationships: the regulation of the Ras/Raf/MEKJERK pathway by protein interactions," Biochem. J (2000) 351: 289-305.
Konopka, et al., "Cell Lines and Clinical Isolates Derived From Ph-positive Chronic Myelogenous Leukemia Patients Express c-abl Proteins With A Common Structural Alteration," Proc. Natl. Acad. Sci. (Mar. 1985) vol. 82, pp. 1810-1814.
Krasovitskii, et al., "Synthesis and Spectral-Luminescence Properties of Hetarylethylene Derivatives of 2,5-Diphenyloxazole and 2,5-Diphenyl-1,3,4-Oxadiazole", Khimiya Geterosiklicheskikh Soedinenii, 5:617-621 (1982).
Kuhn, et al., "The Genesis of High-Throughput Structure-Based Drug Discovery using Protein Crystallography", Analytical Techniques, Current Opinion in Chemical Biology, 6:704-710 (2002).

Kumar, et al., "P38 Map Kinases: Key Signalling Molecules as Therapeutic Targets for Inflammatory Diseases", Nature Reviews Drug Discovery, 2:717-726 (2003).
Kundrot, "Which Strategy for a Protein Crystallization Project", CMLS, Cell. Mol. Life Sci., 61 :525-536 (2004).
Kundu, et al., "Depropargylation Under Palladium-Copper Catatlysis: Synthesis of Diaryl Sulfides", Tetrahedron, 57:5885-5895 (2001).
Kurogi, et al., "Discovery of Novel Mesangial Cell Proliferation Inhibitors Using a Three-Dimensional Database Searching Method", J. Med. Chem., 44:2304-2307 (2001).
Kuse, et al., Synthesis of azide-fluoro-dehydrocoelentcrazine analog as a photoaffinitylabeling probe and photolysis of azide-fluoro-coelenterazine; Tetrahedron Lett. (2005) 61: 5754-5762.
Cortes, Javier, et al., "Eribulin Monotherapy Versus Treatment of Physician's Choice in Patients With Metastatic Breast Cancer (EMBRACE): A Phase 3 Open-label Randomised Study", The Lancet, vol. 377, No. 9769, Mar. 1, 2011 (Mar. 1, 2011), pp. 914-923, ISSN: 0140-6736, DOI: 10.1016/S0140-6736(11 )60070-6.
Cross, et al., "Inhibition of Glycogen Synthase Kinase-3 by Insulin Mediated by Protein Kinase B", Nature, 378:785-789 (1995).
Cudney, "Preface: Protein Crystallization and Dumb Luck", The Rigaku Journal, 16(1): 1-7 (1999).
Dajani, et al., "Crystal Structur of Glycogen Synthase Kinas 3j3: Structural Basis for Phosphate-Primed Substrate Specificity and Autoinhibition", Cell, 105:721-732 (2001).
Dajani, et al., "Structural Basis for Recruitment of Glycogen Synthase Kinase 313 to the Axin-APC Scaffold Complex", EMBO, 22(3):494-501 (2003).
Daley, et al., "Induction of Chronic Myelogenous Leukemia in Mice by the P21 otcriat, Gene of the Philadelphia Chromosome," Science (Feb. 16, 1990) vol. 247, pp. 824-830.
Database Registry [Online] Chemical Abstracts Service, Columbus, Ohio, US; May 27, 2010, XP002777425, retrieved from STN accession No. 1225278-16-9 RN (2 pages).
Davies, H. et al., "Mutations of the BRAF gene in human cancer," Nature (Jun. 2002) 41 7: 949-954.
Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).
De Boer, et al., "Synthesis and Characterization of Conjugated Mono- and Dithiol Oligomers and Characterization of Their Self-Assembled Monolayers", Langmuir, 19:4272-4284 (2003).
De Palma et al., "Angiopoietin-2 TIEs Up Macrophages in Tumor Angiogenesis" Clin Cancer Res; 17(16) Aug. 15, 2011.
De Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1 ):13-19 (2003).
Debiec-Rychter, et al., "Mechanisms of Resistance to Imatinib Mesylate in Gastrointestinal Stromal Tumors and Activity of the PKC412 Inhibitor Against Imatinib-Resistant Mutants," Gastroenterology, 128(2):270-279 (2005).
Deciphera Pharmaceuticals LLC, "DCC-2618, a small molecule inhibitor of normal and mutant KIT kinase for treatment of refractory gastrointestinal stromal tumors (GIST)" (Presented on Sep. 24, 2011 at GIST Summit 2011 on "Gastrointestinal stromal tumors.").
Deciphera Pharmaceuticals LLC, "Deciphera Pharmaceuticals announces positive top-line results from INVICTUS pivotal phase 3 clinical study of Ripretinib in patients with advanced gastrointestinal stromal tumors", 1-3 (2019).
Deciphera Pharmaceuticals LLC, "Deciphera Pharmaceuticals Initiates Pivotal Phase 3 Clinical Study of Ripretinib (DCC-2618) in Second-line Patients with Gastrointestinal Stromal Tumors ("INTRIGUE" Study)", 1-2 (2018).
Deciphera Pharmaceuticals LLC, "Qinlock Full Prescribing Information", 1-18 (2020).
Deng, et al., "Expression, Characterization, and Crystallization of the Pyrophosphate-Dependent Phosphofructo-1-Kinase of Borrelia Burgdorferi", Archives of Biochemistry and Biophysics, 371(2):326-331 (1999).

(56) References Cited

OTHER PUBLICATIONS

Dess, et al., "A Useful 12-1-5 Triacetoxyperiodiane (the Dess-Martin Periodiane) for Selective Oxidation of Primary or Secondary Alcohols and a Variety of Related 12-1-5 Species", J. Am. Chem., Soc., 113:7277-7287 (1991).

Dong, J., Overcoming Resistance To BRAF And MEK inhibitors By Simultaneous Suppression Of CDK4. InTech. Jan. 30, 2013. Melanoma—From Early Detection to Treatment, Chapter 1; abstract; p. 7, second paragraph; p. 9, figure 4; DOI: 10.5772/53620.

Dumas, "Preface", Current Topics in Medicinal Chemistry (2002).

Dumas, "Protein Kinase Inhibitors: Emerging Pharmacophores", Exp. Opin. Ther. Patent, 11 :405-429 (2001).

Dumas, et al., "Discovery of a New Class of p38 Kinase Inhibitors", Bioorganic & Medicinal Chemistry Letters, 10:2047-2050 (2000).

Dumas, et al., "Recent Developments in the Discovery of Protein Kinase Inhibitors From the Urea Ciass," Current Opinion in Drug Discovery & Development (2004) vol. 7, No. 5, pp. 600-616.

Ettmayer, et al., "Lessons Learned from Marketed and Investigational Prodrugs," Journal of Medicinal Chemistry (May 6, 2004) vol. 47, No. 10, pp. 2393-2404.

Ewing, "Critical Evaluation of Search Algorithms for Automated Molecular Docking and Database Screeninq", Journal of Computational Chemistry, 18(9):1175-1189 (1997).

Examination Report in Indian Patent App. No. 11241/DELNP/2014 mailed Apr. 1, 2019.

Faderl, et al., "The Biology of Chronic Myeloid Leukemia," The New England Journal of Medicine (Jul. 15, 1999) vol. 341. No. 3, pp. 164-172.

Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).

Fathalla, "Synthesis of New Pyrazolo[1,5-a]pyrimidine Derivative Using 5-Aminouracil and Ketene Dithiacetal", Arch Pharm Res, 22(6):571-574 (1999).

Fathalla, et al., "Synthesis of New Uracil-5-Sulfonamide Derivatives and Immuno-Stimulatory Effect of a Chemically Modified Hemolymph of Biomphalaria Alexandrina on Schistosoma Manosi Infected Mice", Arch Pharm Res., 26(5):358-366 (2003).

Fathalla, et al., "Synthesis of New Uracil-5-Sulphonamide-p-Phenyl Derivatives and Their Effect on Biomphalaria Alexandrina Snail's Nucleoproteins", Arch. Pharm. Res., 23(2):128-138 (2000).

Flatt, et al., "Synthesis of Thiol Substituted Oligoanilines for Molecular Device Candidates", Tetrahedron Letters, 44:6699-6702 (2003).

Fletcher, et al., "Diagnosis of Gastrointestinal Stromal Tumors: A Consensus Approach", 33(5):459-465 (2002).

Fletcher, et al., "KIT Mutations in GIS, Current Opinion in Genetics & Development," Science Direct, p. 3-7 (2007).

Frame, et al., "A Common Phosphate Binding Site Explains the Unique Substrate Specificity of GSK3 and Its Inactivation by Phosphorylation", Molecular Cell, 7:1321-1327 (2001).

Furyua, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).

Gajiwala, et al., "KIT kinase mutants show unique mechanisms of drug resistance to imatinib and sunitinib in gastrointestinal stromal tumor patients," Proceedings of the National Academy of Sciences of the USA 106(5):1542-1547 (2009).

Garcia-Tellado, et al., "Molecular Recognition in the Solid Waste State: Controlled Assembly of Hydrogen-Bonded Molecular Sheets", J. Am. Chem. Soc., 113:9265-9269 (1991).

George, et al., "Initial Results of Phase 1 Study of DCC-2618, a Broad-Spectrum Kit and PDGFRA Inhibitor, in Patients (PTS) with Gastrointestinal Stromal Tumor (GIST) by Number of Prior Regimes", European Society for Medical Oncology, 1-13 (2018).

Gishizky, et al., "Efficient transplantation of BCR-ABL-induced Chronic Myelogenous Leukemia-like Syndrome in Mice," Proc. Natl. Acad. Sci. (Apr. 1993) vol. 90, pp. 3755-3759.

Gorre, et al., "Clinical Resistance to STI-571Cancer Therapy Caused by BCR-ABL Gene Mutation or Amplification," Science (Aug. 3, 2001) vol. 293, pp. 876-880.

Greene, et al., "Chapter 7: Protection for the Amino Group", in Protective Groups in Organic Synthesis, Third Edition, pp. 494-653 (1999).

Griffith, et al., "TPAP: Tetra-n-propylammonium Perruthenate, A Mild and Convenient Oxidant for Alcohols", Aldrichimica Acta, 23(1):13-19 (1990).

Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).

Haar, et al., "Structure of GSK313 Reveals a Primed Phosphorylation Mechanism", Nature Structural Bioloav, 8(7):593-596 (2001).

Hackler, et al., "The Syntheses of 5-Amino-3-t-butylisothiazole and 3-Amino-5-t-butylisothiazole," J. Heterocyclic Chem. (Nov.-Dec. 1989) vol. 26, pp. 1575-1578.

Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).

Hearing Notice in Indian Patent App. No. 11241/DELNP/2014 mailed Jan. 24, 2020.

Heegaard, et al., "Affinity Capillary Electrophoresis: Important Application Areas and Some Recent Developments", Journal ofChromatography B, 715:29-54 (1998).

Banks et al., Discovery and pharmacological characterization of AZD3229, a potent KIT/PDGFR inhibitor fortreatment of gastrointestinal stromal tumors, Sci. Transl. Med. 12, (2020).

Clinical trial NCT02571036—A Safety, Tolerability and PK Study of DCC-2618 in Patients With Advanced Malignancies—clinicaltrials.gov—Dec. 16, 2015.

Clinical trial NCT02571036—A Safety, Tolerability and PK Study of DCC-2618 in Patients With Advanced Malignancies—clinicaltrials.gov—Feb. 10, 2016.

Clinical trial NCT02571036—A Safety, Tolerability and PK Study of DCC-2618 in Patients With Advanced Malignancies—clinicaltrials.gov—Nov. 3, 2015.

Clinical trial NCT02571036—A Safety, Tolerability and PK Study of DCC-2618 in Patients With Advanced Malignancies—clinicaltrials.gov—Oct. 29, 2015.

International Search Report and Written Opinion from PCT/US2020/067557, mailed Apr. 23, 2021.

International Search Report and Written Opinion from PCT/US2020/067560, mailed Apr. 23, 2021.

Janku F. et al., "DCC-2618, a pan KIT and PDGFR switch control inhibitor, achieves proof-of-concept in a first-in-human study," Late Breaking Abstracts, Plenary Session 6, Dec. 1, 2016, p. s4.

Lu Jiade et al., "Advanced in the targeted therapy of cancer: multi targeted Raf kinase inhibitor," China Oncology, vol. 17, No. 1, (Dec. 31, 2007), pp. 1-7.

Office Action of U.S. Appl. No. 17/180,234 dated Apr. 29, 2021, 6 pages.

Office Action of U.S. Appl. No. 17/180,241 dated Aug. 20, 2021, 11 pages.

Office Action of U.S. Appl. No. 17/180,241 dated May 7, 2021, 9 pages.

Procenko, S.A., "Targeted Therapy in Melanoma, Gastrointestinal Stromal Tumors, Dermatofibrosarcoma Protuberans", Practical Oncology, vol. 11, No. 3, https://practical-oncology.ru/articles/196.pdf, (2010), pp. 162-170.

Reardon, D. et al., "Effect of CYP3A-inducing anti-epileptics on sorafenib exposure: results of a phase II study of sorafenib plus daily temozolomide in adults with recurrent gliosblastoma", J. Neurooncol. (2011), 101: pp. 57-66.

Reis, R. et al., "Molecular characterization of PDGFR-α/PDGF-A and c-KIT/SCF in gliosarcomas", Cellular Oncology, 2005; 27: pp. 319-326.

Remington, The Science and Practice of Pharmacy, Nineteenth Edition—1995, pp. 710-712.

Response to Office Action of U.S. Appl. No. 14/351,840 dated Sep. 28, 2015, 11 pages.

(56) References Cited

OTHER PUBLICATIONS

STN Registry Database RN 1225278-16-9.
Szucs, Z. et al., "Promising novel therapeutic approaches in the management of gastronitestinal stromal tumors", Future Oncology, (2017), vol. 13(2), pp. 185-194.
Tanno, F. et al., "Evaluation of Hypromellose Acetate Succinate (HPMCAS) as a Carrier in Solid Dispersions", Journal of Drug Development and Industrial Pharmacy, vol. 30, No. 1, pp. 9-17 (2004).
Vladimirova, L.U., "Usage of MEK Inhibitors in Oncology: Results and Perspectives", Modern Natural Science Successes, No. 3, https://s.natural-sciences.m/pdf/2015/3/34730.pdf., (2015), pp. 18-30.
Zustovich, F. et al., "Sorafenib plus Daily Low-dose Temozolomide for Relapsed Glioblastoma: A Phase II Study", Anticancer Research (2013), 33: pp. 3487-3494.
Shah, et al., "Overriding Imatinib Resistance with a Novel ABL Kinase Inhibitor," Science (Jul. 16, 2004) vol. 305, pp. 399-401.
Shi, et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).
Shinkai, et al., "Coenzyme Models, Part 45. Synthesis of Atropisomeric Flavins and their Novel Redox-induced Racemisation", J. Chem. Soc. Perkin Trans., pp. 313-319 (1988).
Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).
Sihto, et al., "KIT and Platelet-Derived Growth Factor Receptor Alpha Tyrosine Kinase Gene 1-30 Mutations and KIT Amplifications in Human Solid Tumors," Journal of Clinical Oncology, 23(1):49-57 (2005).
Sircar, et al., "Synthesis of 4-Hydroxy-N-[5-{hydroxymethyl)-3-isoxazolyl]2-methyl-2H-1,2-bsnzo-thiazine-3-carboxamide 1, 1-Dioxide and [(5-Methyl-3-isoxazolyl)amino]oxoacetic Acid. Major Metabolites of Isoxicam," J. Org. Chem. (1985) vol. 50, pp. 5723-5727.
Smith et al., "Ripretinib (DCC-2618) is a switch control kinase inhibitor of a broad spectrum of oncogenic and drug-resistant KIT and PDGFRA variants," Cancer Cell (2019), vol. 35, No. 5, pp. 738-759.
Stout, et al., "High-Throughput Structural Biology in Drug Discovery: Protein Kinases", Current Pharmaceutical Design, 10:1069-1082 (2004).
Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).
Tanis, et al., "Two Distinct Phosphorylation Pathways Have Additive Effects on Abl Family Kinase Activation", Molecular and Cellular Bioloav, 23(11):3884-3896 (2003).
Tarn, et al., "Analysis of KIT Mutations in Sporadic and Familial Gastrointestinal Stromal Tumors: Therapeutic Implications through Protein Modeling," Clinical cancer research : an official journal of the American Association for Cancer Research, 11(10):3668-3677 (2005).
Teague, "Implications of Protein Flexibility for Drug Discovery", Nature Reviews, 2:527-541 (2003).
Tian, et al., "Activating c-kit Gene Mutations in Human Germ Cell Tumors," American Journal of Pathology, 154(6):1643-1647 (1999).
Tominaga, et al., "General model for Estimation of the Inhibition of Protein Kinases Using Monte Carlo Simulations", J. Med. Chem., 47:2534-2549 (2004).
Tremblay, et al., "Efficient Solid-Phase Synthesis of Sulfahydantoins", J. Comb. Chem., 4:429-435 (2002).
Tsuzuki, et al., "Synthesis and Structure-Activity Relationships of Novel ?-Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).

Van Etten, "Cycling, Stressed-out and Nervous: Ceiiuiar Functions of c-Abi," Trends in Cell Biology (May 1999) vol. 9, pp. 179-186.
Venter, et al., "The Sequence of the Human Genome", Science, 291:1304-1351, Feb. 16, 2001; Erratum, Jun. 8, 2001.
Von Bubnoff, et al., "BCR-ABL gene mutations in relation to clinical resistance of Philadelphia-chromosome-positive leukemia to STI571. a prospective study," The Lancet (Feb. 9, 2002) vol. 359, pp. 487-491.
Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).
Wan, et al., "Mechanism of Activation of the RAF-ERK Signaling Pathway by Oncogenic Mutations of B-RAF," Cell (Mar. 19, 2004) vol. 116, pp. 855-867.
Wardelmann, "Acquired resistance to imatinib in gastrointestinal stromal tumours caused by multiple KIT mutations," The Lancet Oncology, 6(4):249-251 (2005).
Welker, et al., "Glucocorticoid-Induced Modulation of Cytokine Secretion from Normal and Leukemic Human Myelomonocytic Cells", Int. Arch. Allergy Immunol, 109:110-115 (1996).
Wentland, et al., "3-Quinolinecarboxamides. A Series of Novel Orally-Active Antiherpetic Agents", J. Med. Chem., 36:1580-1596 (1993).
Wilson, et al., "The Structural Basis for the Specificity of Pyridinylimidazole Inhibitors of p38 MAP Kinase", Chemistry & Biology, 4(6):423-431 (1997).
Wilson, et el., "Laser-Jet Delayed Trapping: Electron-Transfer Trapping of the Photoenol from 2-Methylbenzophenone", J. Am. Chem. Soc., 109:4743-4745 (1987).
Wolter, et al., "Copper-Catalyzed Coupling of Aryl Iodides with Aliphatic Alcohols", Organic Letters, 4(6):973-976 (2002).
Wrana, et al., "Mechanism of Activation of the TGF-B Receptor", Nature, 370:341-347 (1994).
Wu, et al., "Discovery of a Novel Family of CDK Inhibitors with the Program LIDAEUS:Structual Basis for Ligand-Induced Disordering of the Acivation Loop", Structure, 11:399-410 (2003).
Yang, et al., "Molecular Mechanism for the Regulation of Protein Kinase B/Akt by Hydrophobic Motif Phosphorylation", Molecular Cell, 9:1227-1240 (2002).
Yang, et al., "Palladium-Catalyzed Amination of Arly Halides and Sulfonates", Journal of Organometallic Chemistry, 576:125-146 (1999).
Yarden, et al., "Human Proto-oncogene c-kit: a New Cell Surface Receptor Tyrosine Kinase for an Unidentified Ligand", The EMBO Journal, 6(11):3341-3351 (1987).
Yoneda, et al., "A New Synthesis of Purines", J.C.S. Chem. Comm., pq. 551 (1974).
Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).
Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Dehydrogenase, Glutamate Dehydrogenase, Lactate Dehydrogenase, and Glyceraldehydephosphate Reductase, Malate Dehydrogenase", Journal of Medicinal Chemistry, 19(1):71-98 (1976).
Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).
Yu, et al., "Frequency of TPR-MET Rearrangement in Patients with Gastric Carcinoma and in First-Degree Relatives", Cancer, 88(8):1801-1806 (2000).
Zaidi, et al., "New Anti-Mycobacterial Hydantoins", Pharmazie, 35:755-756 (1980).
Zhen, et al., "Structural and Functional Domains Critical for Constitutive Activation of the HGF-Receptor (Met)", Oncogene, 9(6):1691-1697 (1994).
Zinner, et al., "Zur Weiteren Kenntnis Bicyclischer 3.5-Dioxopyrazolidine", Die Pharmazie, 25(5):309-312 (1970).

(56) References Cited

OTHER PUBLICATIONS

Zvilichovsky, et al., "Aminolysis and Polymerization of 3-(p-Toluenesulfonoxy) Hydantoin", Israel Journal of Chemistry, 7:547-554 (1969).
Assessment Report for Tukysa (tucatinib), European Medicines Agency, Dec. 10, 2020.
Deciphera Pharmaceuticals: "Highlights of Prescribing Information These highlights do not include all the information needed to use Qinlock safely and effectively. See full prescribing information for Qinlock," (May 1, 2020), retrieved from internet: https://www.accessdata.fda.gov/drugsatfda_docs/label/2020/213973s000lbl.pdf, 18 pages.
International Preliminary Report on Patentability of PCT/US2022/028456 dated Nov. 23, 2023, 10 pages.
Janku, F. et al., "Phase 1 study of ripretinib, a broad-spectrum KIT and PDGFRA inhibitor, in patients with KIT-mutated or KIT-amplified melanoma," ESMO Congress Virtual Meeting, (Sep. 16, 2021), p. 1.
Janku, F. et al., "Phase I study of ripretinib, a broad-spectrum KIT and PDGFRA inhibitor, in patients with KIT-mutated or KIT-amplified melanoma," Annals of Oncology, vol. 32, (Sep. 1, 2021), p. S896.
Janku, F. et al., "Ripretinib Demonstrates Impressive Efficacy, Durability in Heavily Pretreated KIT-Mutated Melanoma," (Dec. 6, 2021), retrieved from https://www.onclive.com/view/ripretinib-demonstrates-impressive-efficacy-durability-in-heavily-pretreated-kit-mutated-melanoma, access on Feb. 5, 2024.
Kalinsky, K. et al., "A Phase II Trial of Dasatinib in Patients with Locally Advanced or Stage IV Mucosal, Acral and Vulvovaginal Melanoma: A Trial of the ECOG-ACRIN Cancer Research Group (E2607)," American Cancer Society, vol. 123, No. 14, (Mar. 23, 2017), pp. 2688-2697.
Li, X. et al., "Effect of hepatic impairment on the pharmacokinetics of ripretinib," Journal of Clinical Oncology, V. 40, No. 16, suppl., e16031, (2022), 1 page.
Pham, D. M. et al., "KIT and Melanoma: Biological Insights and Clinical Implications," Yonsei Medical Journal, vol. 61, No. 7, (Jul. 1, 2020), pp. 562-571.
Protsenko, S.A., "Targeted Therapy in Melanoma, Gastrointestinal Stromal Tumors, Dermatofibrosarcoma Protuberans", Practical Oncology, vol. 11, No. 3, (2010), pp. 162-170.

* cited by examiner

HMC1.1 V560G          HMC1.1 V560G/D816V

HMC1.1 V560G                    HMC1.1 V560G/D816V

Figure 2B

| COMBO Index | Compound A 5nM | Compound A 10nM | Compound A 25nM | Compound A 50nM | Compound A 100nM | Compound A 200nM |
|---|---|---|---|---|---|---|
| Trametinib 1nM | 0.03993 | 2.64367 | 6.01481 | 0.44649 | 0.11076 | 0.01411 |
| Trametinib 5nM | 1.25589 | 0.19588 | 0.13256 | 0.05909 | 0.0101 | 0.00315 |
| Trametinib 10nM | 0.24985 | 0.23826 | 0.09809 | 0.03722 | 0.0063 | 9.34E-04 |
| Trametinib 25nM | 0.63422 | 0.36434 | 0.10901 | 0.03338 | 0.0032 | 8.28E-04 |
| Trametinib 50nM | 1.10038 | 0.48744 | 0.18814 | 0.03977 | 0.00477 | 9.35E-04 |
| Trametinib 100nM | 1.87791 | 1.06924 | 0.35501 | 0.04047 | 0.00308 | 6.93E-04 |

Figure 3B

| CI | Compound B 1nM | Compound B 5nM | Compound B 10nM | Compound B 25nM | Compound B 50nM | Compound B 100nM | Compound B 200nM |
|---|---|---|---|---|---|---|---|
| Trametinib 1nM | 1.68069 | 1.40334 | 3.41889 | 5.07162 | 5.64363 | 0.57337 | 0.00964 |
| Trametinib 5nM | 1.05523 | 2.96535 | 1.86572 | 1.4174 | 0.53113 | 0.00478 | 2.29E-05 |
| Trametinib 10nM | 5.38596 | 3.16063 | 2.68309 | 1.06576 | 0.56445 | 2.84E-04 | 1.44E-05 |
| Trametinib 25nM | 1.94547 | 1.57549 | 0.96476 | 0.03258 | 0.00435 | 1.97E-05 | 2.51E-07 |
| Trametinib 50nM | 0.85054 | 1.07585 | 0.6726 | 0.0344 | 0.00289 | 3.12E-05 | 7.64E-07 |
| Trametinib 100nM | 0.97626 | 0.35944 | 0.48969 | 0.06284 | 0.00169 | 1.52E-05 | 2.14E-07 |
| Trametinib 200nM | 2.11003 | 0.45464 | 0.48568 | 0.08116 | 0.00419 | 3.14E-05 | 1.63E-06 |

Figure 4B

| CI | Compound A 0nM | Compound A 5nM | Compound A 10nM | Compound A 25nM | Compound A 50nM | Compound A 100nM | Compound A 250nM | Compound A 500nM |
|---|---|---|---|---|---|---|---|---|
| Binimetinib 25 nM | 1.57049 | 1.6855 | 1.51394 | 1.54333 | 0.74303 | 0.23806 | 0.07988 | 0.00293 |
| Binimetinib 50 nM | 1.78444 | 1.57824 | 1.10552 | 1.1015 | 0.33617 | 0.08494 | 0.00687 | 5.98E-04 |
| Binimetinib 100 nM | 1.40574 | 1.90927 | 0.81771 | 0.53885 | 0.15853 | 0.04623 | 0.00308 | 1.07E-04 |
| Binimetinib 250 nM | 2.92199 | 1.67399 | 0.69022 | 0.233 | 0.0771 | 0.03398 | 0.00408 | 1.07E-04 |
| Binimetinib 500 nM | 2.19283 | 0.50712 | 0.29592 | 0.13935 | 0.06226 | 0.02526 | 0.00273 | 5.07E-04 |
| Binimetinib 1000 nM | 1.38598 | 0.3404 | 0.14626 | 0.12693 | 0.08277 | 0.02281 | 0.00192 | 9.26E-05 |
| Binimetinib 2000 nM | 0.73725 | 0.15871 | 0.13631 | 0.12471 | 0.08017 | 0.02714 | 0.00442 | 3.54E-04 |

Figure 5B

| CI | Compound B 1nM | Compound B 5nM | Compound B 10nM | Compound B 25nM | Compound B 50nM | Compound B 100nM | Compound B 200nM | Compound B 500nM |
|---|---|---|---|---|---|---|---|---|
| Binimetinib 25 nM | 1.16697 | 1.12369 | 1.92347 | 1.87175 | 1.33032 | 0.40022 | 0.08512 | 0.00433 |
| Binimetinib 50 nM | 0.80429 | 1.59151 | 1.83453 | 1.76275 | 0.64013 | 0.24461 | 0.04974 | 0.00128 |
| Binimetinib 100 nM | 2.04491 | 2.46708 | 1.33485 | 1.04913 | 0.35742 | 0.12945 | 0.03332 | 0.00166 |
| Binimetinib 250 nM | 1.19498 | 1.06822 | 0.83211 | 0.43195 | 0.20689 | 0.06245 | 0.01894 | 3.14E-05 |
| Binimetinib 500 nM | 1.32017 | 0.62726 | 0.56972 | 0.28981 | 0.15592 | 0.0513 | 0.00726 | 5.92E-05 |
| Binimetinib 1000 nM | 2.02996 | 0.4532 | 0.37085 | 0.30154 | 0.17875 | 0.06054 | 0.01473 | 0.00107 |
| Binimetinib 2000 nM | 0.8794 | 0.43685 | 0.25074 | 0.25665 | 0.1561 | 0.04969 | 0.0117 | 0.00191 |

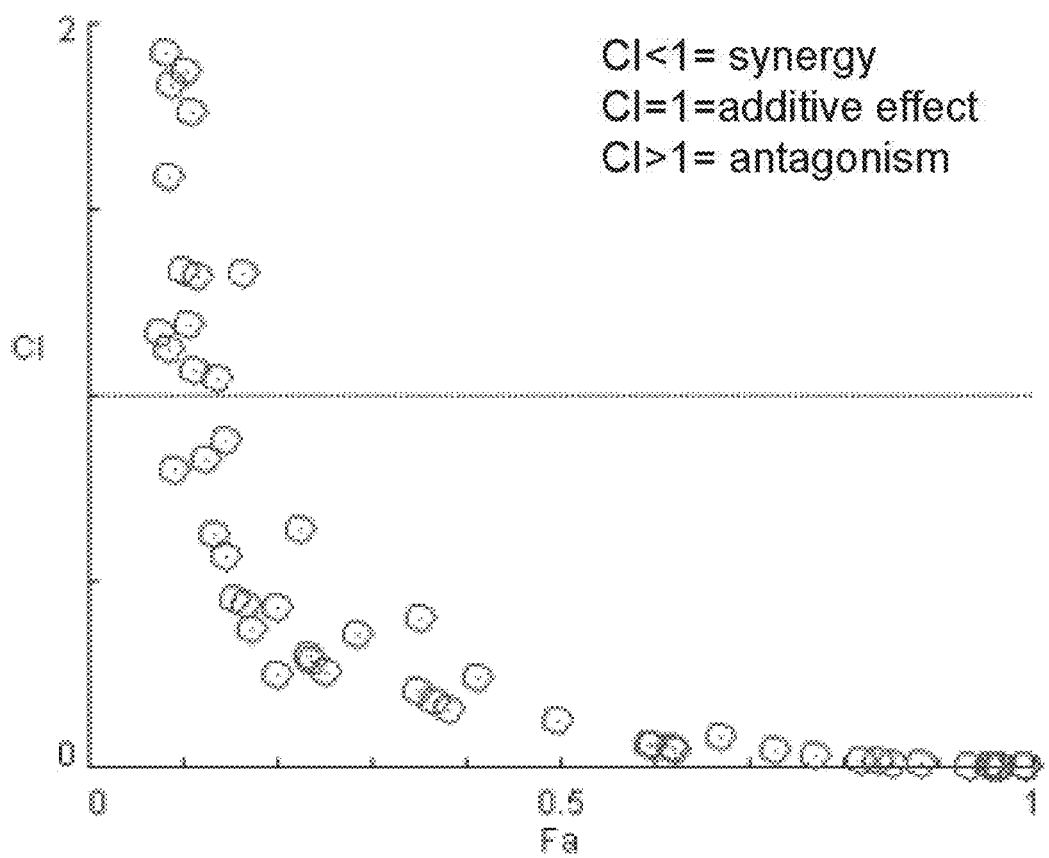

Figure 6B

| CI | Compound A 1nM | Compound A 5nM | Compound A 10nM | Compound A 25nM | Compound A 50nM | Compound A 100nM | Compound A 200nM |
|---|---|---|---|---|---|---|---|
| Cobimetinib 1 nM | 0.72367 | 2.58457 | 2.84957 | 6.37493 | 5.86712 | 0.38735 | 0.02608 |
| Cobimetinib 5 nM | 2.03327 | 2.22709 | 2.49475 | 1.92929 | 0.5199 | 0.02364 | 0.00107 |
| Cobimetinib 10 nM | 4.07508 | 3.47138 | 3.05888 | 1.91627 | 0.20704 | 0.00993 | 1.78E-04 |
| Cobimetinib 25 nM | 4.08228 | 1.74076 | 0.60978 | 0.22536 | 0.03575 | 0.0036 | 2.63E-04 |
| Cobimetinib 50 nM | 3.97974 | 0.59607 | 0.21652 | 0.07886 | 0.02071 | 0.00202 | 3.67E-05 |
| Cobimetinib 100 nM | 1.21021 | 0.08536 | 0.0658 | 0.03731 | 0.00925 | 0.00381 | 2.38E-05 |
| Cobimetinib 200 nM | 0.11777 | 0.03679 | 0.04185 | 0.02953 | 0.00733 | 2.49E-04 | 4.83E-08 |

Figure 7B

| CI | Compound B 1nM | Compound B 5nM | Compound B 10nM | Compound B 25nM | Compound B 50nM | Compound B 100nM | Compound B 200nM |
|---|---|---|---|---|---|---|---|
| Cobimetinib 1nM | 1.39961 | 3.77808 | 5.66631 | 9.38659 | 11.3003 | 2.06695 | 0.08926 |
| Cobimetinib 5nM | 5.34532 | 4.24727 | 2.63326 | 4.01626 | 5.27338 | 0.1571 | 0.00124 |
| Cobimetinib 10nM | 4.35207 | 2.99291 | 3.57716 | 3.86343 | 0.87975 | 0.01274 | 1.33E-04 |
| Cobimetinib 25nM | 2.75567 | 1.98415 | 2.09289 | 0.60486 | 0.03221 | 1.80E-04 | 1.49E-05 |
| Cobimetinib 50nM | 2.28329 | 0.93831 | 0.593 | 0.04964 | 0.00576 | 6.67E-05 | 8.50E-06 |
| Cobimetinib 100nM | 1.88398 | 0.34755 | 0.17375 | 0.03918 | 0.00578 | 1.98E-04 | 1.09E-05 |
| Cobimetinib 200nM | 0.79643 | 0.18837 | 0.12431 | 0.04216 | 0.00592 | 1.77E-04 | 1.29E-05 |

Combination index plot

Figure 8B

| CI | Compound A 1nM | Compound A 5nM | Compound A 10nM | Compound A 25nM | Compound A 50nM | Compound A 100nM | Compound A 250nM | Compound A 500nM |
|---|---|---|---|---|---|---|---|---|
| Ulixertinib 50 nM | 1.60258 | 2.92097 | 2.92056 | 2.33011 | 3.16429 | 3.40419 | 0.95172 | 0.0969 |
| Ulixertinib 100 nM | 2.34725 | 1.48965 | 1.55963 | 2.64283 | 2.89453 | 2.47874 | 0.83763 | 0.0861 |
| Ulixertinib 250 nM | 2.52682 | 1.04818 | 1.63023 | 1.59316 | 3.17247 | 2.16888 | 0.71586 | 0.03154 |
| Ulixertinib 500 nM | 0.5764 | 0.68476 | 1.29507 | 1.07784 | 1.14575 | 0.51154 | 0.12022 | 0.00349 |
| Ulixertinib 1000 nM | 0.25087 | 0.36296 | 0.45054 | 0.83564 | 0.31409 | 0.5004 | 0.065 | 2.04E-04 |
| Ulixertinib 2000 nM | 0.34059 | 0.33951 | 0.63595 | 0.77262 | 0.96933 | 0.75802 | 0.15375 | 7.35E-04 |
| Ulixertinib 5000 nM | 2.6495 | 5.10326 | 2.44488 | 2.61636 | 3.22495 | 2.41533 | 1.00502 | 0.03806 |

HMC1.2 cells

HMC1.2-EV cells

HMC1.2-Nras-G12D

HMC1.2 Nras G12D

Figure 18A

HMC1.2 EV cells

Figure 18B

Compound A and cobimetinib in HMC1.2-NRas G12D cells

COMBINATION THERAPY FOR THE TREATMENT OF MASTOCYTOSIS

CROSS-REFERENCE TO RELATED APPLICATIONS

This application is a continuation of International Application Number PCT/US2019/016161 filed Jan. 31, 2019, which claims priority to U.S. Ser. No. 62/624,453 filed Jan. 31, 2018, the contents of which are incorporated herein by reference in their entirety.

BACKGROUND c-KIT (also known as KIT, CD117, and stem cell factor receptor) is a 145 kDa transmembrane tyrosine kinase protein that acts as a type-III receptor. The c-KIT proto-oncogene, located on chromosome 4q11-21, encodes the c-KIT receptor, whose ligand is the stem cell factor (SCF, steel factor, kit ligand, mast cell growth factor). The receptor has tyrosine-protein kinase activity, and binding of the ligand SCF leads to the autophosphorylation of c-KIT and its association with substrates such as phosphatidylinositol 3-kinase (PI3K). Tyrosine phosphorylation by protein tyrosine kinases is of particular importance in cellular signaling and can mediate signals for major cellular processes, such as proliferation, survival, differentiation, apoptosis, attachment, invasiveness and migration.

The receptor tyrosine kinase c-KIT gene is critical for mast cell growth, survival, differentiation and homeostasis. Activating mutations or overexpression of the c-KIT gene enhances the ability of the c-KIT receptor to initiate the intracellular pathways resulting in aberrant mast cell proliferation.

Mastocytosis is a rare disorder characterized by abnormal accumulations of mast cells (MCs) in the skin, bone marrow, and internal organs (e.g., liver, spleen, gastrointestinal tract and lymph nodes). Cases beginning during adulthood tend to be chronic and involve the bone marrow in addition to the skin, whereas, during childhood, the condition is often marked by skin manifestations with no internal organ involvement and can often resolve during puberty. In most adult patients, mastocytosis tends to be persistent, and may progress into a more advanced category in a minority of patients. Mastocytosis can be classified to a specific type depending on the patient's symptoms and overall presentation. Types of mastocytosis include cutaneous mastocytosis (e.g., maculopapular cutaneous mastocytosis, mastocytoma, and diffuse cutaneous mastocytosis) and systemic mastocytosis (e.g., indolent systemic mastocytosis (ISM), systemic smoldering mastocytosis (SSM), systemic mastocytosis with associated clonal hematological non-mast cell lineage disease (SM-AHN), aggressive systemic mastocytosis (ASM), mast cell leukemia (MCL) and mast cell sarcoma). In rare cases, outgrowth of aggressive neoplastic mast cells results in end organ failure where the patients have significantly reduced lifespan and require cytoreductive therapy. The pathologic accumulation of neoplastic mast cells caused by oncogenic mutations of c-KIT was found to be causative of systemic mastocytosis. The predominant activating KIT mutation is the aspartic acid to valine substitution at residue 816 (KIT D816V). Patients with systemic mastocytosis, whose mast cells frequently contain the activating D816V c-KIT mutation, may have indolent to aggressive diseases, and they may experience mast cell mediator release related symptoms. Indolent systemic mastocytosis with recurrent anaphylaxis or vascular collapse in the absence of skin lesions is a specific subtype indolent systemic mastocytosis, and this clonal MC activation disorder represents a significant fraction of all mast cell activation syndromes. The V560G KIT mutation is extremely rare in patients with systemic mastocytosis, and its biological and prognostic impact is unclear. Currently, most tyrosine kinase inhibitors have demonstrated only modest efficacy in advanced disease states and are accompanied by significant side effects. Additionally, some aggressive KIT mutations, including the KIT D816V mutation, are resistant to classical ATP competitive KIT inhibitors such as imatinib, sunitinib, sorafenib, and regorafenib. Midostaurin, an inhibitor of c-KIT D816V, was recently approved for the treatment of SM in 2017.

While the c-KIT D816V mutation is the primary c-KIT mutation reported as a driver of systemic mastocytosis (SM), secondary c-KIT mutations that confer resistance to certain c-KIT inhibitors ("secondary resistance c-KIT mutations") have also been reported in mastocytosis patients, including, e.g., a Y269C, Y503_F504insAY, V560D, or K642E point mutation, an in-frame deletion or insertion, or a missense mutation in the c-KIT gene.

Activating mutations or overexpression of the c-KIT gene are linked to neoplastic mast cell proliferation. Given the complex function of c-KIT and the potential utility for c-KIT inhibitors in treating drug resistant systematic mastocytosis, there is a need for inhibitors and therapeutic treatments with advantageous therapeutic properties.

SUMMARY

The present disclosure, in part, relates to the use of a c-KIT inhibitor, e.g., 1-[4-bromo-5-[1-ethyl-7-(methylamino)-2-oxo-1,2-dihydro-1,6-naphthyridin-3- yl]-2-fluorophenyl]-3-phenylurea (Compound A), and a MAPKAP pathway inhibitor, e.g., a MEK inhibitor such as trametinib, or an ERK inhibitor such as ulixertinib, or a RAF inhibitor such as LY3009120, for inducing the apoptosis of mastocytosis cells.

Also provided in the present disclosure are methods of treating mastocytosis in a patient in need thereof, comprising administering to the patient: an effective amount of a c-KIT inhibitor, e.g., 1-[4-bromo-5-[1-ethyl-7-(methylamino)-2-oxo-1,2-dihydro-1,6-naphthyridin-3-yl]-2-fluorophenyl]-3-phenylurea (Compound A as described herein); and an effective amount of an inhibitor of a mitogen-activated protein kinase (MEK inhibitor), and/or an effective amount of an extracellular signal regulated kinase inhibitor (ERK inhibitor).

For example, provided herein is a method of treating a systemic mastocytosis in a patient in need thereof, comprising administering to the patient: an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof; and an effective amount of an inhibitor of a mitogen-activated protein kinase (MEK inhibitor) or ERK inhibitor.

Also contemplated in this disclosure is a method of treating mastocytosis in a patient in need thereof, comprising administering to the patient: an effective amount of a c-KIT inhibitor; and an effective amount of a RAF inhibitor.

BRIEF DESCRIPTION OF THE DRAWINGS

FIG. 2B provides a synergy matrix chart based on the combination index method for various treatments with Compound A and trametinib in the HMC1.2 V560G/D816V cell line.

FIG. 3B provides a synergy matrix chart based on the combination index method for various treatments with Compound B and trametinib in the HMC1.2 V560G/D816V cell line.

FIG. 4B provides a synergy matrix chart based on the combination index method for various treatments with Compound A and binimetinib in the HMC1.2 V560G/D816V cell line.

FIG. 5B provides a synergy matrix chart based on the combination index method for various treatments with Compound B and binimetinib in the HMC1.2 V560G/D816V cell line.

FIG. 5C provides a Combination Index Plot for the combination of Compound B with the MEK inhibitor binimetinib.

FIG. 6B provides a synergy matrix chart based on the combination index method for various treatments with Compound A and cobimetinib in the HMC1.2 V560G/D816V cell line.

FIG. 7B provides a synergy matrix chart based on the combination index method for various treatments with Compound B and cobimetinib in the HMC1.2 V560G/D816V cell line.

FIG. 8B provides a synergy matrix chart based on the combination index method for various treatments with Compound A and the ERK inhibitor ulixertinib in the HMC1.2 V560G/D816V cell line.

FIG. 18A shows the inhibition of colony outgrowth from treatment with single agent Compound A, single agent cobimetinib, and the combination of Compound A with the MEK inhibitor cobimetinib in an empty vector (EV) transfected HMC1.2 V560G/D816V cells.

FIG. 18B shows a graphical representation of inhibition of colony outgrowth from treatment with single agent Compound A, single agent cobimetinib, and the combination of Compound A with the MEK inhibitor cobimetinib in an empty vector (EV) transfected HMC1.2 V560G/D816V cells. Arrows indicate no colony outgrowth.

DETAILED DESCRIPTION

Figure 1A:
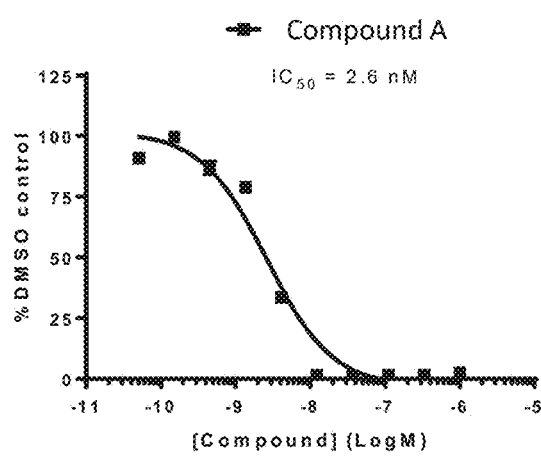
FIG. 1A shows graphical representations of cell proliferation following the indicated drug treatment with Compound A as compared to vehicle control in HMC1.1 V560G (left panel) and HMC1.2 V560G/D816V (right panel) cell lines.
Figure 1A:
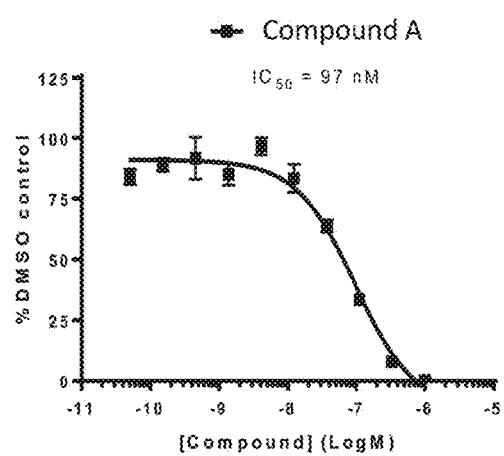

It is found that the combination of a c-KIT inhibitor, e.g., 1-[4-bromo-5-[1-ethyl-7-(methylamino)-2-oxo-1,2-dihydro-1,6-naphthyridin-3-yl]-2-fluorophenyl]-3-phenylurea (Compound A), and a MAPKAP pathway inhibitor, e.g., the MEK inhibitor trametinib, or the ERK inhibitor ulixertinib, or the RAF inhibitor LY3009120 unexpectedly synergizes to induce apoptosis of mastocytosis cells, as demonstrated in the accompanying Examples. In addition, the combination therapy methods disclosed herein are cytocidal as opposed to being merely cytostatic.

Without wishing to be bound to any particular theory, it is believed that many c-KIT inhibitors only inhibit certain mutant forms of c-KIT and do not effectively inhibit the c-KIT D816V mutation that is causative of SM. The present disclosure provides methods of treating c-KIT-mediated mastocytosis, by inhibiting both c-KIT and MEK, using a c-KIT inhibitor in combination with a MAPKAP pathway inhibitor. In particular embodiments, the c-KIT inhibitor is disclosed herein as Compound A or a pharmaceutically acceptable salt thereof, Compound B or a pharmaceutically acceptable salt thereof, midostaurin or a pharmaceutically acceptable salt thereof, BLU-285 or a pharmaceutically acceptable salt thereof, PLX9486 or a pharmaceutically acceptable salt thereof, or crenolanib or a pharmaceutically acceptable salt thereof. Surprisingly, the c-KIT inhibitor, e.g., Compound A and Compound B (and pharmaceutically acceptable salts thereof), synergizes with the MEK, ERK,or RAF, inhibitor to inhibit proliferation and induce apoptosis of mastocytosis cells.

Accordingly, in certain embodiments, the present disclosure provides methods for inducing inducing cytocidal mast cell killing, inducing apoptosis of mast cells, inhibiting growth or proliferation of mast cells, inhibiting mast cell mediator release, reducing the amount of accumulated mast cells in a tissue or organ, reducing the volume of a mastocytosis-related tumor, such as a mast cell leukemia or mast cell sarcoma, and/or inhibiting mast cell regrowth, by contacting mast cells, e.g., mast cells comprising a c-KIT mutation, with a c-KIT inhibitor and a MAPKAP pathway inhibitor. In various embodiments, the mast cells are contacted in vitro, in vivo, or ex vivo. In particular embodiments, the c-KIT inhibitor is disclosed herein as Compound A or a pharmaceutically acceptable salt thereof, Compound B or a pharmaceutically acceptable salt thereof, midostaurin or a pharmaceutically acceptable salt thereof, BLU-285 or a pharmaceutically acceptable salt thereof, PLX9486 or a pharmaceutically acceptable salt thereof, or crenolanib or a pharmaceutically acceptable salt thereof; and the MEK inhibitor disclosed herein as trametinib, cobimetinib, selumetinib, or binimetinib; ERK inhibitors including but not limited to ulixertinib, SCH772984, LY3214996, ravoxertinib, and VX-11e, and RAF inhibitors including but not limited to LY3009120, vemurafenib, or dabrafenib.

In certain embodiments, the present disclosure includes methods for treating a subject having a mastocytosis, a mast cell leukemia, or an acute myeloid leukemia, comprising administering to the subject an effective amount of: (i) a KIT inhibitor, e.g., 1-[4-bromo-5-[1-ethyl-7-(methylamino)-2-oxo-1,2-dihydro-1,6-naphthyridin- 3-yl]-2-fluorophenyl]-3-phenylurea or a pharmaceutically acceptable salt thereof, or 1-(5-(7-amino-1-ethyl-2-oxo-1,2-dihydro-1,6-naphthyridin-3-yl)-4-bromo-2-fluorophenyl)-3- phenylurea or a pharmaceutically acceptable salt thereof; and (ii) a MAPKAP pathway inhibitor, e.g., trametinib, binimetinib, ulixertinib. In particular embodiments of any of the methods disclosed herein, the mastocytosis is a systemic mastocytosis resulting from a D816V mutation of the c-KIT gene in mast cells.

Definitions

"Compounds A and B" as used herein refer to 1-[4-bromo-5-[1-ethyl-7-(methylamino)-2-oxo-1,2-dihydro-1,6-naphthyridin-3-yl]-2-fluorophenyl]- 3-phenylurea and 1-(5-(7-amino-1-ethyl-2-oxo-1,2-dihydro-1,6-naphthyridin-3-yl)-4-bromo-2-fluorophenyl)-3-phenylurea, respectively. Pharmaceutically acceptable salts, tautomers, hydrates, and solvates, of Compounds A and B are also contemplated in this disclosure. The structures of Compounds A and B are represented below:

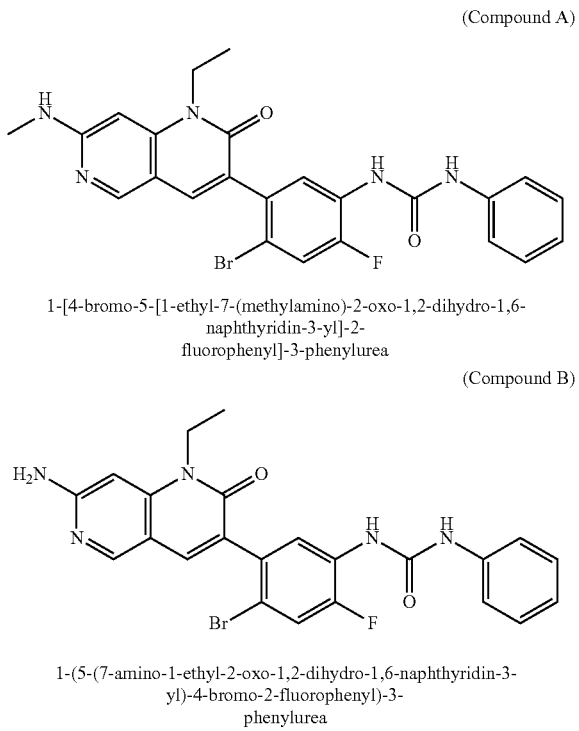

(Compound A)

1-[4-bromo-5-[1-ethyl-7-(methylamino)-2-oxo-1,2-dihydro-1,6-naphthyridin-3-yl]-2-fluorophenyl]-3-phenylurea (Compound B)

1-(5-(7-amino-1-ethyl-2-oxo-1,2-dihydro-1,6-naphthyridin-3-yl)-4-bromo-2-fluorophenyl)-3-phenylurea Methods of making Compound A and Compound B are disclosed in U.S. Pat. No. 8,461,179B1, the contents of which are incorporated herein by reference.

Illustrative methods and materials are described herein. In the specification and the appended claims, the singular forms also include the plural unless the context clearly dictates otherwise. Unless defined otherwise, all technical and scientific terms used herein have the same meaning as commonly understood by one of ordinary skill in the art.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications and this disclosure. For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes acid addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

A "pharmaceutical composition" refers to a formulation of a compound described herein (e.g., Compound A or a pharmaceutically acceptable salt thereof) and a medium generally accepted in the art for the delivery of the biologically active compound to mammals, e.g., humans. Such a medium includes all pharmaceutically acceptable carriers, diluents or excipients therefor.

A "MAPKAP pathway inhibitor" is an inhibitor of the MAP kinase signaling pathway. Inhibitors of this pathway include RAS inhibitors, RAF inhibitors (e.g. vemurafenib, dabrafenib, LY3009120), MEK inhibitors (e.g. trametinib, binimetinib, cobimetinib), and ERK inhibitors (e.g. ulixertinib).

Subjects or patients "in need of treatment" with a combination therapy of the present disclosure, e.g., a c-KIT inhibitor in combination with a MAPKAP pathway inhibitor, include subjects with diseases and/or conditions that can be treated with a combination disclosed herein to achieve a beneficial therapeutic result, e.g., a mastocytosis, mast cell leukemia, or acute myeloid leukemia. A beneficial outcome in the treatment of mastocytosis may include a complete response, a partial response, a clinical improvement, or stable disease as defined by IWG-MRT-ECNM criteria (Gotlib et al, Blood 2013; 121: 2393-401). In certain embodiments, a subject in need of treatment is suffering from a cutaneous inastocytosis maculopapular cutaneous mastocytosis, mastocytorna, and diffuse cutaneous mastocytosis) or a systemic mastocytosis (e.g., indolent systemic mastocytosis, systemic smoldering mastocytosis, systemic mastocytosis with associated clonal. hematological non-mast cell lineage disease, aggressive systemic mastocytosis, mast cell leukemia and mast cell sarcoma). In particular embodiments, subjects are mammals, e.g., humans or other mammals.

The term "effective amount" when used in connection with a compound or other therapeutic agent disclosed herein, refers to an amount of the therapeutic agent, e.g., Compound A or a MAPKAP pathway inhibitor, alone or in combination, that is useful to treat or prevent a disease or disorder. The effective amount of therapeutic agents used in a combination therapy is the amount of each of the therapeutic agents that is useful for treating or preventing a disease or disorder when used in the combination therapy, even if the amount of one or both of the therapeutic agents, in the absence of the other therapeutic agent, is ineffective to treat or prevent the disease or disorder. In certain embodiments, an effective amount is a quantity that results in inducing cytocidal mast cell killing, inducing apoptosis of mast cells, reducing the amount of accumulated mast cells in a tissue or organ, reducing mastocytosis symptoms, inhibiting mast cell mediator release, inhibiting the growth of mast cells, and/or inducing mastocytosis regression wherein mast cells harbor activating mutations in c-KIT kinase including the activating c-KIT D816V mutation. The "effective amount" can vary depending upon the mode of administration, specific locus of the disease or disorder, and the age, body weight, and general health of the subject. The amount of the compounds administered will depend on the degree, severity, and type of the disease or condition, the amount of therapy desired, and the release characteristics of the pharmaceutical formulation(s). It will also depend on the subject's health, size, weight, age, sex and tolerance to drugs. Typically, the compounds are administered for a sufficient period of time to achieve the desired therapeutic effect.

The terms "treatment," "treat," and "treating," are meant to include the full spectrum of intervention in patients being treated, e.g., patients with a mastocytosis or acute myeloid leukemia (AML). Treating can be curing, improving, or at least partially ameliorating the disorder. In particular embodiments, treatment is performed with the intention to induce cytocidal mast cell killing, induce apoptosis of mast cells, reduce the amount of accumulated mast cells in a tissue or organ, reduce mastocytosis symptoms, inhibit mast cell mediator release, inhibit the growth of mast cells, and/or induce mastocytosis regression in the subject being treated. In certain embodiments, treatment with a combination therapy disclosed herein alleviates, slows or reverses one or more of the mastocytosis symptoms and/or induces regression of the mastocytosis, even if the mastocytosis is not actually eliminated. In some embodiments, treatment includes eliminating the disease or disorder, e.g., mastocytosis or AML, entirely. In other embodiments, treatment results in a complete response, a partial response, a clinical improvement, or stable disease as defined by IWG-MRT-ECNM criteria (Gotlib et al., Blood 2013; 121: 2393-401).

"Mast cells" as used herein, include mast cells (also called mastocytes) CD34-H mast cell precursor cells.

"Neoplasm" as used herein refers to an abnormal tissue that grows by cellular proliferation more rapidly than normal. Neoplasms show partial or complete lack of structural organization and functional coordination with the normal tissue, and usually form a distinct mass of tissue that may be either benign (benign tumor) or malignant (cancer).

"Tumor" as used herein refers to a mass. This is a term that may refer to benign (generally harmless) or malignant (cancerous) growths. Malignant growth can originate from a solid organ or the bone marrow. The latter is often referred to as liquid tumors. "Tumors" encompass mast cell leukemias and mast cell sarcomas, collectively referred to herein as "mastocytosis tumors."

In certain embodiments, the therapeutic effect of treating a mastocytosis according to the methods disclosed herein may be measured using standard response criteria known in the art. For example, "response criteria for complete remission (CR), partial remission (PR), clinical improvement (CI) or stable disease (SD)" used to quantitate the effects of therapy on aggressive systemic mastocytosis, mast cell leukemia, and systemic mastocytosis associated with a myeloid neoplasm may be any of those criteria defined by the IWG-MRT-ECNM (Gotlib et al, Blood 2013; 121: 2393-401). For example, Complete remission (CR) requires all 4 criteria and response duration must be≥12 wk, no presence of compact neoplastic mast cell aggregates in the BM or other biopsied extracutaneous organ. Serum tryptase level<20 ng/m14, peripheral blood count remission defined as ANC≥1×10$^9$/with normal differential, Hb level≥11 g/dL, and platelet count≥100×10$^9$/L, and complete resolution of palpable hepatosplenomegaly and all biopsy-proven or suspected SM-related organ damage (CI findings); Partial remission (PR)* requires all 3 criteria and response duration must be≥12 wk, in the absence of both CR and progressive disease (PD) with: reduction by≥50% in neoplastic MCs in the marrow and/or or other extracutaneous organ at biopsy demonstrating eligible SM-related organ damage, reduction of serum tryptase level by≥50%; and resolution of 1 or more biopsy-proven or suspected SM-related organ damage (CI finding(s)); clinical improvement (CI) is where response duration must be≥12 wk, requires 1 or more of the nonhematologic and/or hematologic response criteria to be fulfilled (see Table 3) in the absence of both CR/PR, and assignment or progressive disease (PD). Stable disease (SD) is not meeting criteria for CR, PR, CI, or PD.

Guidelines for adjudicating response include (1) Only disease-related≥grade 2 organ damage is evaluable as a primary endpoint in clinical trials. (2) Response adjudications of CR, PR, SD, PD, and loss or response (LOR) should only be applied to these ≥grade 2 organ damage findings in the context of trials. (3) Disease status at the time of patient removal from the study singularly relates to the updated status of initial≥grade 2 organ damage finding(s). (4) Exclusion of drug-related toxicity and/or other clinical issues (e.g., gastrointestinal tract bleeding in the case of worsening anemia/transfusion-dependence) should be undertaken before assigning the designation PD or LOR in a patient with worsening of baseline≥grade 2 organ damage.

In certain embodiments, the therapeutic effect of treating an AML according to the methods disclosed herein may be measured using standard response criteria known in the art.

For example, "response criteria for the treatment of AML" used to quantitate effects of therapy on AML may be any of those criteria defined below, including complete remission (CR) without minimal residual disease ($CR_{MRD-}$), Complete remission (CR), CR with incomplete hematologic recovery ($CR_i$), Morphologic leukemia-free state (MLFS), Partial remission (PR), stable disease (SD), or progressive disease (PD), as defined by Blood. 2017 Jan. 26; 129(4): 424-447, and summarized as: Complete Remission without minimal residual disease ($CR_{MRD-}$): If studied pretreatment, CR with negativity for a genetic marker by RT-qPCR, or CR with negativity by MFC; Complete remission (CR): Bone marrow blasts<5%; absence of circulating blasts and blasts with Auer rods; absence of extramedullary disease; absolute neutrophil count (ANC)≥$1.0 \times 10^9$/L [1000/µL]); platelet count≥$100 \times 10^9$/L [100 000/µL]); CR with incomplete hematologic recovery ($CR_i$): All CR criteria except for residual neutropenia (<$1.0 \times 10^9$/L [1000/µL]) or thrombocytopenia (<$100 \times 10^9$/L [100 000/µL]); Morphologic leukemia-free state (MLFS): Bone marrow blasts<5%; absence of blasts with Auer rods; absence of extramedullary disease; no hematologic recovery required; Partial remission (PR): All hematologic criteria of CR; decrease of bone marrow blast percentage to 5% to 25%; and decrease of pretreatment bone marrow blast percentage by at least 50%.

A "combination therapy" is a treatment that includes the administration of two or more therapeutic agents, e.g., a c-KIT inhibitor (such as Compound A or a pharmaceutically acceptable salt thereof, midostaurin, BLU-285, PLX9486, or crenolanib) and a MAPKAP pathway inhibitor (including but not limited to trametinib, cobimetinib, selumetinib, binimetinib, ulixertinib, LY3009120), to a patient. The two or more therapeutic agents may be delivered at the same time, e.g., in separate pharmaceutical compositions or in the same pharmaceutical composition, or they may be delivered at different times. For example, they may be delivered concurrently or during overlapping time periods, and/or one therapeutic agent may be delivered before or after the other therapeutic agent(s). Treatment with a combination of a KIT inhibitor such as Compound A and a MAPKAP pathway inhibitor optionally includes treatment with either single agent, preceded or followed by a period of concurrent treatment with both agents. However, it is contemplated that during some time period, effective amounts of the two or more therapeutic agents are present within the patient.

Methods of Treatment

In one embodiment, the present disclosure provides methods of treating or preventing a mastocytosis, optionally a c-KIT-mediated mastocytosis, e.g., a systemic mastocytosis (SM), comprising providing to or administering to a subject in need thereof an effective amount of a c-KIT inhibitor in combination with an effective amount of a MAPKAP pathway inhibitor, e.g., trametinib, cobimetinib, selumetinib, binimetinib, ulixertinib, or LY3009120. In one embodiment, the present disclosure provides methods of treating or preventing a mastocytosis, optionally a c-KIT-mediated mastocytosis, e.g., a systemic mastocytosis (SM), comprising providing to or administering to a subject in need thereof an effective amount of Compound A (or a pharmaceutically acceptable salt thereof) or Compound B (or a pharmaceutically acceptable salt thereof), in combination with an effective amount of a a MAPKAP pathway inhibitor, e.g., trametinib, cobimetinib, selumetinib, binimetinib, ulixertinib, or LY3009120. In a related embodiment, the present disclosure provides methods of treating or preventing a mastocytosis tumor, optionally a c-KIT-mediated mastocytosis tumor, e.g., a mast cell leukemia or mast cell sarcoma, comprising providing to or administering to a subject in need thereof an effective amount of a c-KIT inhibitor in combination with an effective amount of a a MAPKAP pathway inhibitor, e.g., trametinib, cobimetinib, selumetinib, binimetinib, ulixertinib, or LY3009120. In a related embodiment, the present disclosure provides methods of treating or preventing a mastocytosis tumor, optionally a c-KIT-mediated mastocytosis tumor, e.g., a mast cell leukemia or mast cell sarcoma, comprising providing to or administering to a subject in need thereof an effective amount of Compound A (or a pharmaceutically acceptable salt thereof) or Compound B (or a pharmaceutically acceptable salt thereof), in combination with an effective amount of a a MAPKAP pathway inhibitor, e.g., trametinib, cobimetinib, selumetinib, binimetinib, ulixertinib, or LY3009120.

In another example, the present disclosure provides a method of treating mastocytosis in a patient in need thereof, comprising administering to the patient: an effective amount of a c-KIT inhibitor; and an effective amount of one or more MAPKAP pathway inhibitors. Such a MAPKAP pathway inhibitor can be selected from the group consisting of a rapidly accelerated fibrosarcoma (RAF) kinase inhibitor, an inhibitor of a mitogen-activated protein kinase (MEK inhibitor), and an extracellular signal regulated kinase inhibitor (ERK inhibitor).

In one embodiment of such a disclosed method, the mastocytosis has a c-KIT mutation. In some embodiments, the c-KIT mutation is an activating mutation.

The mastocytosis may, in another embodiment, comprise mast cells having a primary mutation in exon 17 of a c-KIT gene. In some embodiments, the primary mutation is a c-KIT D816 mutation. In some embodiments, the primary mutation is one of D816V, D816Y, D816F, D816H, F522C, K5091, V560G, V559G, and del1419. In some embodiments, the primary mutation is D816V.

The mastocytosis may also comprise mast cells having a secondary c-KIT mutation. In some embodiments, the secondary c-KIT mutation is in one of exon 9, 11, 13 or 17. In some embodiments, the secondary c-KIT mutation is one of Y269C, Y503_F504insAY, V560D, or K642E mutation.

This disclosed method may further comprise determining if the mastocytosis has the c-KIT primary mutation. For example, the method further comprises determining if the mastocytosis has the c-KIT secondary mutation. In some embodiments, determining if the mastocytosis has the c-KIT primary or secondary mutation comprises identifying mutations in DNA extracted from a tumor sample. In yet another embodiment, determining if the mastocytosis has the c-KIT primary or secondary mutation comprises identifying mutations in circulating tumor DNA or from identifying mutations in circulating peripheral blood leukocytes.

The mastocytosis may be systemic mastocytosis. In some embodiments, the systemic mastocytosis is selected from the group consisting of indolent systemic mastocytosis, systemic smoldering mastocytosis, systemic mastocytosis with associated clonal hematological non-mast cell lineage disease, aggressive systemic mastocytosis, mast cell leukemia, and mast cell sarcoma. In some embodiments, the mastocytosis is indolent systemic mastocytosis, optionally systemic mastocytosis with recurrent anaphylaxis or vascular collapse in the absence of skin lesions. In some embodiments, the mastocytosis is systemic smoldering mastocytosis.

In some embodiments, the mastocytosis is systemic mastocytosis with associated clonal hematological non-mast cell lineage disease. In some embodiments, the mastocytosis is aggressive systemic mastocytosis. In some embodiments, the mastocytosis is mast cell leukemia or mast cell sarcoma. In some embodiments, the mastocytosis is cutaneous mastocytosis. In some embodiments, the mastocytosis is selected from the group consisting of: maculopapular cutaneous mastocytosis, mastocytoma, or diffuse cutaneous mastocytosis.

In such a disclosed method, the c-KIT inhibitor can be selected from the group consisting of 1-[4-bromo-5-[1-ethyl-7-(methylamino)-2-oxo-1,2-dihydro-1,6-naphthyridin-3-yl]-2-fluorophenyl]-3-phenylurea or a pharmaceutically acceptable salt thereof, midostaurin or a pharmaceutically acceptable salt thereof, imatinib mesylate, sunitinab malate, midostaurin, regorafenib, crenolanib, PTX9486, or BLU-285 (avapritinib) or a pharmaceutically acceptable salt thereof.

Furthermore, the MEK inhibitor can be selected from the group consisting of trametinib, selumetinib, cobimetinib, and binimetinib. In some embodiments, the MEK inhibitor is binimetinib. In some embodiments, the MEK inhibitor is trametinib. In some embodiments, the ERK inhibitor is selected from the group consisting of ulixertinib, SCH772984, and LY3214996. In some embodiments, the c-KIT inhibitor and the MEK and/or ERK inhibitor are administered substantially concurrently or sequentially.

The method may also comprise administering another cancer-targeted therapeutic agent, cancer-targeted biological, immune checkpoint inhibitor, or chemotherapeutic agent.

Additionally, two weeks or more of administration of an effective amount of a c-KIT inhibitor; and an effective amount of an inhibitor of a mitogen-activated protein kinase (MEK inhibitor), and/or an effective amount of an extracellular signal regulated kinase inhibitor (ERK inhibitor) in accordance with the contemplated method can result in the patient having at least a partial remission.

Also provided is a method of treating a systemic mastocytosis in a patient in need thereof, comprising administering to the patient: an effective amount of 1-[4-bromo-5-[1-ethyl-7-(methylamino)-2-oxo-1,2-dihydro-1,6-naphthyridin-3-yl]- 2-fluorophenyl]-3-phenylurea, or a pharmaceutically acceptable salt thereof; and an effective amount of a MAPKAP pathway inhibitor. In such a disclosed method, the MAPKAP pathway inhibitor is selected from the group consisting of rapidly accelerated fibrosarcoma (RAF) kinase inhibitor, an inhibitor of a mitogen-activated protein kinase (MEK inhibitor) and an extracellular signal regulated kinase inhibitor (ERK inhibitor).

The systemic mastocytosis can, in an embodiment, have a c-KIT mutation. For example, the mutation can be a c-KIT D816 mutation. In some embodiments, the mutation is one of D816V, D816Y, D816F, D816H, F522C, K509I, V560G, V559G, and del419. In some embodiments, the mutation is one of: A553D, C433Y, D419Y, D572A, D816F, D816H, D816I, D816V, D816Y, D820G, del419, dup(501-502), E839K, F522C, I817V, InsFF419, InsV815-I816, K509I, N822I, R815K, T417V, V560G, V559I or Y418Y. In some embodiments, the mutation is D816V.

In addition, the mastocytosis may have a further c-KIT mutation that is one of Y269C, Y503_F504insAY, V560D, or K642E mutation.

In such a disclosed method, the MEK inhibitor can be selected from the group consisting of trametinib, selumetinib, cobimetinib, and binimetinib. In some embodiments, the MEK inhibitor is binimetinib. In some embodiments, the MEK inhibitor is trametinib. The ERK inhibitor can be selected from the group consisting of ulixertinib, SCH772984, and LY3214996.

The present disclosure additionally provides a method of treating mastocytosis in a patient in need thereof, comprising administering to the patient: an effective amount of a c-KIT inhibitor; and an effective amount of a RAF inhibitor.

In such a disclosed method, the RAF inhibitor can be a pan-RAF or B-RAF inhibitor including vemurafenib, dabrafenib, and LY3009120. Furthermore, the c-KIT inhibitor can be 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof.

In specific embodiments of methods disclosed herein, including methods of treating a mastocytosis or a mastocytosis tumor, the methods include: induction of cytocidal mast cell killing, induction of apoptosis of mast cells, reduction of the amount of accumulated mast cells in a tissue or organ, reduction of mastocytosis symptoms, inhibition of mast cell mediator release, inhibition of the growth of mast cells, and/or induction of mastocytosis regression, wherein the mast cells harbor one or more activating mutations in c-KIT kinase, such as, e.g., the activating KIT D816V mutation. In certain embodiments, the methods encompass methods for eradicating a mastocytosis, e.g., a mastocytosis tumor, in a subject. In some embodiments, treatment results in a complete response, a partial response, a clinical improvement, or stable disease as defined by IWG-MRT-ECNM criteria (Gotlib et al, Blood 2013; 121: 2393-401).

In another related embodiment, the present disclosure provides methods of treating or preventing an acute myeloid leukemia (AML), optionally a c-KIT-mediated (AML), comprising administering to a subject in need thereof an effective amount of a c-KIT inhibitor in combination with an effective amount of a a MAPKAP pathway inhibitor, e.g., trametinib, cobimetinib, selumetinib, binimetinib, ulixertinib, or LY3009120. In a related embodiment, the present disclosure provides methods of treating or preventing an acute myeloid leukemia (AML), optionally a c-KIT-mediated (AML), comprising administering to a subject in need thereof an effective amount of Compound A (or a pharmaceutically acceptable salt thereof) or Compound B (or a pharmaceutically acceptable salt thereof), in combination with an effective amount of a a MAPKAP pathway inhibitor, e.g., trametinib, cobimetinib, selumetinib, binimetinib, ulixertinib, or LY3009120.

Where the methods described herein refer to treatment with Compound A or a pharmaceutically acceptable salt thereof, or with Compound B or a pharmaceutically acceptable salt thereof, it is meant that only one of Compound A or a pharmaceutically acceptable salt thereof, or Compound B or a pharmaceutically acceptable salt thereof is required. However, it is understood that these methods also encompass administering to a patient both Compound A or a pharmaceutically acceptable salt thereof, and Compound B or a pharmaceutically acceptable salt thereof, in combination with a MAPKAP pathway inhibitor. The methods described herein also encompass administration of Compound A and a MAPKAP pathway inhibitor to a subject whereupon Compound A is metabolized in vivo to Compound B, and the in vivo mixture of Compound A and Compound B effectively treats a subject in combination with the MAPKAP pathway inhibitor.

Particular embodiments of the disclosed methods and compositions are practiced using: a combination of Compound A or a pharmaceutically acceptable salt thereof and trametinib; a combination of Compound A or a pharmaceutically acceptable salt thereof and selumetinib; a combination of Compound A or a pharmaceutically acceptable salt thereof and cobimetinib; or a combination of Compound A or a pharmaceutically acceptable salt thereof and binimetinib.

In one embodiment, Compound A or a pharmaceutically acceptable salt thereof and a MEK inhibitor, e.g., trametinib or binimetinib, are administered to a subject with a c-KIT-mediated mastocytosis. In another embodiment, Compound B or a pharmaceutically acceptable salt thereof and a MEK inhibitor, e.g., trametinib or binimetinib, are administered to a subject with a c-KIT-mediated mastocytosis.

In a related embodiment, Compound A or a pharmaceutically acceptable salt thereof and a MEK inhibitor, e.g., trametinib or binimetinib, are administered to a patient with a mastocytosis tumor, including but not limited to mast cell leukemia or a mast cell sarcoma, wherein mastocytosis tumor growth or tumor progression is caused by a primary activating c-KIT mutation, e.g., the KIT D816V mutation. In another embodiment, Compound B or a pharmaceutically acceptable salt thereof and a MEK inhibitor, e.g., trametinib or binimetinib, are administered to a patient with a mastocytosis tumor, including but not limited to mast cell leukemia or a mast cell sarcoma, wherein mastocytosis tumor growth or tumor progression is caused by a primary activating c-KIT mutation, e.g., the KIT D816V mutation. In certain embodiments, Compound A or a pharmaceutically acceptable salt thereof, or Compound B or a pharmaceutically acceptable salt thereof and a MEK inhibitor, e.g., trametinib or binimetinib, are administered to a patient with AML, optionally wherein the AML is caused by a primary activating c-KIT mutation, e.g., a c-KIT exon 8 activating mutation, or a c-KIT exon 17 mutation, including but not limited to mutations at D816 or at N822 (Journal of Clinical Oncology 2006 24:24, 3904-3911).

Particular embodiments of the disclosed methods and compositions are practiced using: a combination of Compound A or a pharmaceutically acceptable salt thereof and ulixertinib; a combination of Compound A or a pharmaceutically acceptable salt thereof and SCH772984, e; a combination of Compound A or a pharmaceutically acceptable salt thereof and LY3214996; a combination of Compound A or a pharmaceutically acceptable salt thereof and ravoxertinib, or a combination of Compound A or a pharmaceutically acceptable salt thereof and and VX-11.

In one embodiment, Compound A or a pharmaceutically acceptable salt thereof and an ERK inhibitor, e.g., ulixertinib, are administered to a subject with a c-KIT-mediated mastocytosis. In another embodiment, Compound B or a pharmaceutically acceptable salt thereof and an ERK inhibitor, e.g., ulixertinib, are administered to a subject with a c-KIT-mediated mastocytosis.

In a related embodiment, Compound A or a pharmaceutically acceptable salt thereof and an ERK inhibitor, e.g., ulixertinib, are administered to a patient with a mastocytosis tumor, including but not limited to mast cell leukemia or a mast cell sarcoma, wherein mastocytosis tumor growth or tumor progression is caused by a primary activating c-KIT mutation, e.g., the KIT D816V mutation. In another embodiment, Compound B or a pharmaceutically acceptable salt thereof and an ERK inhibitor, e.g., ulixertinib, are administered to a patient with a mastocytosis tumor, including but not limited to mast cell leukemia or a mast cell sarcoma, wherein mastocytosis tumor growth or tumor progression is caused by a primary activating c-KIT mutation, e.g., the KIT D816V mutation. In certain embodiments, Compound A or a pharmaceutically acceptable salt thereof, or Compound B or a pharmaceutically acceptable salt thereof and an ERK inhibitor, e.g., ulixertinib, are administered to a patient with AML, optionally wherein the AML is caused by a primary activating c-KIT mutation, e.g., a c-KIT exon 8 activating mutation, or a c-KIT exon 17 mutation, including but not limited to mutations at D816 or at N822 (Journal of Clinical Oncology 2006 24:24, 3904-3911).

Particular embodiments of the disclosed methods and compositions are practiced using: a combination of Compound A or a pharmaceutically acceptable salt thereof and LY3009120; a combination of Compound A or a pharmaceutically acceptable salt thereof and dabrafenib; or a combination of Compound A or a pharmaceutically acceptable salt thereof and vemurafenib.

In one embodiment, Compound A or a pharmaceutically acceptable salt thereof and a RAF inhibitor, e.g., LY3009120, dabrafenib, or vemurafenib, are administered to a subject with a c-KIT-mediated mastocytosis. In another embodiment, Compound B or a pharmaceutically acceptable salt thereof and a RAF inhibitor, e.g., LY3009120, dabrafenib, or vemurafenib, are administered to a subject with a c-KIT-mediated mastocytosis. In a related embodiment, Compound A or a pharmaceutically acceptable salt thereof and a RAF inhibitor, e.g., LY3009120, dabrafenib, or vemurafenib, are administered to a patient with a mastocytosis tumor, including but not limited to mast cell leukemia or a mast cell sarcoma, wherein mastocytosis tumor growth or tumor progression is caused by a primary activating c-KIT mutation, e.g., the KIT D816V mutation. In another embodiment, Compound B or a pharmaceutically acceptable salt thereof and a RAF inhibitor, e.g., LY3009120, dabrafenib, or vemurafenib, are administered to a patient with a mastocytosis tumor, including but not limited to mast cell leukemia or a mast cell sarcoma, wherein mastocytosis tumor growth or tumor progression is caused by a primary activating c-KIT mutation, e.g., the KIT D816V mutation. In certain embodiments, Compound A or a pharmaceutically acceptable salt thereof, or Compound B or a pharmaceutically acceptable salt thereof and a RAF inhibitor, e.g., LY3009120, dabrafenib, or vemurafenib, are administered to a patient with AML, optionally wherein the AML is caused by a primary activating c-KIT mutation, e.g., a c-KIT exon 8 activating mutation, or a c-KIT exon 17 mutation, including but not limited to mutations at D816 or at N822 (Journal of Clinical Oncology 2006 24:24, 3904-3911).

Illustrative c-KIT inhibitors that may be used according to the disclosed methods and compositions include, but are not limited to, Compound A or a pharmaceutically acceptable salt there, Compound B or a pharmaceutically acceptable salt thereof, midostaurin, BLU-285, PLX9486, and crenolanib. Illustrative MEK inhibitors that may be used according to the disclosed methods and compositions include, but are not limited to, trametinib, selumetinib, cobimetinib, and binimetinib. Illustrative ERK inhibitors that may be used according to the disclosed methods and compositions include, but are not limited to, ulixertinib, SCH772984, LY3214996, ravoxertinib, and VX-11e. Illustrative RAF inhibitors that may be used according to the disclosed methods and compositions include, but are not limited to, LY3009120, dabrafenib, and vemurafenib.

Treatment with Compound A or a pharmaceutically acceptable salt thereof, or Compound B or a pharmaceutically acceptable salt thereof, in combination with a MAPKAP pathway inhibitor, e.g., trametinib, binimetinib, ulixertinib, or LY3009120, encompasses administering Compound A or a pharmaceutically acceptable salt thereof, or Compound B or a pharmaceutically acceptable salt thereof, before, after, simultaneous with, or during an overlapping time period with administering the MAPKAP pathway inhibitor. It is understood that an effective amount of any of Compound A or a pharmaceutically acceptable salt thereof, Compound B or a pharmaceutically acceptable salt thereof, another c-KIT inhibitor, or a MAPKAP pathway inhibitor, e.g., trametinib, binimetinib, ulixertinib, or LY3009120, may be different when used in the combinations disclosed herein as compared to when any of these agents is used by itself for the same purpose, e.g., to treat or prevent mastocytosis or a mast cell tumor, e.g., a mast cell leukemia or AML. In particular embodiments, an effective amount of Compound A or a pharmaceutically acceptable salt thereof, or of Compound B or a pharmaceutically acceptable salt thereof, is a lower amount when administered as a combination therapy with a MAPKAP pathway inhibitor, e.g., trametinib, binimetinib, ulixertinib, or LY3009120, as compared to when it is administered as a monotherapy, e.g., to treat or prevent a mastocytosis or a mast cell tumor. In particular embodiments, an effective amount of a MAPKAP pathway inhibitor, e.g., trametinib, binimetinib, ulixertinib, or LY3009120, is a lower amount when administered in a combination therapy with Compound A or a pharmaceutically acceptable salt thereof, or when administered in a combination therapy with Compound B or a pharmaceutically acceptable salt thereof, e.g., to treat or prevent a mastocytosis or a mast cell tumor.

Any of the methods disclosed herein may further include determining that the mastocytosis cells, mast cell tumor, or AML being treated has one or more c-KIT gene mutations. Such a determination may be made by routine methods for determining the presence of a gene mutation in a biological sample, e.g., a bone marrow sample, a tissue sample, a peripheral blood sample, or a plasma sample, obtained from the subject. In addition, such a determination may be made by reviewing the results of tests performed to determine the presence of one or more c-KIT gene mutations in the biological sample obtained from the patient. In certain embodiments of any of the methods disclosed herein, the methods are performed on subjects wherein the mastocytosis, mast cell tumor, or AML has been identified as having one or more c-KIT gene mutations. The c-KIT gene mutations include but not limited to any of those specifically described herein. In certain embodiments of any of the methods disclosed herein, the methods are not performed on subjects wherein the mastocytosis, mast cell tumor, or AML has been identified as not having one or more c-KIT gene mutations.

In various aspects of any of the methods disclosed herein, treatment with either Compound A or a pharmaceutically acceptable salt thereof, or Compound B or a pharmaceutically acceptable salt thereof, in combination with a MAPKAP pathway inhibitor, e.g., trametinib, binimetinib, ulixertinib, or LY3009120, induces cytocidal mast cell killing, induces apoptosis of mast cells, reduces the amount of accumulated mast cells in a tissue or organ, reduces mastocytosis symptoms, inhibits mast cell mediator release, inhibits the growth of mast cells, and/or induces mastocytosis regression wherein mast cells harbor activating mutations in c-KIT kinase including the activating KIT D816V mutation. Methods for measuring or determining amounts of apoptosis of mast cells, mast cell killing, inhibition of mast cell growth and proliferation, inhibition of mast cell mediator release, peripheral blood mutant KIT allele burden, eradication of mastocytosis and mastocytosis tumors, complete response, partial response, clinical improvement, or stable disease are known in the art and include any methods described herein.

In particular embodiments, treatment with a combination of: a c-KIT inhibitor, e.g., Compound A or a pharmaceutically acceptable salt thereof, or Compound B or a pharmaceutically acceptable salt thereof; and a MAPKAP pathway inhibitor, e.g., trametinib, binimetinib, ulixertinib, or LY3009120, results in an increased amount of apoptosis of mastocytosis cells or mast cells, as compared to the amount of apoptosis of mastocytosis cells or mast cells of the same type either untreated or treated with only a MAPKAP pathway inhibitor, or with only a c-KIT inhibitor, e.g., Compound A or Compound B. For example, apoptosis may be increased by at least 10%, at least 20%, at least 30%, at least 40%, at least 50%, at least 60%, at least 70%, at least 80%, at least 90%, at least two-fold, at least three-fold, at least four-fold, at least five-fold, at least 10-fold, or at least 20-fold. In certain embodiments, amounts of apoptosis are determined by measuring caspase activity of KIT mutant mast cells or mast cell lines including the HMC1.2 mast cell line harboring the KIT D816V mutation.

In particular embodiments, treatment with a combination of: a c-KIT unhibitor, e.g., Compound A or a pharmaceutically acceptable salt thereof, or Compound B or a pharmaceutically acceptable salt thereof; and a MAPKAP pathway inhibitor, e.g., trametinib, binimetinib, ulixertinib, or LY3009120, results in a decreased accumulation of mast cells in skin or an internal organ, e.g., liver, spleen, bone marrow, and/or small intestine, as compared to the amount of accumulation of mast cells in the same organ either untreated or treated with only a MAPKAP pathway inhibitor, e.g., trametinib, binimetinib, ulixertinib, or LY3009120, or with only a c-KIT inhibitor, e.g., midostaurin, BLU-285, Compound A or Compound B. For example, the amount or number of mast cells accumulated within the organ may be decreased by at least 10%, at least 20%, at least 30%, at least 40%, at least 50%, at least 60%, at least 70%, at least 80%, or at least 90%.

In particular embodiments, treatment with a combination of: a c-KIT inhibitor, e.g., Compound A or a pharmaceutically acceptable salt thereof, or Compound B or a pharmaceutically acceptable salt thereof; and a MAPKAP pathway inhibitor, e.g., trametinib, binimetinib, ulixertinib, or LY3009120, results in a complete response as defined by as defined by IWG-MRT-ECNM criteria (Gotlib et al, Blood 2013; 121: 2393-401).

In particular embodiments, treatment with a combination of: a c-KIT inhibitor, e.g., Compound A or a pharmaceutically acceptable salt thereof, or Compound B or a pharmaceutically acceptable salt thereof; and a MAPKAP pathway inhibitor, e.g., trametinib, binimetinib, ulixertinib, or LY3009120, results in a partial response as defined by as defined by IWG-MRT-ECNM criteria (Gotlib et al, Blood 2013; 121: 2393-401).

In particular embodiments, treatment with a combination of: a c-KIT inhibitor, e.g., Compound A or a pharmaceutically acceptable salt thereof, or Compound B or a pharmaceutically acceptable salt thereof; and a MAPKAP pathway inhibitor, e.g., trametinib, binimetinib, ulixertinib, or LY3009120, results in clinical improvement as defined by as defined by IWG-MRT-ECNM criteria (Gotlib et al, Blood 2013; 121: 2393-401).

In particular embodiments, treatment with a combination of: a c-KIT inhibitor, e.g., Compound A or a pharmaceutically acceptable salt thereof, or Compound B or a pharmaceutically acceptable salt thereof; and a MAPKAP pathway inhibitor, e.g., trametinib, binimetinib, ulixertinib, or LY3009120, results in stable disease as defined by as defined by IWG-MRT-ECNM criteria (Gotlib et al, Blood 2013; 121: 2393-401).

In particular embodiments, treatment with a combination of: a c-KIT inhibitor, e.g., Compound A or a pharmaceutically acceptable salt thereof, or Compound B or a pharmaceutically acceptable salt thereof; and a MAPKAP pathway inhibitor, e.g., trametinib, binimetinib, ulixertinib, or LY3009120, induces apoptosis or inhibits the growth of resistant mastocytosis cells containing a secondary KIT mutation in addition to the KIT D816V primary mutation wherein the secondary KIT mutation includes but is not limited to Y269C, Y503_F504insAY, V560D, or K642E point mutation, an in-frame deletion or insertion, or a missense mutation in the c-KIT gene (Lasho et al, Br J Haematol 173, 153-156).

In particular embodiments, treatment with a combination of: a c-KIT inhibitor, e.g., Compound A or a pharmaceutically acceptable salt thereof, or Compound B or a pharmaceutically acceptable salt thereof; and a MAPKAP pathway inhibitor, e.g., trametinib, binimetinib, ulixertinib, or LY3009120, induces apoptosis or inhibits the growth of resistant mastocytosis cells containing mutations, e.g., resistance mutations, in other genes, including any of those disclosed herein. In certain embodiments, such other gene mutations may include NRas gain of function mutations (Haematologica 2011;96(03):459-463.doi:10.3324/haematol.2010.031690) or TET2 loss of function mutations (Leukemia 2009;23:900-04; Blood, 6 Dec. 2012; 120 (24): 4846-49). The presence of other epigenetic or transcriptional regulator mutations have been detected in SM, including DNMT3A, ASXL1 and CBL mutations in 12%, 12% and 4% of patients, respectively (PloS one. 2012;7:e43090). Additionally, some mastocytosis patients also present with mutations in the spliceosome machinery. Spliceosomes ensure the correct linear order of exons spliced in mRNAs. Hanssens et al. reported 23.6% SRSF2, 5.6% SF3B1 and 2.7% U2AF1 incidence of mutations in a group of 72 mastocytosis patients (Haematologica 2014; 99:830-35). Such mastocytoses having complex genomic drivers may benefit from a treatment disclosed herein with a combination of a c-KIT inhibitor and a MEK inhibitor as compared to no treatment or treatment with only a MEK inhibitor, e.g., trametinib, or with only a c-KIT inhibitor, e.g., Compound A or Compound B. For example, apoptosis may be increased by at least 10%, at least 20%, at least 30%, at least 40%, at least 50%, at least 60%, at least 70%, at least 80%, at least 90%, at least two-fold, at least three-fold, at least four-fold, at least five-fold, at least 10-fold, or at least 20-fold. For example, the amount of growth or number of resistant mastocytosis cells may be inhibited by at least 10%, at least 20%, at least 30%, at least 40%, at least 50%, at least 60%, at least 70%, at least 80%, or at least 90%.

In particular embodiments, resistant mastocytosis cells are resistant to apoptosis-mediated cell death or cytocidal activity by treatment with a c-KIT inhibitor, e.g., Compound A, Compound B, midostaurin, BLU-285, PLX9486, or crenolanib, and/or are resistant to apoptosis-mediated cell death or cytocidal activity by treatment with a MAPKAP pathway inhibitor, e.g., trametinib, binimetinib, ulixertinib, or LY3009120, when used as single agent therapies.

In particular embodiments, treatment with a combination of: a c-KIT inhibitor, e.g., either Compound A or a pharmaceutically acceptable salt thereof, or Compound B or a pharmaceutically acceptable salt thereof; in combination with a MAPKAP pathway inhibitor, e.g., trametinib, binimetinib, ulixertinib, or LY3009120, results in eradication of a mastocytosis, e.g., a matocytosis tumor. In particular embodiments, eradication of a mastocytosis means there is no longer any detectable mastocytosis in the patient. In particular embodiments, there is no detectable mastocytosis in the patient for at least twelve weeks, at least twenty-four weeks, at least one year, at least two years, or at least 5 years after initiation of treatment of the mastocytosis by a combination therapy disclosed herein. Eradication of mastocytosis may be determined by criteria for complete response as defined by IWG-MRT-ECNM criteria (Gotlib et al, Blood 2013; 121: 2393-401).

The present disclosure describes combination therapies that involve the administration of a c-KIT inhibitor, e.g., either Compound A or a pharmaceutically acceptable salt thereof, or Compound B or a pharmaceutically acceptable salt thereof, and a MAPKAP pathway inhibitor, e.g., trametinib, binimetinib, ulixertinib, or LY3009120. The combination therapies described herein can be used by themselves, or in combination with one or more additional therapeutic agents. For example, either Compound A or a pharmaceutically acceptable salt thereof or Compound B or a pharmaceutically acceptable salt thereof, and a MAPKAP pathway inhibitor, can be administered together with a cancer targeted therapeutic agent, a cancer-targeted biologic, an immune checkpoint inhibitor, or a chemotherapeutic agent. In another embodiment, Compound A or Compound B and a MAPKAP pathway inhibitor, e.g., trametinib, binimetinib, ulixertinib, or LY3009120are administered without any other therapeutic agent. The therapeutic agents can be administered together with or sequentially with another therapeutic agent described herein in a combination therapy.

Combination therapy can be achieved by administering two or more therapeutic agents, each of which is formulated and administered separately, or by administering two or more therapeutic agents in a single formulation. Other combinations are also encompassed by combination therapy. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or weeks of each other. In some cases even longer intervals are possible. While in many cases it is desirable that the two or more agents used in a combination therapy be present in within the patient's body at the same time, this need not be so.

Combination therapy can also include two or more administrations of one or more of the agents used in the combination using different sequencing of the component agents. For example, if agent X and agent Y are used in a combination, one could administer them sequentially in any combination one or more times, e.g., in the order X-Y-X, X-X-Y, Y-X-Y, Y-Y-X, X-X-Y-Y, etc. Furthermore, administration of two or more agents of the combination may precede or follow administration dosing intervals during which at least one of the combination agents is omitted from the treatment.

Additional therapeutic agents that may be administered according to the present disclosure, e.g., to treat a mastocytosis or mastocytosis tumor, include, but are not limited to, agents selected from the group consisting of: inhibitors of STATS, including but not limited to ruxolitinib, tofacitinib, or fedratinib; inhibitors of BTK including but not limited to ibrutinib, PCI 29732, acalabrutinib, or AVL-292; inhibitors of PI3 kinase including but not limited to idelalisib, dactolisib, pictilisib, LY294002, buparlisib, pilaralisib, duvelisib, PF-04691502, voxtalisib, omipalisib, gedatolisib, apitolisib, or wortmannin; inhibitors of AKT kinase including but not limited to MK-2206, perifosine, GSK690693, GSK2141795, ipatasertib, AZD5363, afuresertib, or AT7867; inhibitors of DNA methylation including but not limited to 5-azacytidine or 5-aza-2'-deoxycytidine; proteosomal inhibitors including but not limited to bortezomib, carfilzomib, MLN9708, ONX 0912; interferon-alpha (IFN-α); cladribine; and lysosomotropic agents including but not limited to chloroquine, hydroxychloroquine, or quinacrine.

In certain embodiments, the additional therapeutic agent s selected from 5-azacytidine, 5-aza-2'-deoxycytidine, and cladribine.

In particular embodiments, a subject in need thereof is treated with a combination of Compound A or a pharmaceutically acceptable salt thereof, one or two of a MAPKAP pathway inhibitor, e.g., trametinib, binimetinib, ulixertinib, or LY3009120, and 5-azacytidine. In certain embodiments, the MAPKAP pathway inhibitor is trametinib. In certain embodiments, the MAPKAP pathway inhibitor is binimetinib. In certain embodiments, the MAPKAP pathway inhibitor is ulixertinib. In certain embodiments, the MAPKAP pathway inhibitor is LY3009120, dabrafenib or vemurafenib.

In particular embodiments, a subject in need thereof is treated with a combination of Compound A or a pharmaceutically acceptable salt thereof, a MAPKAP pathway inhibitor, e.g., trametinib, binimetinib, ulixertinib, or LY3009120, and 5-aza-2'-deoxycytidine. In certain embodiments, the MAPKAP pathway inhibitor is trametinib. In certain embodiments, the MAPKAP pathway inhibitor is binimetinib. In certain embodiments, the MAPKAP pathway inhibitor is ulixertinib. In certain embodiments, the MAPKAP pathway inhibitor is LY3009120, dabrafenib or vemurafenib.

In particular embodiments, a subject in need thereof is treated with a combination of Compound A or a pharmaceutically acceptable salt thereof, MAPKAP pathway inhibitor, e.g., trametinib, binimetinib, ulixertinib, or LY3009120, and cladribine. In certain embodiments, the MAPKAP pathway inhibitor is trametinib. In certain embodiments, the MAPKAP pathway inhibitor is binimetinib. In certain embodiments, the MAPKAP pathway inhibitor is ulixertinib. In certain embodiments, the MAPKAP pathway inhibitor is LY3009120, dabrafenib or vemurafenib. Additional therapeutic agents that may be administered according to the present disclosure include, but are not limited to, arsenic trioxide, cyclophosphamide, cytarabine, daunorubicin, doxorubicin, enasidenib, idarubicin, quizartinib, mitoxantrone, thioguanine, or vincristine. In particular embodiments, a subject having AML is treated with a combination of Compound A or a pharmaceutically acceptable salt thereof, and arsenic trioxide, cyclophosphamide, cytarabine, daunorubicin, doxorubicin, enasidenib, idarubicin, quizartinib, mitoxantrone, thioguanine, or vincristine.

Pharmaceutical Compositions

Aspects of the present disclosure are directed to methods of treatment involving the administration of a combination of compounds disclosed herein, or one or more pharmaceutical compositions comprising such compounds and a pharmaceutically acceptable diluent, excipient or carrier. In particular embodiments, the methods disclosed herein involve administering a first pharmaceutical composition comprising a c-KIT inhibitor, e.g., Compound A or a pharmaceutically acceptable salt thereof and a pharmaceutically acceptable diluent, excipient or carrier, and a second pharmaceutical composition comprising a MAPKAP pathway inhibitor, e.g., trametinib, binimetinib, ulixertinib, or LY3009120, and a pharmaceutically acceptable diluent, excipient or carrier. In particular embodiments, the methods disclosed herein involve administering a first pharmaceutical composition comprising Compound B or a pharmaceutically acceptable salt thereof and a pharmaceutically acceptable diluent, excipient or carrier, and a second pharmaceutical composition comprising a MAPKAP pathway inhibitor, e.g., trametinib, binimetinib, ulixertinib, or LY3009120, and a pharmaceutically acceptable diluent, excipient or carrier. In particular embodiments, the methods disclosed herein involve administering a pharmaceutical composition comprising a ciKIT inhibitor, e.g., Compound A or a pharmaceutically acceptable salt thereof, a MAPKAP pathway inhibitor, e.g., trametinib, binimetinib, ulixertinib, or LY3009120, and a pharmaceutically acceptable diluent, excipient or carrier. In particular embodiments, the methods disclosed herein involve administering a pharmaceutical composition comprising Compound B or a pharmaceutically acceptable salt thereof, a MAPKAP pathway inhibitor, e.g., trametinib, binimetinib, ulixertinib, or LY3009120, and a pharmaceutically acceptable diluent, excipient or carrier.

In using the pharmaceutical compositions of the compounds described herein, pharmaceutically acceptable carriers can be either solid or liquid. Solid forms include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa., which is hereby incorporated by reference in its entirety.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intranasal administration.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations suitable for inhalation may also be used. These preparations may include solutions and solids in powder form, which may be in combination with a pharmaceutically acceptable carrier, such as an inert compressed gas, e.g., nitrogen.

Also contemplated for use are solid form preparations that are intended to be converted, shortly before use, to liquid form preparations for either oral or parenteral administration. Such liquid forms include solutions, suspensions and emulsions.

Dosage

In some embodiments where Compound A or Compound B (or pharmaceutically acceptable salts thereof) is used in combination with a MAPKAP pathway inhibitor, e.g., trametinib, binimetinib, ulixertinib, or LY3009120for a treatment protocol, the two therapeutics may be administered together or in a "dual-regimen" wherein the two therapeutics are dosed and administered separately. When the Compound A or B (or pharmaceutically acceptable salts thereof) and the MAPKAP pathway inhibitor are dosed separately, the typical dosage of Compound A or Compound B (or pharmaceutically acceptable salts thereof) administered to the subject in need of the treatment is typically from about 5 mg per day to about 5000 mg per day and, in other embodiments, from about 50 mg per day to about 1000 mg per day. Other dosages may be from about 10 mmol up to about 250 mmol per day, from about 20 mmol to about 70 mmol per day or even from about 30 mmol to about 60 mmol per day. Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. A typical recommended daily dosage regimen for oral administration can range from about 1 mg/day to about 500 mg/day or 1 mg/day to 200 mg/day, in a single dose, or in two to four divided doses. In one embodiment, the typical daily oral dose regimen is 150 mg.

In certain embodiments, the dosage of MAPKAP pathway inhibitors is consistent with previously disclosed dosages and/or dosages approved for use by the Food and Drug Administration. In other embodiments, the dosage of the MAPKAP pathway inhibitor is less than previously approved dosages, e.g., about 20%, about 50% or about 80% of an approved dosage. In certain embodiments, the dosage of trametinib is about 0.05 mg to 20 mg orally daily, e.g., about 1 mg daily or about 2 mg daily. In certain embodiments, the dosage of cobimetinib is about 10 mg to 200 mg daily, e.g., about 30 mg or about 60 mg daily. In certain embodiments, the dosage of binimetinib is about 10 mg to about 200 mg twice daily, e.g., about 25 mg or about 45 mg twice daily. In certain embodiments, the dosage of selumetinib is about 10 mg to about 200 mg daily, or about 30 mg or about 75 mg twice daily.

The amount and frequency of administration of the compounds described herein and/or the pharmaceutically acceptable salts thereof, and other therapeutic agents, will be regulated according to the judgment of the attending clinician considering such factors as age, condition and size of the patient as well as severity of the symptoms being treated.

Compounds of the present disclosure (e.g., Compound A or Compound B (and pharmaceutically acceptable salts thereof), MAPKAP pathway inhibitors, and other therapeutic agents) may be administered by any suitable route. The compounds can be administrated orally (e.g., dietary) in capsules, suspensions, tablets, pills, dragees, liquids, gels, syrups, slurries, and the like. Methods for encapsulating compositions (such as in a coating of hard gelatin or cyclodextran) are known in the art (Baker, et al., "Controlled Release of Biological Active Agents", John Wiley and Sons, 1986, which is hereby incorporated by reference in its entirety). The compounds can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers are biocompatible, i.e., non-toxic, non-inflammatory, non-immunogenic and devoid of other undesired reactions at the administration site.

Illustrative pharmaceutical compositions are tablets and gelatin capsules comprising a Compound described herein, e.g., Compound A or a pharmacetucially acceptable salt thereof, and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

If formulated as a fixed dose, such combination products employ the compounds described herein within the dosage range described herein, or as known to those skilled in the art.

Since the compounds described herein (e.g., Compounds A and B and MAPKAP pathway inhibitors) are intended for use in pharmaceutical compositions a skilled artisan will understand that they can be provided in substantially pure forms for example, at least 60% pure, at least 75% pure, at least 85% pure, and at least 98% pure (w/w). The pharmaceutical preparation may be in a unit dosage form. In such form, the preparation is subdivided into suitably sized unit doses containing appropriate quantities of compounds A or B, e.g., an effective amount to achieve the desired purpose as described herein.

EXAMPLES

It has been found that treatment with a combination of either Compound A or a pharmaceutically acceptable salt thereof in combination with a MAPKAP pathway inhibitor unexpectedly and synergistically induce apoptosis of mutant c-KIT-driven mast cells causative of systemic mastocytosis. In addition, this combination therapy inhibits proliferation of mastocytosis cells. Furthermore, the combination therapy disclosed herein appeared to have a cytotoxic effect on mastocytosis, as opposed to merely a cytostatic effect as determined by combination treatment-induced in caspase activation. Characterization of this unexpected finding was undertaken in biochemical assays and cellular assays, including those described herein.

The disclosure is thus further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Treatment of Mutant KIT Mast Cell Lines with Compound A or Compound B Inhibits Cell Proliferation and KIT Phosphorylation of Mastocytosis Cell Lines A study was performed that demonstrates that treatment with Compound A or Compound B inhibited cell proliferation of mutant KIT HMC1.1 KIT V560G and HMC1.2 KIT V560G/D816V mast cell lines. Assays were conducted in 96 well plates with 10,000 cells seeded per well. The cells were treated with vehicle control, Compound A, or Compound B thereof at varying concentrations, allowed to grow for 72 hours, and then cell proliferation was assessed.

FIG. 1A is a graphical representation showing the relative percentage of cell proliferation determined for various concentrations of Compound A. Treatment with Compound A inhibited cell proliferation growth in HMC1.1 V560G and HMC1.2 V560G/D816V mast cell lines with IC50 values of 2.6 nM and 97 nM, respectively.

Figure 1B:
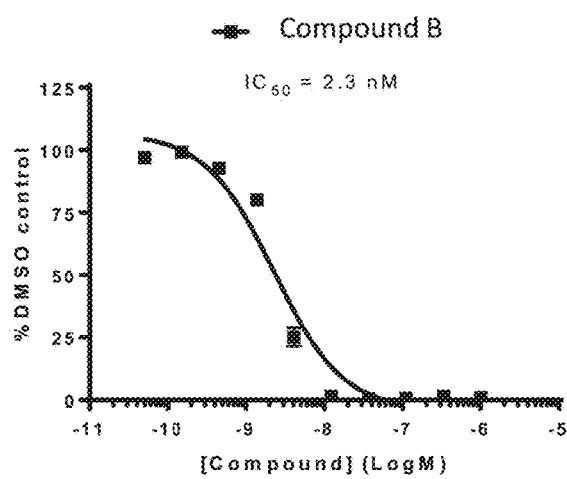
FIG. 1B shows graphical representations of cell proliferation following the indicated drug treatment with Compound B as compared to vehicle control in HMC1.1 V560G (left panel) and HMC1.2 V560G/D816V (right panel) cell lines.
Figure 1B:
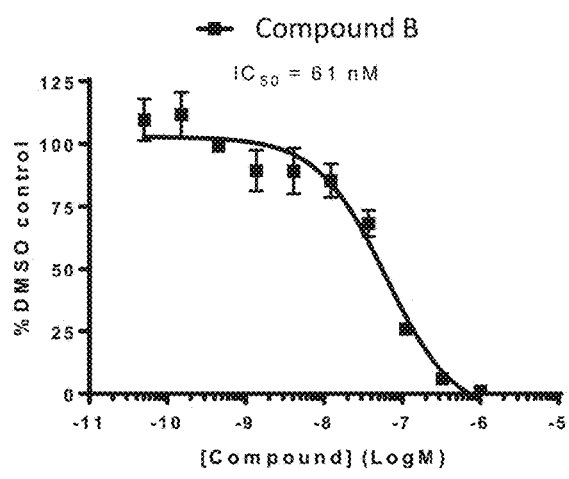

FIG. 1B is a graphical representation showing the relative percentage of cell proliferation determined for various concentrations of Compound B. Treatment with Compound B inhibited cell proliferation growth in HMC1.1 V560G and HMC1.2 V560G/D816V cell lines with IC50 values of 2.3 nM and 61 nM, respectively.

Example 2

Combination Treatment with Compound A and Trametinib Induces Apoptosis in Mastocytosis Cell Lines A study was performed to demonstrate that combination treatment with Compound A and the MEK inhibitor trametinib induced apoptosis in the HMC1.2 KIT V560G/D816V mastocytosis cell line. Assays were conducted in 96 well plates with 10,000 cells seeded per well. Cells were treated with vehicle control, Compound A, trametinib, or combinations thereof at varying concentrations, and the cells were allowed to grow for 24 hours. Apoptosis was assessed by measuring caspase 3/7 activity.

Figure 2A:
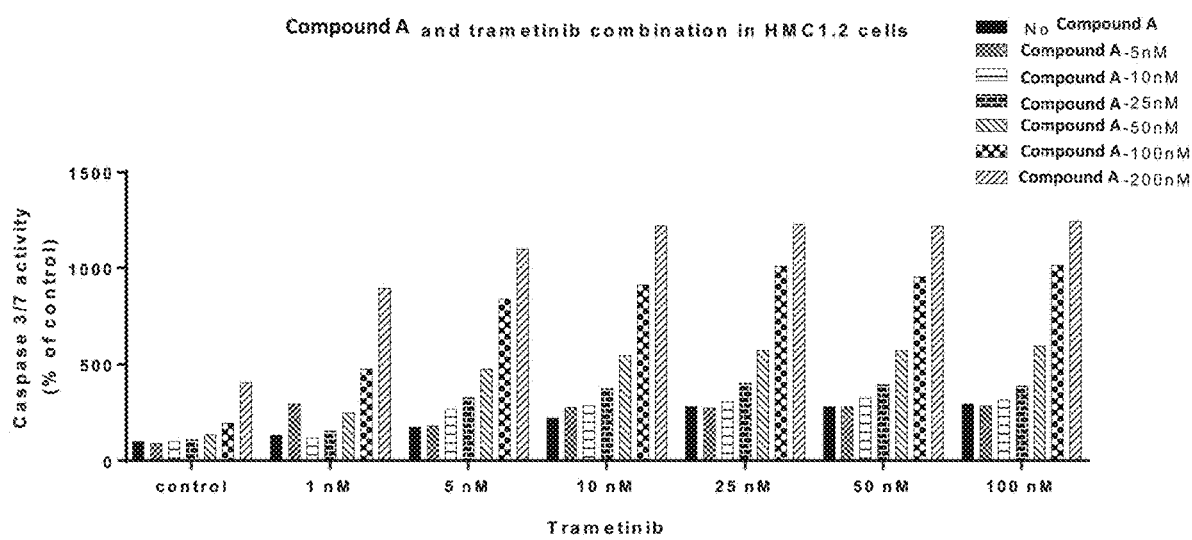
FIG. 2A shows a graphical representation of caspase activity following the indicated various treatments with Compound A and trametinib in the HMC1.2 V560G/D816V cell line.
Figure 2C:
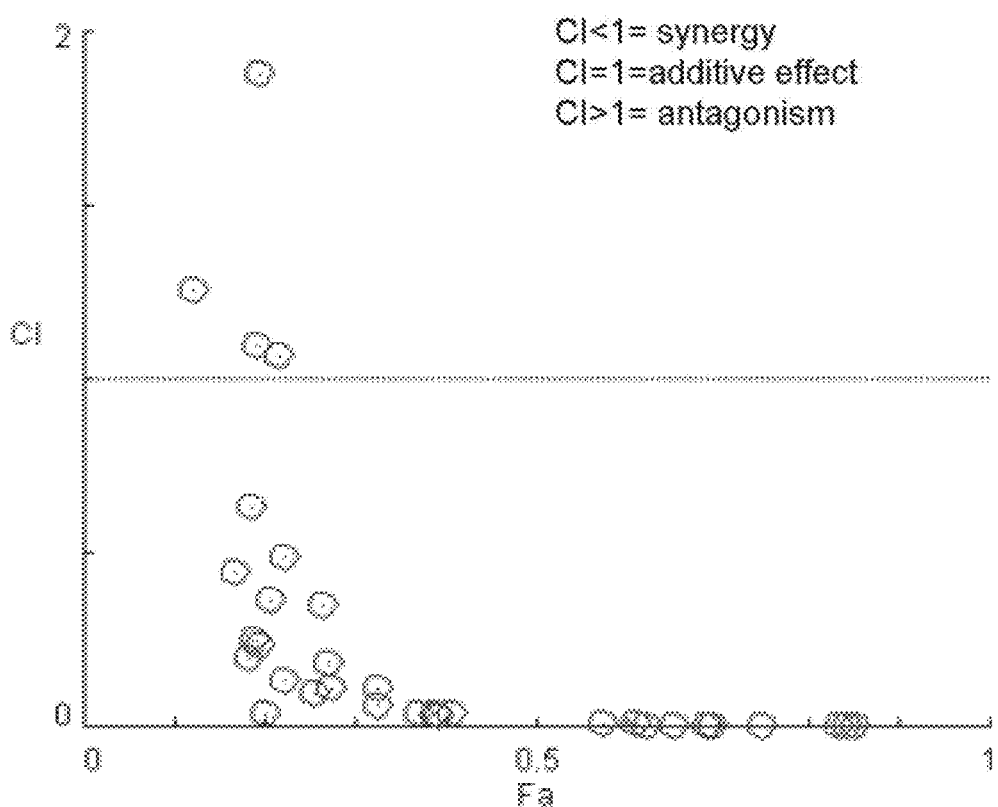
FIG. 2C provides a Combination Index Plot for the combination of Compound A with the MEK inhibitor trametinib.

FIG. 2A is graphical representation showing the relative percentage of cell apoptosis determined for various treatments. FIG. 2B is a matrix for synergy chart based on the combination index (CI) method described by Chou and Talalay (1984) and the computer software of Chou and Martin (2005). CI<1 indicates synergism, CI=1 indicates additive effect, and CI>1 indicates antagonism. Combination treatments with Compound A and the MEK inhibitor trametinib unexpectedly showed strong synergy for inducing apoptosis of HMC1.2 KIT V560G/D816V cells. FIG. 2C is a Combination Index Plot of the CI, demonstrating strong synergy for combination of Compound A with trametinib for inducing apoptosis of HMC1.2 KIT V560G/D816V mast cells.

Example 3

Combination Treatment with Compound B and Trametinib Induces Apoptosis in Mastocytosis Cell Lines A study was also performed to demonstrate that combination treatment with Compound B and trametinib induced apoptosis in the HMC1.2 KIT V560G/D816V mastocytosis cell line. Assays were conducted as explained in example 2. Apoptosis was assessed by measuring caspase 3/7 activity.

Figure 3A:
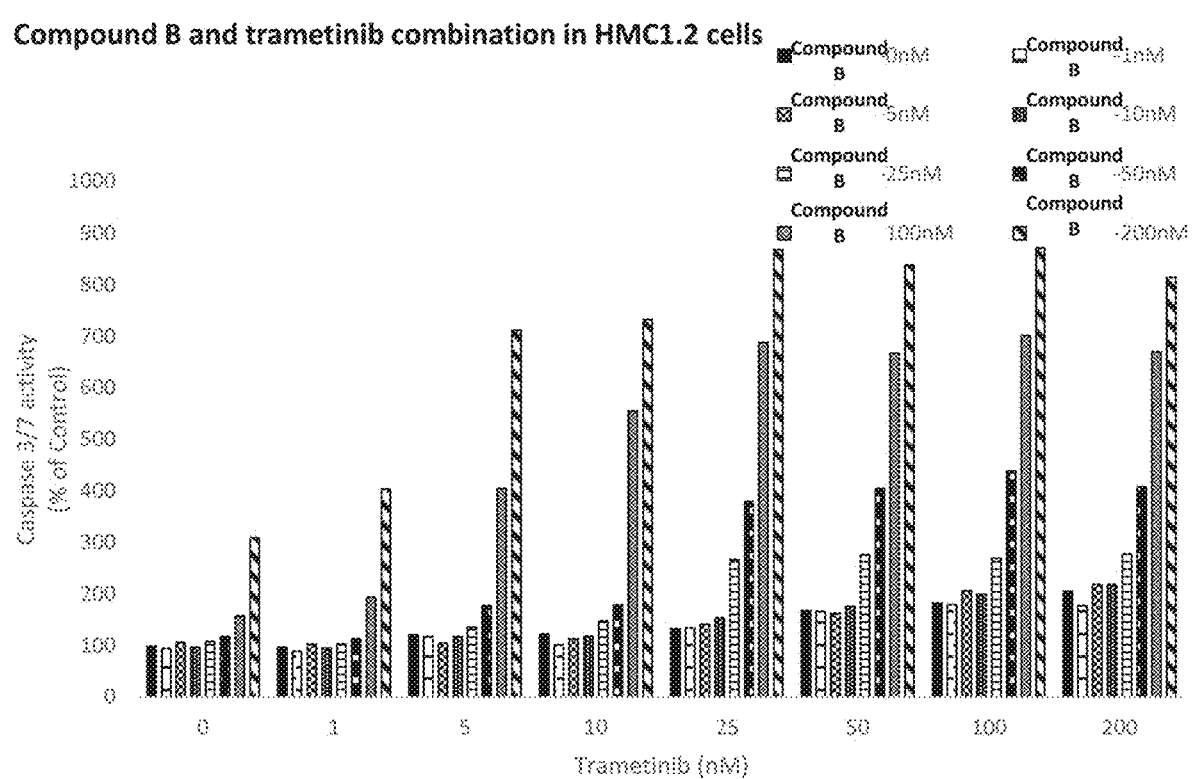
FIG. 3A shows a graphical representation of caspase activity following the indicated various treatments with Compound B and trametinib in the HMC1.2 V560G/D816V cell line.
Figure 3C:
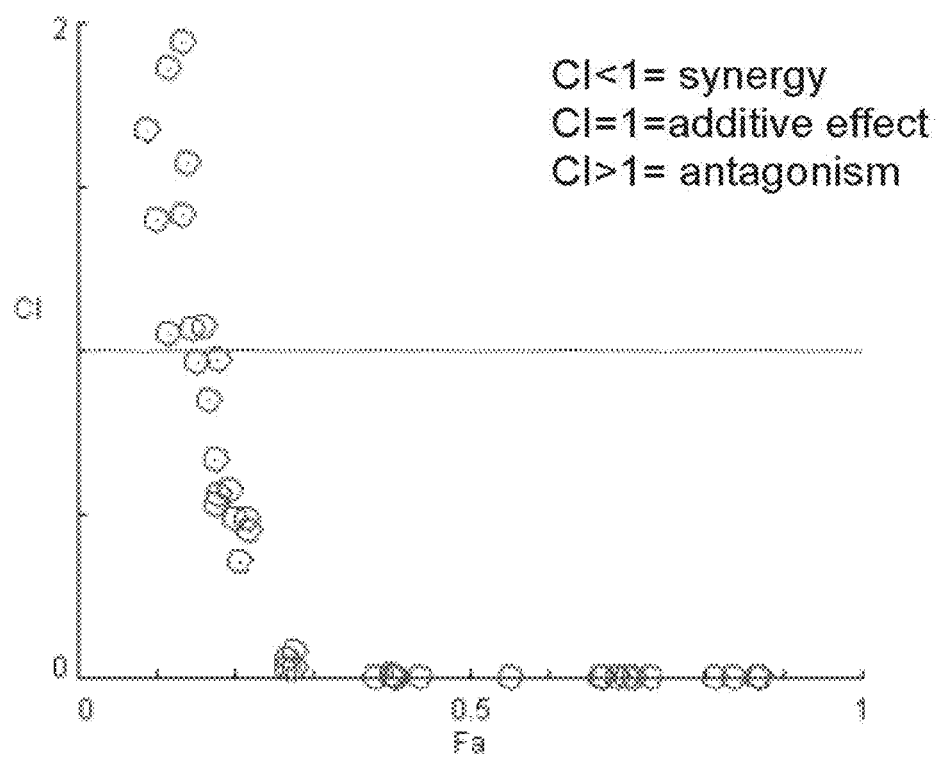
FIG. 3C provides a Combination Index Plot for the combination of Compound B with the MEK inhibitor trametinib.

FIG. 3A is graphical representation showing the relative percentage of cell apoptosis determined for various treatments. FIG. 3B is a matrix for synergy chart based on the combination index (CI) method described by Chou and Talalay (1984) and the computer software of Chou and Martin (2005). CI<1 indicates synergism, CI=1 indicates additive effect, and CI>1 indicates antagonism. Combination treatments with Compound B and the MEK inhibitor trametinib unexpectedly showed strong synergy for inducing apoptosis of HMC1.2 KIT V560G/D816V cells. FIG. 3C is a Combination Index Plot of the CI, demonstrating strong synergy for combination of Compound B with trametinib for inducing apoptosis of HMC1.2 KIT V560G/D816V mast cells.

Example 4

Combination Treatment with Compound A and Binimetinib Induces Apoptosis in Mastocytosis Cell Lines Combination treatment with Compound A and binimetinib also induced apoptosis in the HMC1.2 KIT V560G/D816V mastocytosis cell line. Assays were conducted as explained in example 2. Apoptosis was assessed by measuring caspase 3/7 activity.

Figure 4A:
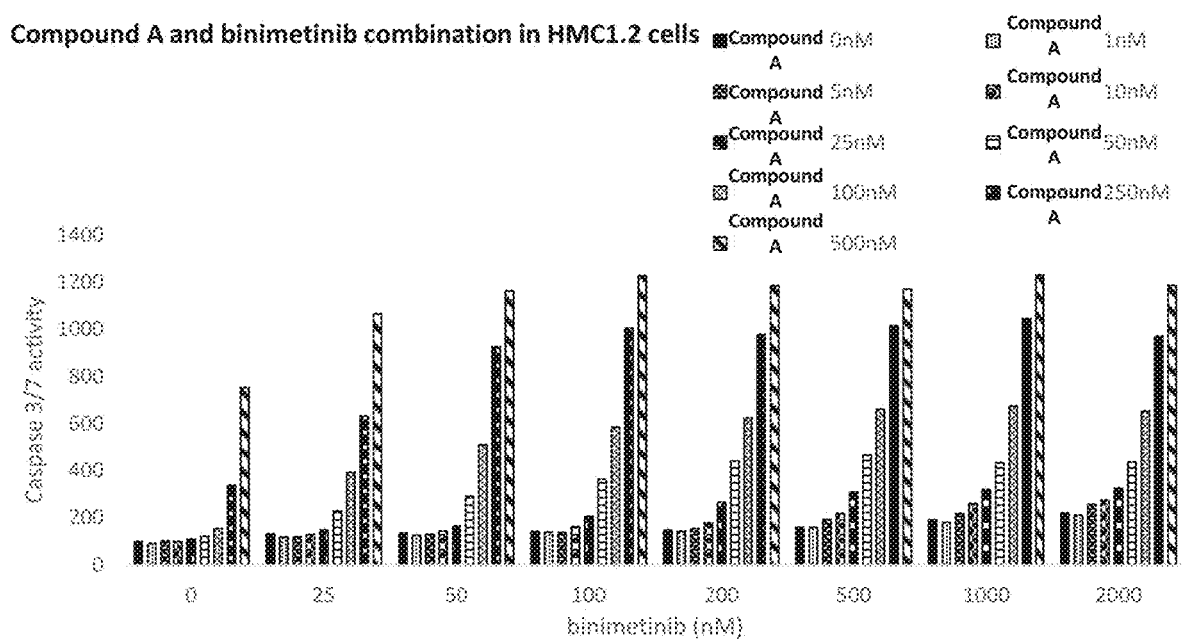
FIG. 4A shows a graphical representation of caspase activity following the indicated various treatments with Compound A and binimetinib in the HMC1.2 V560G/D816V cell line.
Figure 4C:
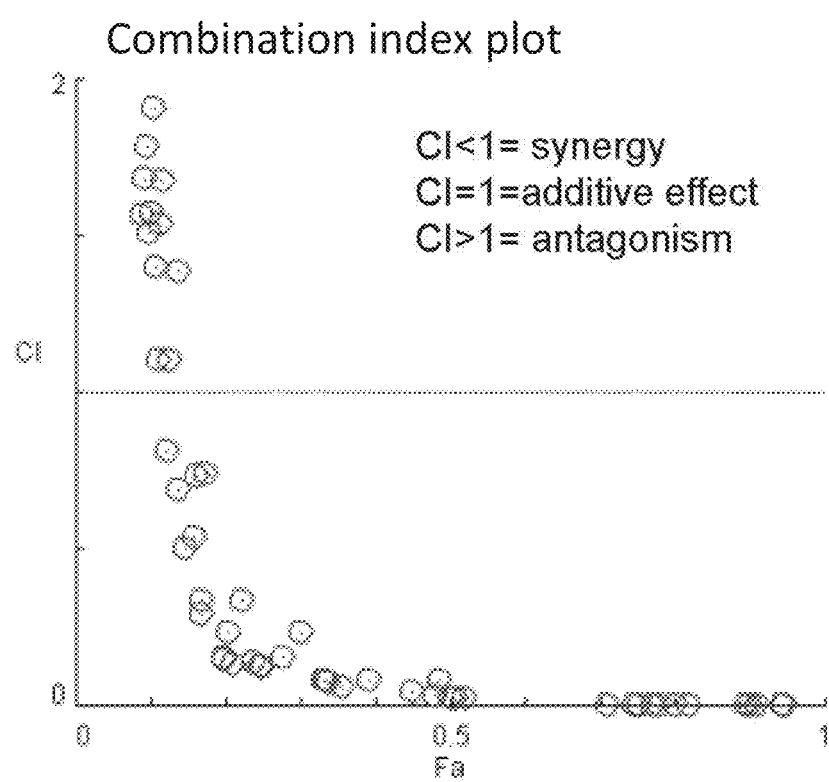
FIG. 4C provides a Combination Index Plot for the combination of Compound A with the MEK inhibitor binimetinib.

FIG. 4A is graphical representation showing the relative percentage of cell apoptosis determined for various treatments. FIG. 4B is a matrix for synergy chart based on the combination index (CI) method described by Chou and Talalay (1984) and the computer software of Chou and Martin (2005). Combination treatments with Compound A and the MEK inhibitor binimetinib unexpectedly showed strong synergy for inducing apoptosis of HMC1.2 KIT V560G/D816V cells. FIG. 4C is a Combination Index Plot of the CI, demonstrating strong synergy for combination of Compound A with binimetinib for inducing apoptosis of HMC1.2 KIT V560G/D816V mast cells.

Example 5

Figure 5A:
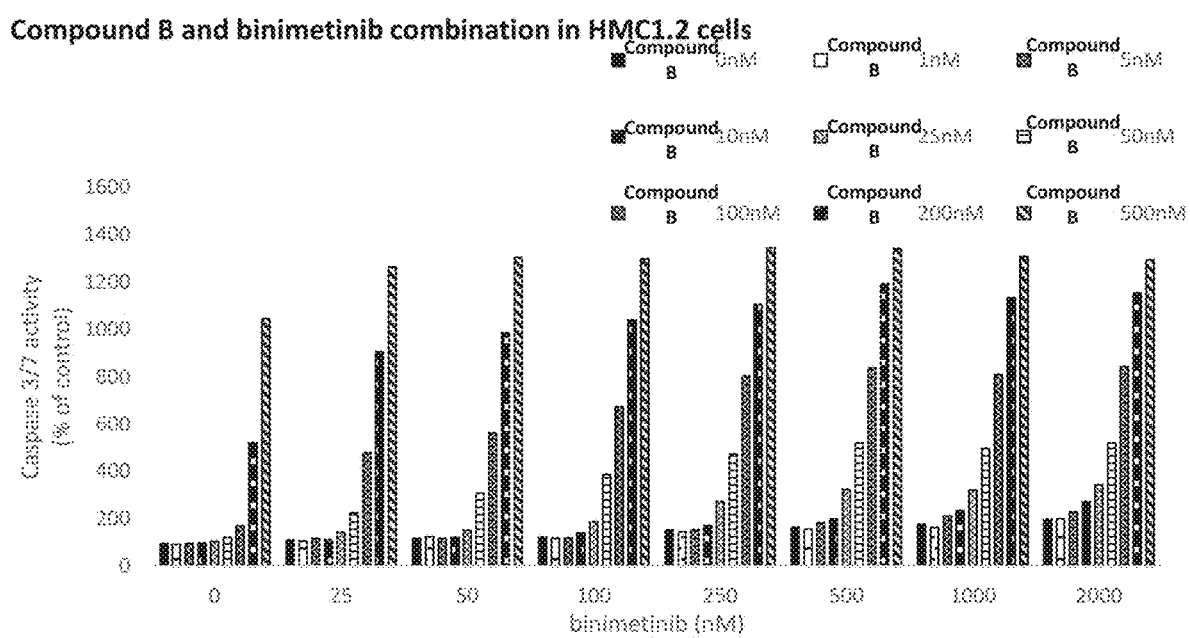
FIG. 5A shows a graphical representation of caspase activity following the indicated various treatments with Compound B and binimetinib in the HMC1.2 V560G/D816V cell line.

Combination Treatment with Compound B and Binimetinib Induces Apoptosis in Mastocytosis Cell Lines FIG. 5A is graphical representation showing the relative percentage of cell apoptosis determined for various treatments of Compound B and binimetinib. FIG. 5B is a matrix for synergy chart based on the combination index (CI) method described by Chou and Talalay (1984) and the computer software of Chou and Martin (2005). CI<1 indicates synergism, CI=1 indicates additive effect, and CI>1 indicates antagonism. Combination treatments with Compound B and the MEK inhibitor binimetinib unexpectedly showed strong synergy for inducing apoptosis of HMC1.2 KIT V560G/D816V cells. FIG. 5C is a Combination Index Plot of the CI, demonstrating strong synergy for combination of Compound B with binimetinib for inducing apoptosis of HMC1.2 KIT V560G/D816V mast cells.

Example 6

Figure 6A:
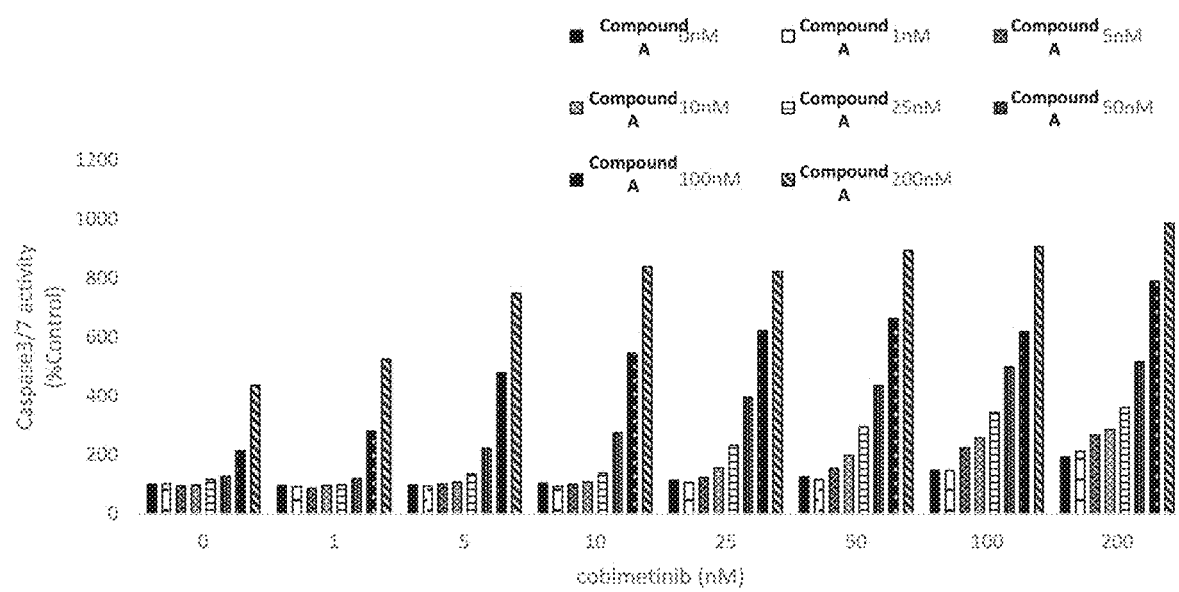
FIG. 6A shows a graphical representation of caspase activity following the indicated various treatments with Compound A and cobimetinib in the HMC1.2 V560G/D816V cell line.
Figure 6C:
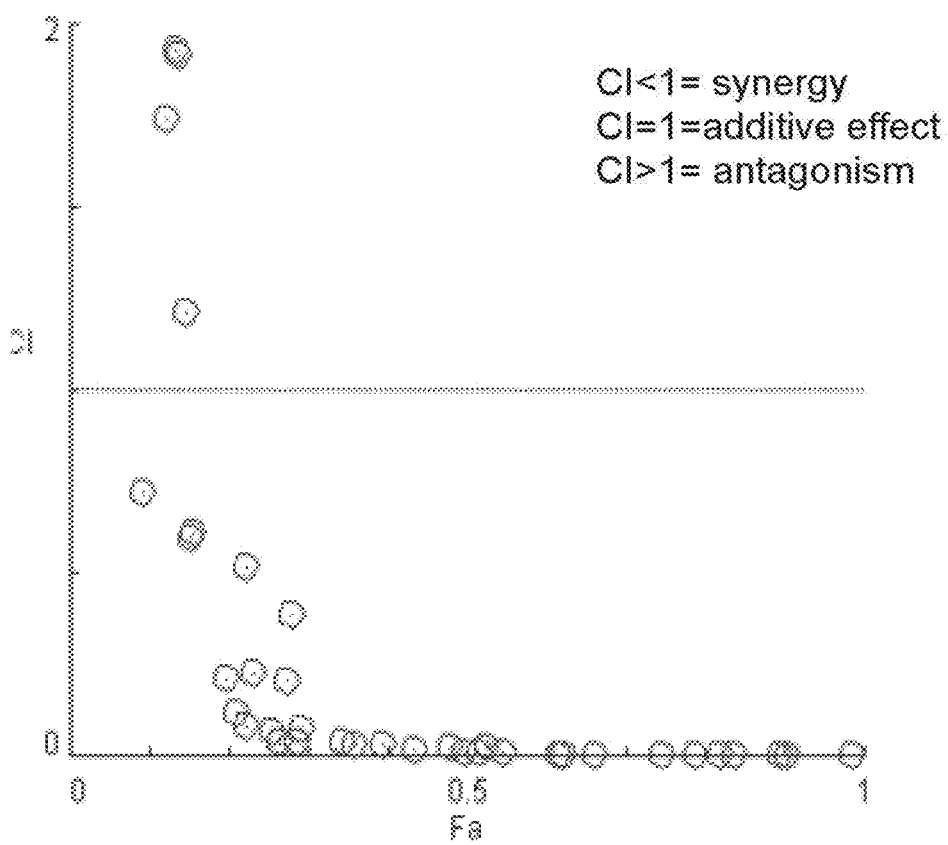
FIG. 6C provides a Combination Index Plot for the combination of Compound A with the MEK inhibitor cobimetinib.

Combination Treatment with Compound A and Cobimetinib Induces Apoptosis in Mastocytosis Cell Lines FIG. 6A is graphical representation showing the relative percentage of cell apoptosis determined for various treatments of Compound A and cobimetinib. FIG. 6B is a matrix for synergy chart based on the combination index (CI) method described by Chou and Talalay (1984) and the computer software of Chou and Martin (2005). Combination treatments with Compound A and the MEK inhibitor cobimetinib unexpectedly showed strong synergy for inducing apoptosis of HMC1.2 KIT V560G/D816V cells. FIG. 6C is a Combination Index Plot of the CI, demonstrating strong synergy for combination of Compound A with cobimetinib for inducing apoptosis of HMC1.2 KIT V560G/D816V mast cells.

Example 7

Figure 7A:
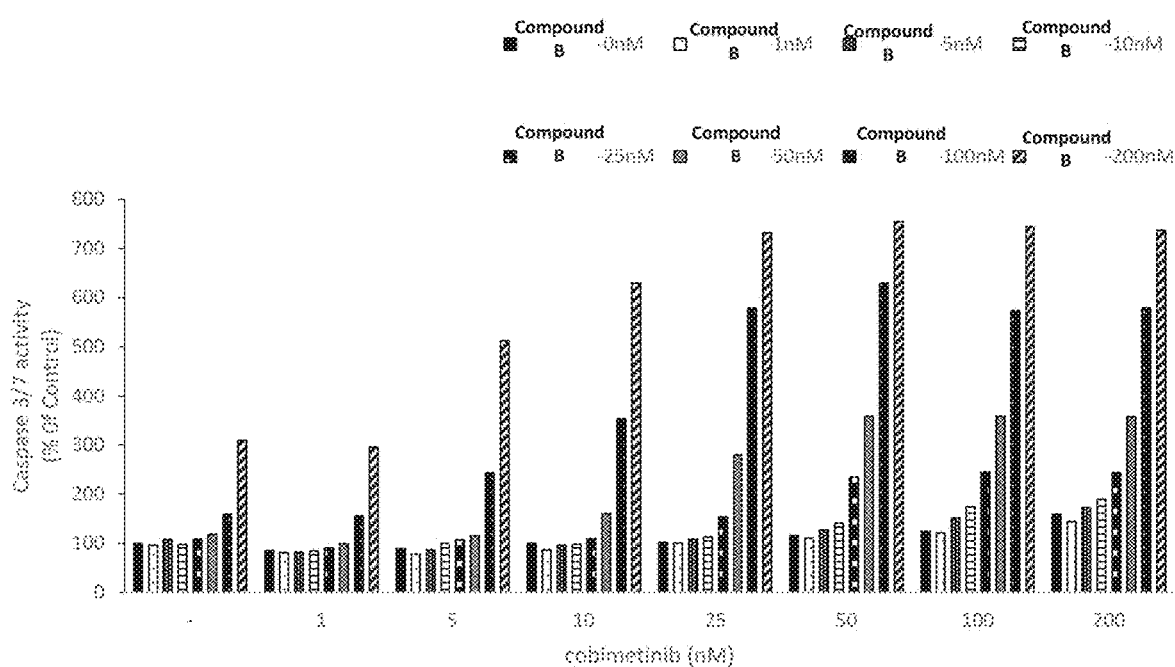
FIG. 7A shows a graphical representation of caspase activity following the indicated various treatments with Compound B and cobimetinib in the HMC1.2 V560G/D816V cell line.
Figure 7C:
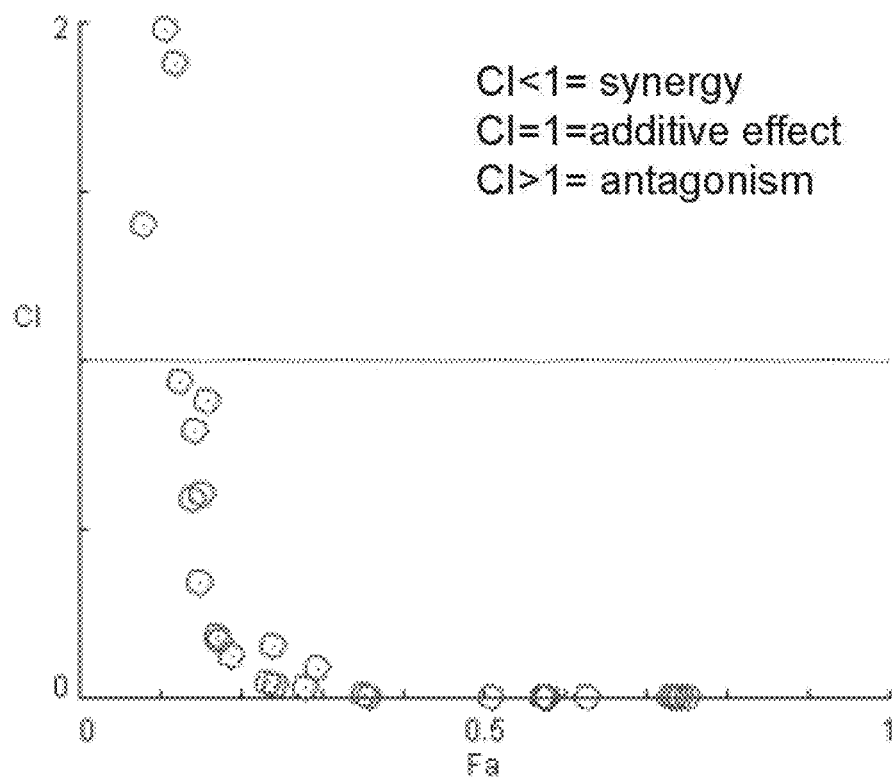
FIG. 7C provides a Combination Index Plot for the combination of Compound B with the MEK inhibitor cobimetinib.

Combination Treatment with Compound B and Cobimetinib Induces Apoptosis in Mastocytosis Cell Lines FIG. 7A is graphical representation showing the relative percentage of cell apoptosis determined for various treatments of Compound B and cobimetinib. FIG. 7B is a matrix for synergy chart based on the combination index (CI) method described by Chou and Talalay (1984) and the computer software of Chou and Martin (2005). CI<1 indicates synergism, CI=1 indicates additive effect, and CI>1 indicates antagonism. Combination treatments with Compound B and the MEK inhibitor cobimetinib unexpectedly showed strong synergy for inducing apoptosis of HMC1.2 KIT V560G/D816V cells. FIG. 7C is a Combination Index Plot of the CI, demonstrating strong synergy for combination of Compound B with cobimetinib for inducing apoptosis of HMC1.2 KIT V560G/D816V mast cells.

Example 8

Figure 8A:
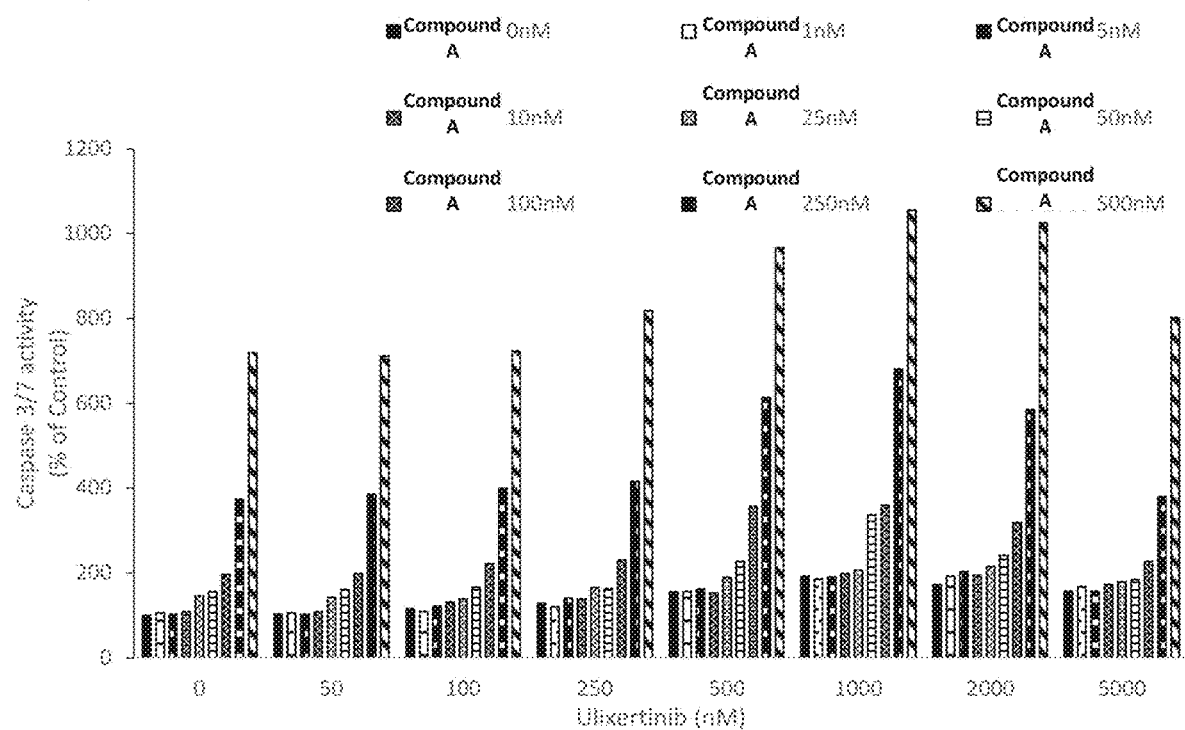
FIG. 8A shows a graphical representation of caspase activity following the indicated various treatments with Compound A and the ERK inhibitor ulixertinib in the HMC1.2 V560G/D816V cell line.
Figure 8C:
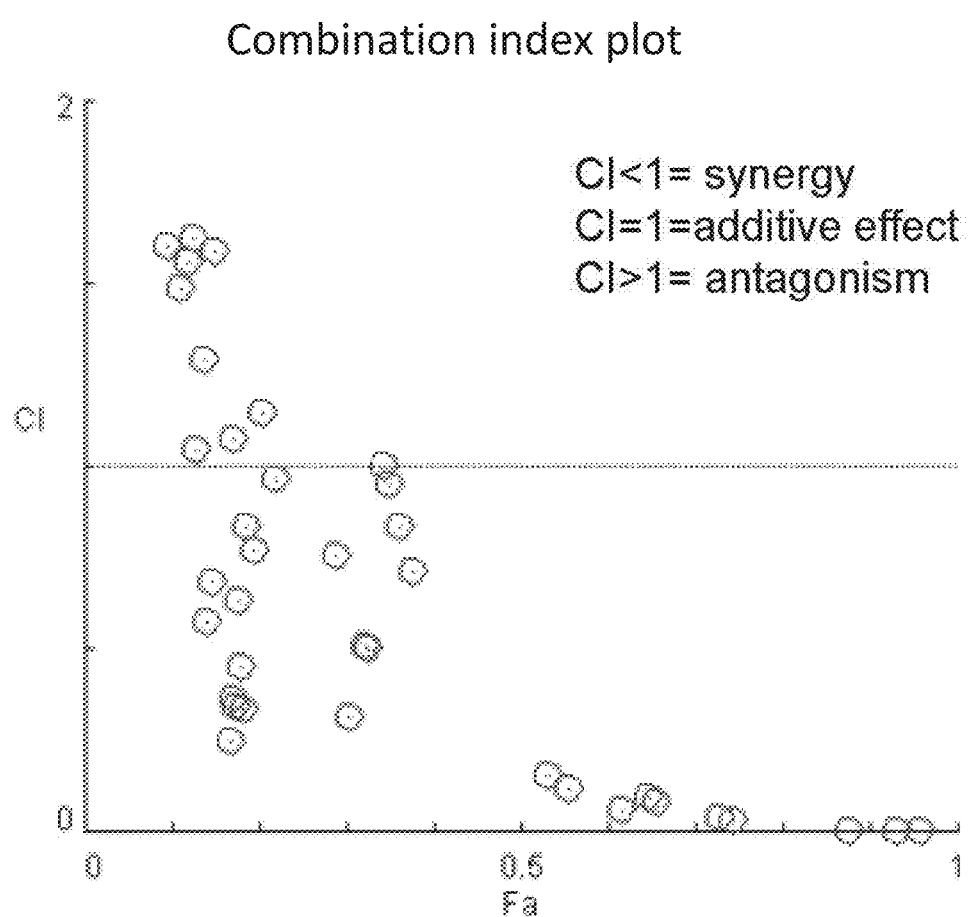
FIG. 8C provides a Combination Index Plot for the combination of Compound A with the ERK inhibitor ulixertinib.

Combination Treatment with Compound A and Ulixertinib Induces Apoptosis in Mastocytosis Cell lines FIG. 8A is graphical representation showing the relative percentage of cell apoptosis determined for various treatments of Compound A and the ERK inhibitor ulixertinib. FIG. 8B is a matrix for synergy chart based on the combination index (CI) method described by Chou and Talalay (1984) and the computer software of Chou and Martin (2005). Combination treatments with Compound A and ulixertinib unexpectedly showed strong synergy for inducing apoptosis of HMC1.2 KIT V560G/D816V cells. FIG. 8C is a Combination Index Plot of the CI, demonstrating strong synergy for combination of Compound A with ulixertinib for inducing apoptosis of HMC1.2 KIT V560G/D816V mast cells.

Example 9

Combination Treatment with Compound B and Ulixertinib Induces Apoptosis in Mastocytosis Cell Lines Combination treatment of Compound B and the ERK inhibitor ulixertinib can be evaluated for induction of apoptosis in HMC1.2 KIT V560G/D816V mast cells. A matrix for synergy chart based on the combination index (CI) method can be generated as described by Chou and Talalay (1984) and the computer software of Chou and Martin (2005). Combination treatments with Compound B and ulixertinib can be used to show synergy for inducing apoptosis of HMC1.2 KIT V560G/D816V cells. A Combination Index Plot of the CI can be used to demonstrate synergy for combination of Compound B and ulixertinib for inducing apoptosis of HMC1.2 KIT V560G/D816V mast cells.

Example 10

Combination Treatment with Compound A and SCH772984 Induces Apoptosis in Mastocytosis Cell Lines Combination treatment of Compound A and the ERK inhibitor SCH772984 can be evaluated for induction of apoptosis in HMC1.2 KIT V560G/D816V mast cells. A matrix for synergy chart based on the combination index (CI) method can be generated as described by Chou and Talalay (1984) and the computer software of Chou and Martin (2005). Combination treatments with Compound A and SCH772984 can be used to show synergy for inducing apoptosis of HMC1.2 KIT V560G/D816V cells. A Combination Index Plot of the CI can be used to demonstrate synergy for combination of Compound A and SCH772984 for inducing apoptosis of HMC1.2 KIT V560G/D816V mast cells.

Example 11

Combination Treatment with Compound B and SCH772984 Induces Apoptosis in Mastocytosis Cell Lines Combination treatment of Compound B and the ERK inhibitor SCH772984 can be evaluated for induction of apoptosis in HMC1.2 KIT V560G/D816V mast cells. A matrix for synergy chart based on the combination index (CI) method can be generated as described by Chou and Talalay (1984) and the computer software of Chou and Martin (2005). Combination treatments with Compound A and SCH772984 can be used to show synergy for inducing apoptosis of HMC1.2 KIT V560G/D816V cells. A Combination Index Plot of the CI can be used to demonstrate synergy for combination of Compound B and SCH772984 for inducing apoptosis of HMC1.2 KIT V560G/D816V mast cells.

Example 12

Combination Treatment with Compound A and LY3009120 Induces Apoptosis in Mastocytosis Cell Lines Combination treatment of Compound A and the RAF inhibitor LY3009120 can be evaluated for induction of apoptosis in HMC1.2 KIT V560G/D816V mast cells. A matrix for synergy chart based on the combination index (CI) method can be generated as described by Chou and Talalay (1984) and the computer software of Chou and Martin (2005). Combination treatments with Compound A and LY3009120 can be used to show synergy for inducing apoptosis of HMC1.2 KIT V560G/D816V cells. A Combination Index Plot of the CI can be used to demonstrate strong synergy for combination of Compound A and LY3009120 for inducing apoptosis of HMC1.2 KIT V560G/D816V mast cells.

Example 13

Combination Treatment with Compound B and LY3009120 Induces Apoptosis in Mastocytosis Cell Lines Combination treatment of Compound B and the RAF inhibitor LY3009120 can be evaluated for induction of apoptosis in HMC1.2 KIT V560G/D816V mast cells. A matrix for synergy chart based on the combination index (CI) method can be generated as described by Chou and Talalay (1984) and the computer software of Chou and Martin (2005). Combination treatments with Compound B and LY3009120 can be used to show synergy for inducing apoptosis of HMC1.2 KIT V560G/D816V cells. A Combination Index Plot of the CI can be used to demonstrate synergy for combination of Compound B and LY3009120 for inducing apoptosis of HMC1.2 KIT V560G/D816V mast cells.

Example 14

Figure 9A:
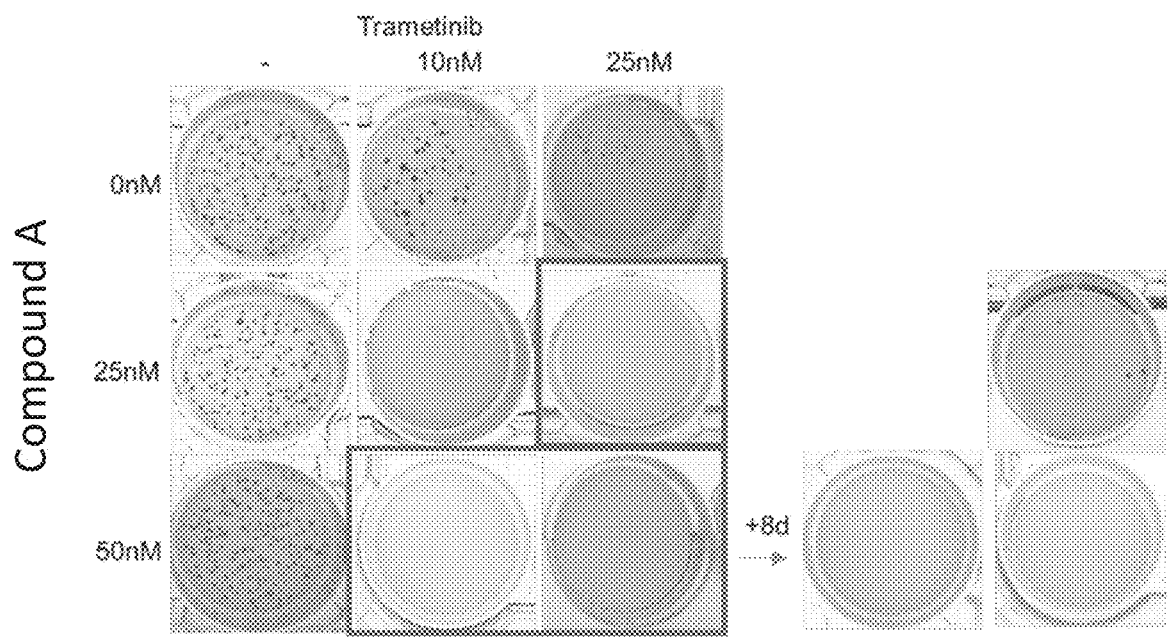
FIG. 9A shows the inhibition of colony outgrowth from treatment with single agent Compound A, single agent trametinib, and the combination of Compound A with the MEK inhibitor trametinib in an HMC1.2 V560G/D816V cells.

Combination Treatment with Compound A and Trametinib Leads to Synergistic Decrease in Colony Outgrowth of HMC1.2 KIT D816V Mast Cell Line A study was performed to demonstrate that combination treatment with Compound A and the MEK inhibitor trametinib leads to decreased colony out growth of HMC1.2, compared to treatment with either single agent. 10,000 HMC1.2 cells were grown in soft agar and incubated with various concentrations of Compound A, trametinib, or a combination of Compound A and trametinib for 10 days. Drug treatments were removed and colony outgrowth of viable cells was monitored after 5 additional days. FIG. 9A is a representative picture of colony outgrowth of HMC1.2 mast cells after treatment with trametinib (0, 10, or 25 nM), Compound A (0, 25, or 50 nM) as single agents or as a matrix combination of various concentrations of Compound A with various concentrations of trametinib. Whereas the single agent treatment with Compound A or trametinib resulted in colony outgrowth at all concentrations 5 days after drug removal, the combination of Compound A with trametinib resulted in less colony outgrowth 5 days after drug removal. Combination of Compound A (25 nM) with trametinib (25 nM) resulted in a complete eradication of colony outgrowth after 5 days of drug removal. Combination of Compound A (50 nM) with trametinib (10 or 25 nM) unexpectedly resulted in complete eradication of outgrowth of viable HMC1.2 cells to the limit of detection as determined by visualization with 5× objective microscopy after 5 days of drug removal, whereas eradication was not observed upon treatment with single agent Compound A or single agent trametinib. Further extension of colony outgrowth to 8 additional days (a total of 13 days) after drug removal still maintained eradication to the limit of detection of colony outgrowth with the combination of Compound A (50 nM) and trametinib (10 and 25 nM). However, ~15-20 colonies outgrew after extra 8 days of incubation with the combination of Compound A (25 nM) and trametinib (25 nM). (FIG. 9A right panel).

Figure 9B:
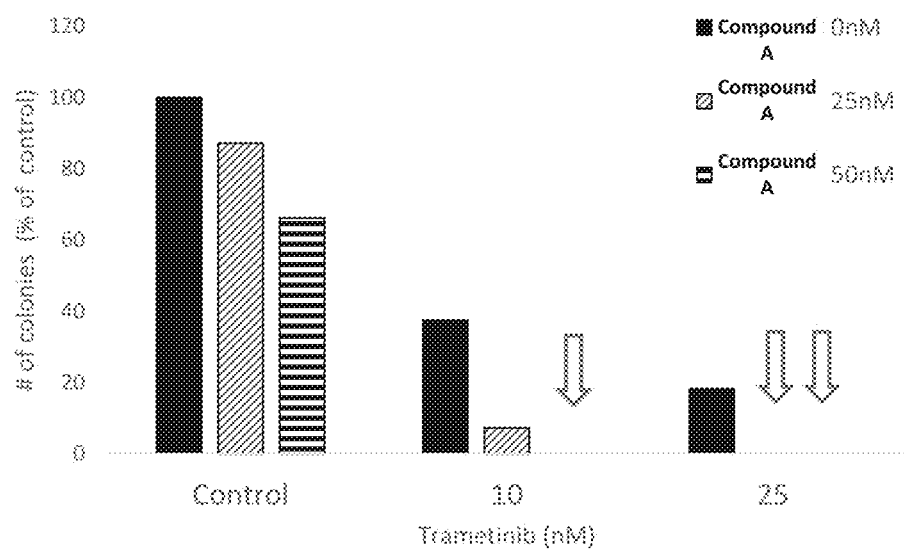
FIG. 9B shows a graphical representation of inhibition of colony outgrowth from treatment with single agent Compound A, single agent trametinib, and the combination of Compound A with the MEK inhibitor trametinib in HMC1.2 V560G/D816V cells. Arrows indicate no colony outgrowth.

FIG. 9B is a graphical representation quantifying colony outgrowth of HMC1.2 mast cells after the various treatments from FIG. 9A. Combination treatment with Compound A at 50 nM and trametinib at either 10 nM or 25 nM unexpectedly resulted in eradication of colony outgrowth to the limit of detection as determined by visualization with 5× objective microscopy (see arrows, FIG. 9B). Combination treatment with Compound A at 25 nM and trametinib at 25 nM unexpectedly resulted in eradication of colony outgrowth to the limit of detection as determined by visualization with 5× objective microscopy (see arrows, FIG. 9B),Eradication was not observed upon treatment with either single agent Compound A or trametinib.

Example 15

Combination Treatment with Compound B and Trametinib Leads to Synergistic Decrease in Colony Outgrowth of HMC1.2 KIT D816V Mast Cell Line A study was also performed with Compound B and the MEK inhibitor trametinib to evaluate a decrease in colony outgrowth in HMC1.2 cells as described in Example 14.

Figure 10A:
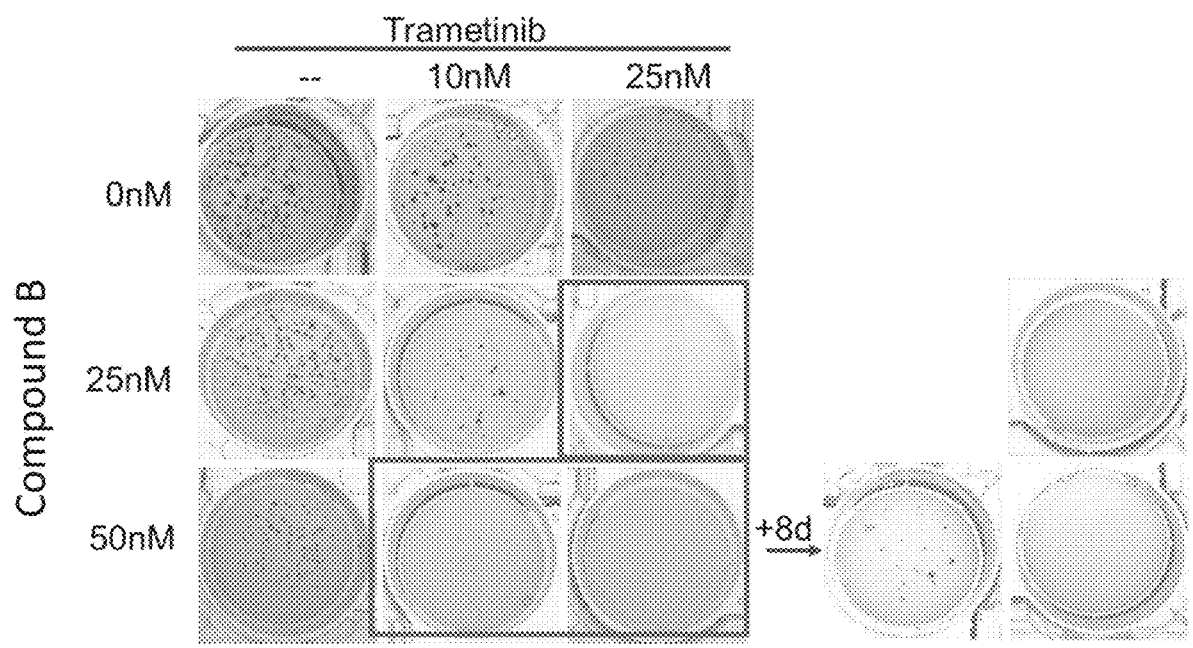
FIG. 10A shows the inhibition of colony outgrowth from treatment with single agent Compound B, single agent trametinib, and the combination of Compound B with the MEK inhibitor trametinib in an HMC1.2 V560G/D816V cells.
Figure 10B:
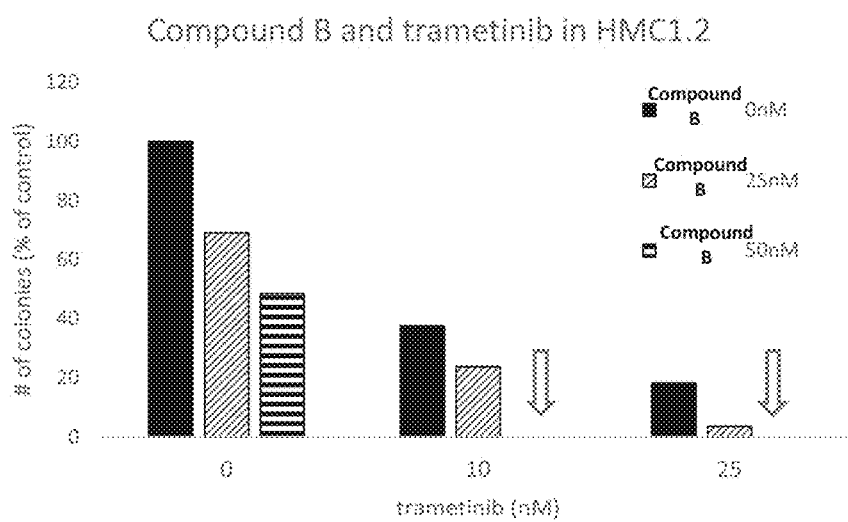
FIG. 10B shows a graphical representation of inhibition of colony outgrowth from treatment with single agent Compound B, single agent trametinib, and the combination of Compound B with the MEK inhibitor trametinib in HMC1.2 V560G/D816V cells. Arrows indicate no colony outgrowth.

FIG. 10A is a representative picture of colony outgrowth of HMC1.2 mast cells after treatment with trametinib (0, 10, or 25 nM), Compound B (0, 25, or 50 nM) as single agents or as a matrix combination of various concentrations of Compound B with various concentrations of trametinib. Whereas the single agent treatment with Compound B or trametinib resulted in colony outgrowth at all concentrations 5 days after drug removal, the combination of Compound B with trametinib resulted in less colony outgrowth 5 days after drug removal. Combination of Compound B (25 nM) with trametinib (25 nM) resulted in a significant decrease in outgrowth of viable HMC1.2 cells after 5 days of drug removal. Combination of Compound B (50 nM) with trametinib (10 or 25 nM) unexpectedly resulted in complete eradication of outgrowth of viable HMC1.2 cells to the limit of detection as determined by visualization with 5× objective microscopy after 5 days of drug removal, whereas eradication was not observed upon treatment with single agent Compound B or single agent trametinib. Further extension of colony outgrowth to 8 additional days (a total of 13 days) after drug removal still maintained eradication to the limit of detection of colony outgrowth with the combination of Compound B (50 nM) and trametinib (25 nM). FIG. 10B is a graphical representation quantifying colony outgrowth of HMC1.2 mast cells after the various treatments from FIG. 10A. Combination treatment with Compound B at 50 nM and trametinib at either 10 nM or 25 nM unexpectedly resulted in eradication of colony outgrowth to the limit of detection as determined by visualization with 5× objective microscopy, whereas eradication was not observed upon treatment with either single agent Compound B or trametinib (see arrows, FIG. 10B).

Example 16

Figure 11A:
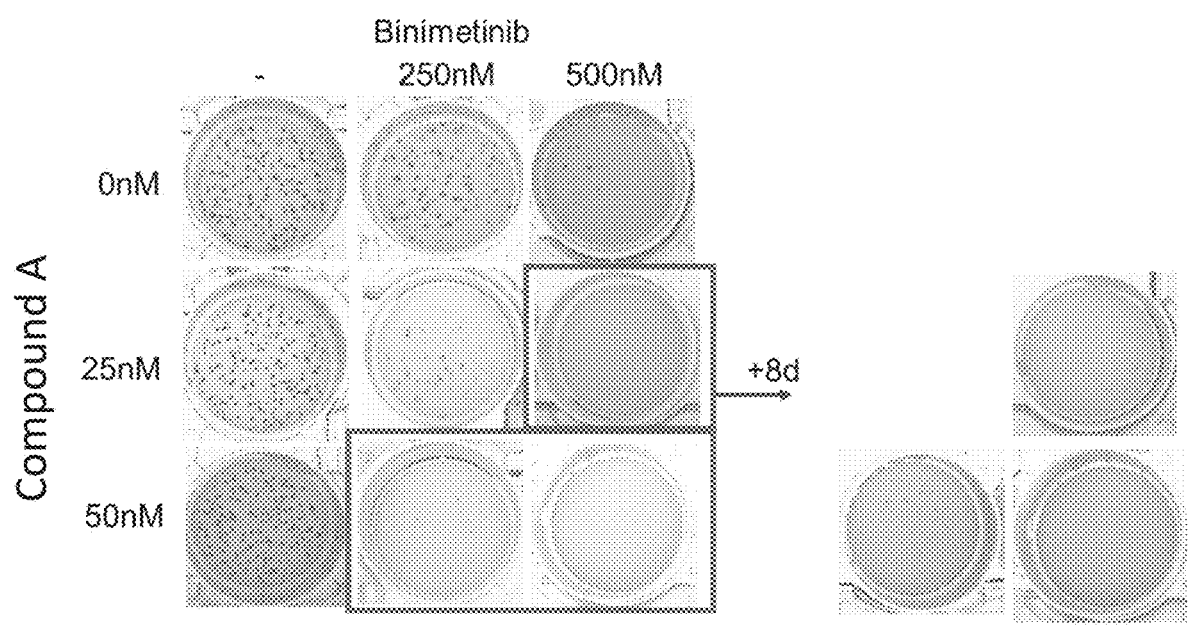
FIG. 11A shows the inhibition of colony outgrowth from treatment with single agent Compound A, single agent binimetinib, and the combination of Compound A with the MEK inhibitor binimetinib in an HMC1.2 V560G/D816V cells.

Combination Treatment with Compound A and Binimetinib Leads to Synergistic Decrease in Colony Outgrowth of HMC1.2 KIT D816V Mast Cell Line FIG. 11A is a representative picture of colony outgrowth of HMC1.2 mast cells after treatment with binimetinib (0, 250, or 500 nM), Compound A (0, 25, or 50 nM) as single agents or as a matrix combination of various concentrations of Compound A with various concentrations of binimetinib. Whereas the single agent treatment with Compound A or binimetinib resulted in colony outgrowth at all concentrations 5 days after drug removal, the combination of Compound A with binimetinib resulted in less colony outgrowth 5 days after drug removal. Combination of Compound A (25 nM) with binimetinib (250 nM) resulted in a significant decrease in outgrowth of viable HMC1.2 cells after 5 days of drug removal. Combination of Compound A (50 nM) with binimetinib (250 nM or 500 nM) unexpectedly resulted in complete eradication of outgrowth of viable HMC1.2 cells to the limit of detection as determined by visualization with 5× objective microscopy after 5 days of drug removal, whereas eradication was not observed upon treatment with 25 single agent Compound A or single agent binimetinib. Further extension of colony outgrowth to 8 additional days (a total of 13 days) after drug removal still maintained eradication to the limit of detection of colony outgrowth with the combination of Compound A (50 nM) and binimetinib (500 nM). However, ~10-15 colonies outgrew with the combination of Compound A (50 nM) and binimetinib (250 nM).

Figure 11B:
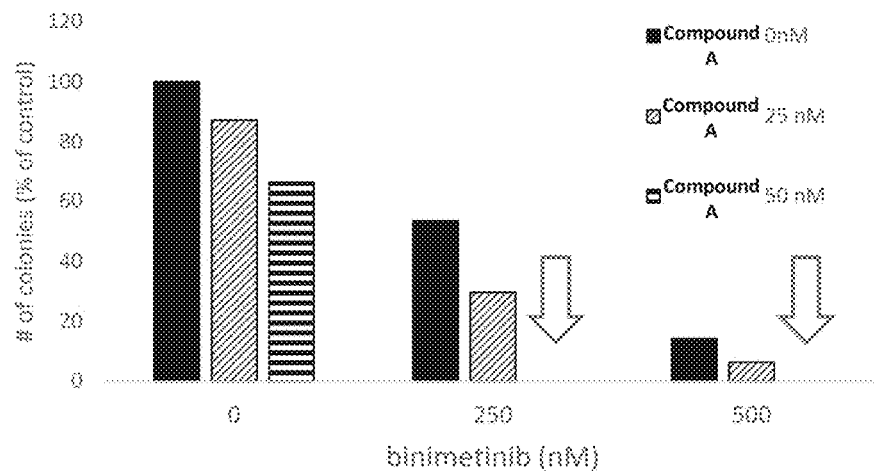
FIG. 11B shows a graphical representation of inhibition of colony outgrowth from treatment with single agent Compound A, single agent binimetinib, and the combination of Compound A with the MEK inhibitor binimetinib in HMC1.2 V560G/D816V cells. Arrows indicate no colony outgrowth.

FIG. 11B is a graphical representation quantifying colony outgrowth of HMC1.2 mast cells after the various treatments from FIG. 11A. Combination treatment with Compound A at 50 nM and binimetinib at 250 nM or 500 nM unexpectedly resulted in eradication of colony outgrowth to the limit of detection as determined by visualization with 5× objective microscopy, whereas eradication was not observed upon treatment with either single agent Compound A or binimetinib (see arrows, FIG. 11B).

Example 17

Figure 12A:
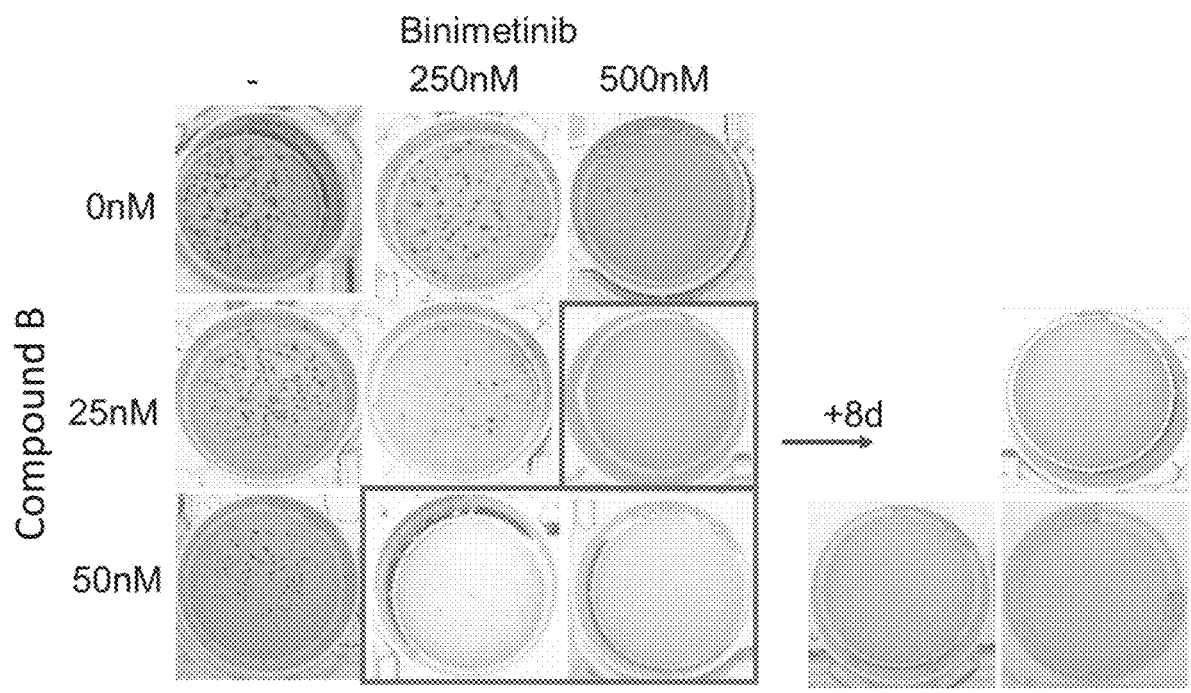
FIG. 12A shows the inhibition of colony outgrowth from treatment with single agent Compound B, single agent binimetinib, and the combination of Compound B with the MEK inhibitor binimetinib in an HMC1.2 V560G/D816V cells.

Combination Treatment with Compound B and Binimetinib Leads to Synergistic Decrease in Colony Outgrowth of HMC1.2 KIT D816V Mast Cell Line FIG. 12A is a representative picture of colony outgrowth of HMC1.2 mast cells after treatment with binimetinib (0, 250, or 500 nM), Compound B (0, 25, or 50 nM) as single agents or as a matrix combination of various concentrations of Compound B with various concentrations of binimetinib. Whereas the single agent treatment with Compound B or binimetinib resulted in colony outgrowth at all concentrations 5 days after drug removal, the combination of Compound B with binimetinib resulted in less colony outgrowth 5 days after drug removal. Combination of Compound B (25 nM) with binimetinib (250 nM) resulted in a significant decrease in outgrowth of viable HMC1.2 cells after 5 days of drug removal. Combination of Compound B (25 nM) with binimetinib (500 nM) resulted in complete eradication of outgrowth of viable HMC1.2 cells after 5 days of drug removal to the limit of detection as determined by visualization with 5× objective microscopy. Combination of Compound B (50 nM) with binimetinib (250 nM or 500 nM) unexpectedly resulted in complete eradication of outgrowth of viable HMC1.2 cells to the limit of detection as determined by visualization with 5× objective microscopy after 5 days of drug removal, whereas eradication was not observed upon treatment with single agent Compound B or single agent binimetinib. Further extension of colony outgrowth to 8 additional days (a total of 13 days) after drug removal still maintained eradication to the limit of detection of colony outgrowth with the combination of Compound B (50 nM) and binimetinib (250 or 500 nM) and Compound B (25 nM) and binimetinib (500 nM).

Figure 12B:
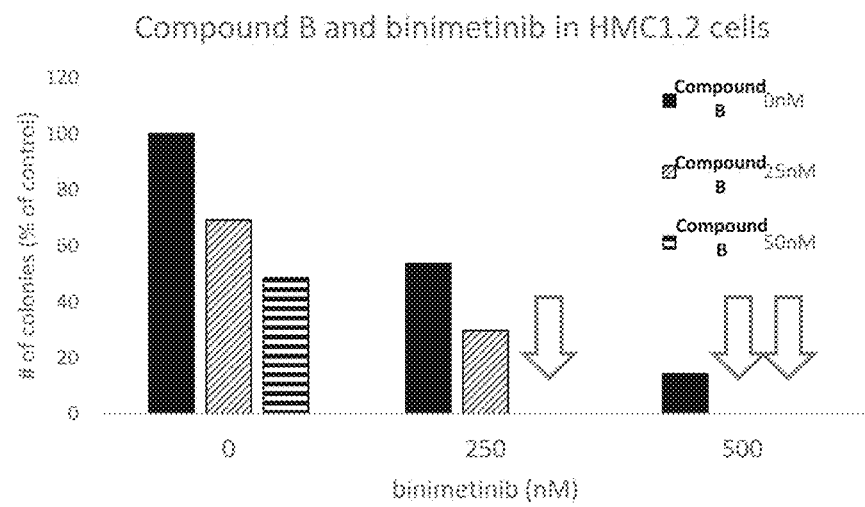
FIG. 12B shows a graphical representation of inhibition of colony outgrowth from treatment with single agent Compound B, single agent binimetinib, and the combination of Compound B with the MEK inhibitor binimetinib in HMC1.2 V560G/D816V cells. Arrows indicate no colony outgrowth.

FIG. 12B is a graphical representation quantifying colony outgrowth of HMC1.2 mast cells after the various treatments from FIG. 12A. Combination treatment with Compound B at 25 nM and binimetinib at 500 nM and combination treatment with Compound B at 50 nM and binimetinib at either 250 nM or 500 nM unexpectedly resulted in eradication of colony outgrowth to the limit of detection as determined by visualization with 5× objective microscopy, whereas eradication was not observed upon treatment with either single agent Compound B or binimetinib (see arrows, FIG. 12B).

Example 18

Figure 13A:
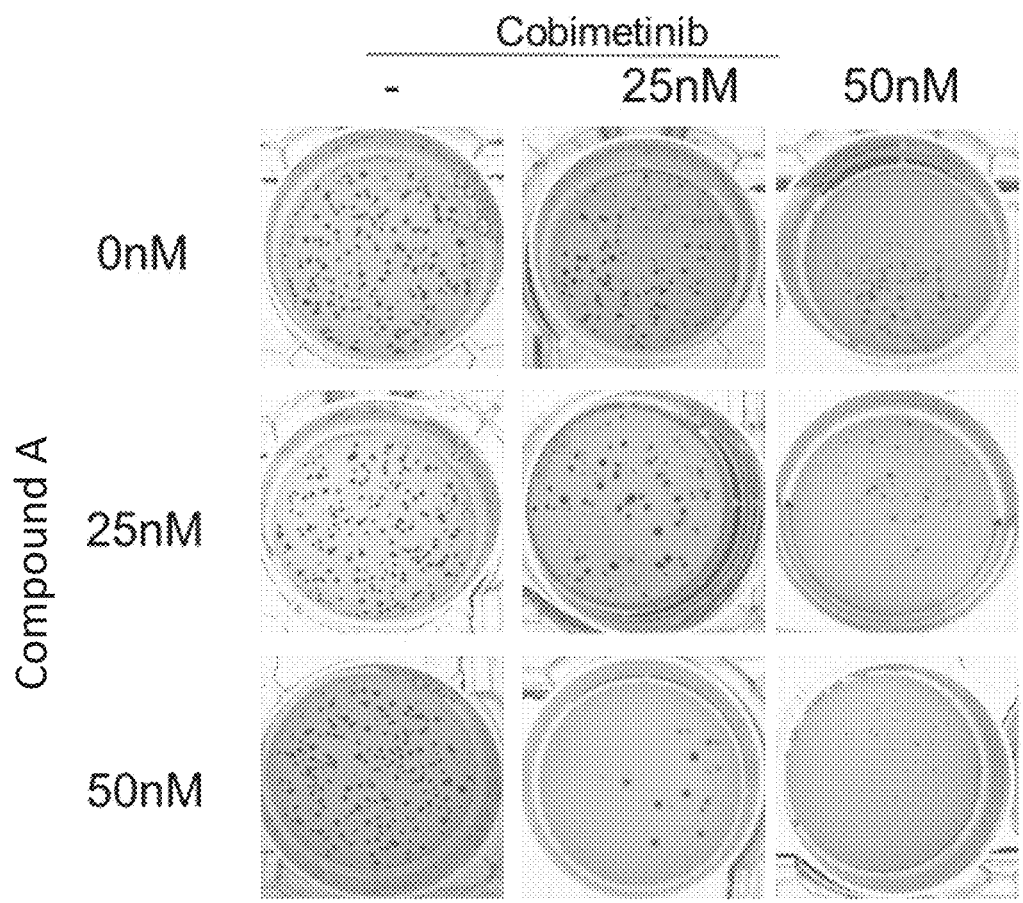
FIG. 13A shows the inhibition of colony outgrowth from treatment with single agent Compound A, single agent cobimetinib, and the combination of Compound A with the MEK inhibitor cobiimetinib in an HMC1.2 V560G/D816V cells.

Combination Treatment with Compound A and cobimetinib leads to Synergistic Decrease in Colony Outgrowth of HMC1.2 KIT D816V mast cell line FIG. 13A is a representative picture of colony outgrowth of HMC1.2 mast cells after treatment with cobimetinib (0, 25, or 50 nM), Compound A (0, 25, or 50 nM) as single agents or as a matrix combination of various concentrations of Compound A with various concentrations of cobimetinib. Whereas the single agent treatment with Compound A or cobimetinib resulted in colony outgrowth at all concentrations 5 days after drug removal, the combination of Compound A with cobimetinib resulted in less colony outgrowth 5 days after drug removal compared to either single agent treatment. Combination of Compound A (50 nM) with cobimetinib (25 or 50 nM) resulted in a significant decrease in outgrowth of viable HMC1.2 cells after 5 days of drug removal.

Figure 13B:
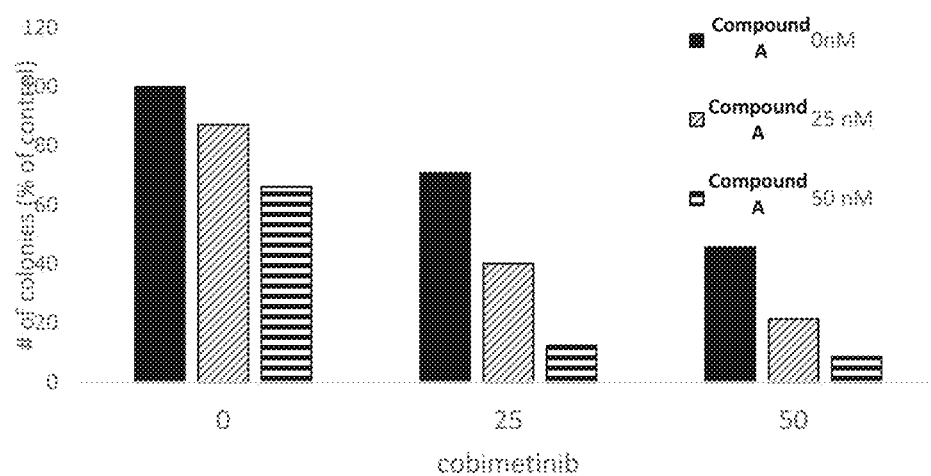
FIG. 13B shows a graphical representation of inhibition of colony outgrowth from treatment with single agent Compound A, single agent cobimetinib, and the combination of Compound A with the MEK inhibitor cobimetinib in HMC1.2 V560G/D816V cells.

FIG. 13B is a graphical representation quantifying colony outgrowth of HMC1.2 mast cells after the various treatments from FIG. 13A. Combination treatment with Compound A at 50 nM and cobimetinib at either 25 nM or 50 nM resulted in significant decrease of colony outgrowth compared to either single agent Compound A or cobimetinib.

Example 19

Figure 14A:
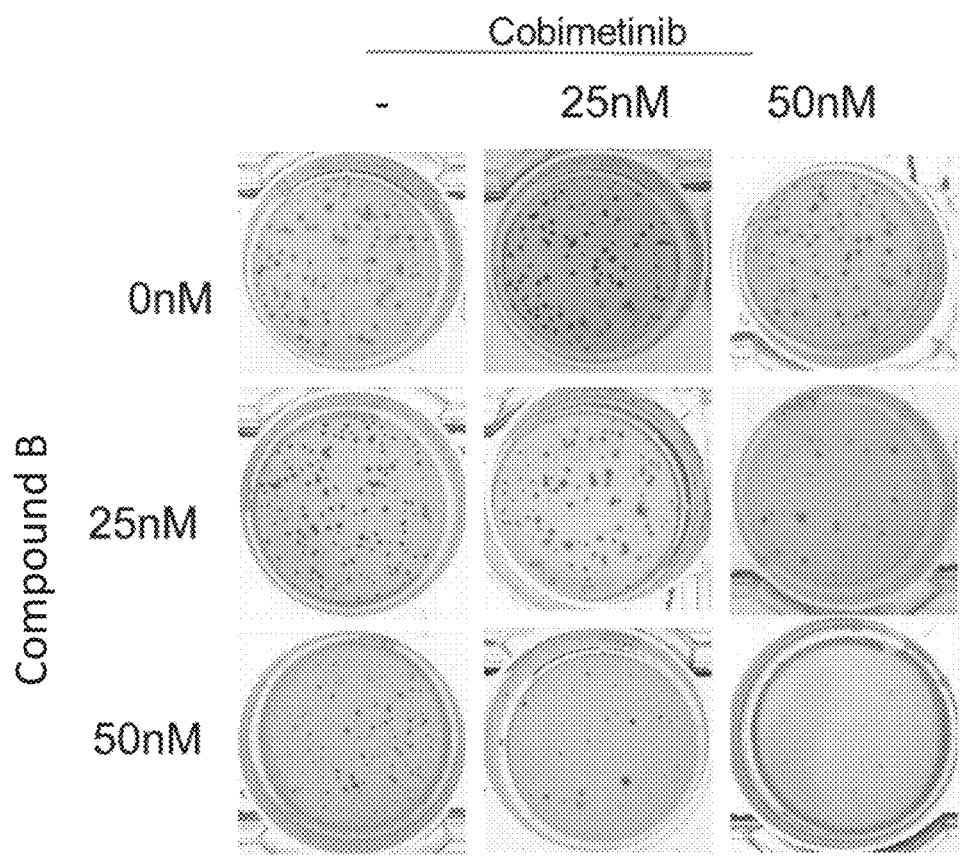
FIG. 14A shows the inhibition of colony outgrowth from treatment with single agent Compound B, single agent cobimetinib, and the combination of Compound B with the MEK inhibitor cobimetinib in an HMC1.2 V560G/D816V cells.

Combination Treatment with Compound B and Cobimetinib Leads to Synergistic Decrease in Colony Outgrowth of HMC1.2 KIT D816V Mast Cell Line FIG. 14A is a representative picture of colony outgrowth of HMC1.2 mast cells after treatment with cobimetinib (0, 25, or 50 nM), Compound B (0, 25, or 50 nM) as single agents or as a matrix combination of various concentrations of Compound B with various concentrations of cobimetinib. Whereas the single agent treatment with Compound B or cobimetinib resulted in colony outgrowth at all concentrations 5 days after drug removal, the combination of Compound B with cobimetinib resulted in less colony outgrowth 5 days after drug removal compared to either single agent treatment. Combination of Compound B (50 nM) with cobimetinib (25 or 50 nM) resulted in a significant decrease in outgrowth of viable HMC1.2 cells after 5 days of drug removal.

Figure 14B:
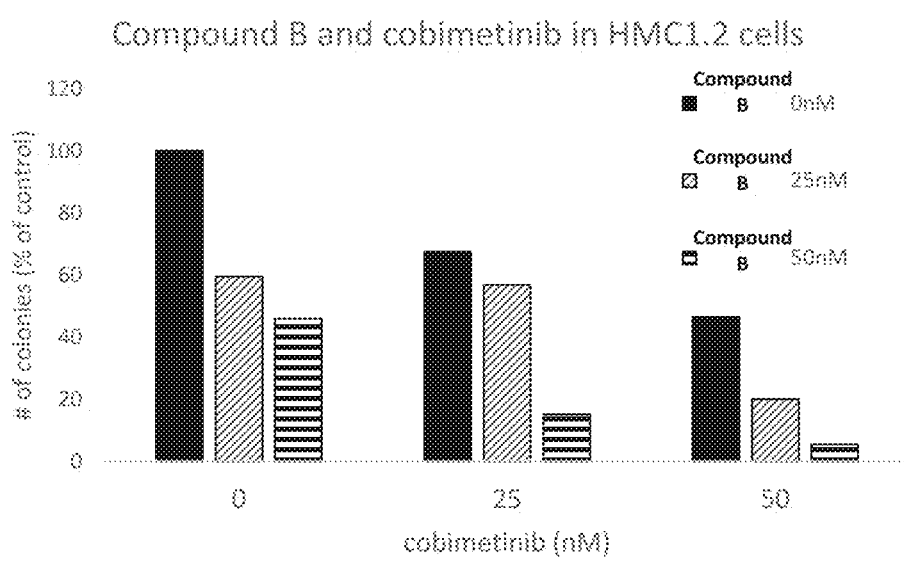
FIG. 14B shows a graphical representation of inhibition of colony outgrowth from treatment with single agent Compound B, single agent cobimetinib, and the combination of Compound B with the MEK inhibitor cobimetinib in HMC1.2 V560G/D816V cells.

FIG. 14B is a graphical representation quantifying colony outgrowth of HMC1.2 mast cells after the various treatments from FIG. 14A. Combination treatment with Compound B at 50 nM and cobimetinib at either 25 nM or 50 nM resulted in significant decrease of colony outgrowth compared to either single agent Compound B or cobimetinib.

Example 20

Combination treatment with Compound A and the ERK Inhibitor Ulixertinib Leads to a Decrease in Colony Outgrowth of HMC1.2 KIT D816V Mast Cell Line Combination treatment of Compound A and ulixertinib can be evaluated for inhibition of colony outgrowth of HMC1.2 KIT D816V mast cell line according to the method of Example 14.

Example 21

Combination Treatment with Compound B and the ERK Inhibitor Ulixertinib Leads to a Decrease in Colony Outgrowth of HMC1.2 KIT D816V Mast Cell Line Combination treatment of Compound B and ulixertinib can be evaluated for inhibition of colony outgrowth of HMC1.2 KIT D816V mast cell line according to the method of Example 14.

Example 22

Combination Treatment with Compound A and the RAF Inhibitor LY3009120 Leads to a Decrease in Colony Outgrowth of HMC1.2 KIT D816V Mast Cell Line Combination treatment of Compound A and the RAF inhibitor LY3009120 can be evaluated for inhibition of colony outgrowth of HMC1.2 KIT D816V mast cell line according to the method of Example 14.

Example 23

Combination treatment with Compound B and LY3009120 Leads to a Decrease in Colony Outgrowth of HMC1.2 KIT D816V Mast Cell Line Combination treatment of Compound B and the RAF inhibitor LY3009120 can be evaluated for inhibition of colony outgrowth of HMC1.2 KIT D816V mast cell line according to the method of Example 14.

Example 24

Combination Treatment with Compound A and the MEK Inhibitor Trametinib Induces Apoptosis in Mutant N-ras G12D Transfected HMC1.2 KIT V560G/D816V Mastocytosis Cell Line A study was performed to demonstrate that combination treatment with Compound A and trametinib induced apoptosis in mutant N-ras G12D transfected HMC1.2 V560G/D816V cells. Assays were conducted in 96 well plates with 10,000 cells seeded per well. Cells were treated with vehicle control, Compound A, trametinib, or combinations thereof at varying concentrations, and the cells were allowed to grow for 24 and 48 hours. Apoptosis was assessed by measuring caspase 3/7 activity.

Figure 15A:
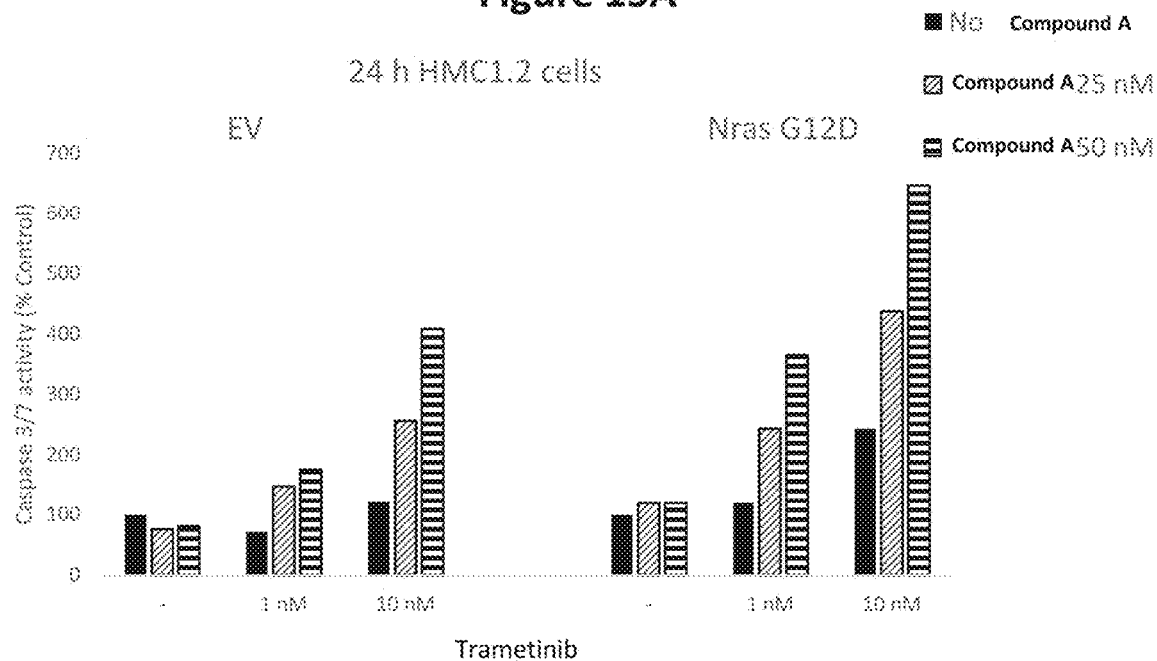
FIG. 15A shows a graphical representations of caspase activity following various treatments with Compound A and trametinib at 24 hours in empty vector (EV, left panel)) or N-ras G12D (right panel) transfected HMC1.2 V560G/D816V cells.

FIG. 15A is a graphical representation showing the relative percentage of caspase activity determined for various treatments at 24 hours. Combination treatment with Compound A and trametinib for 24 hours induced apoptosis of empty vector (EV)-transfected (left panel) HMC1.2 V560G/D816V cells or mutant N-ras G12D transfected (right panel) HMC1.2 V560G/D816V cells. Combination of Compound A with trametinib led to a synergistic increase in apoptosis in EV-transfected and in N-ras G12D transfected HMC1.2 cells.

Figure 15B:
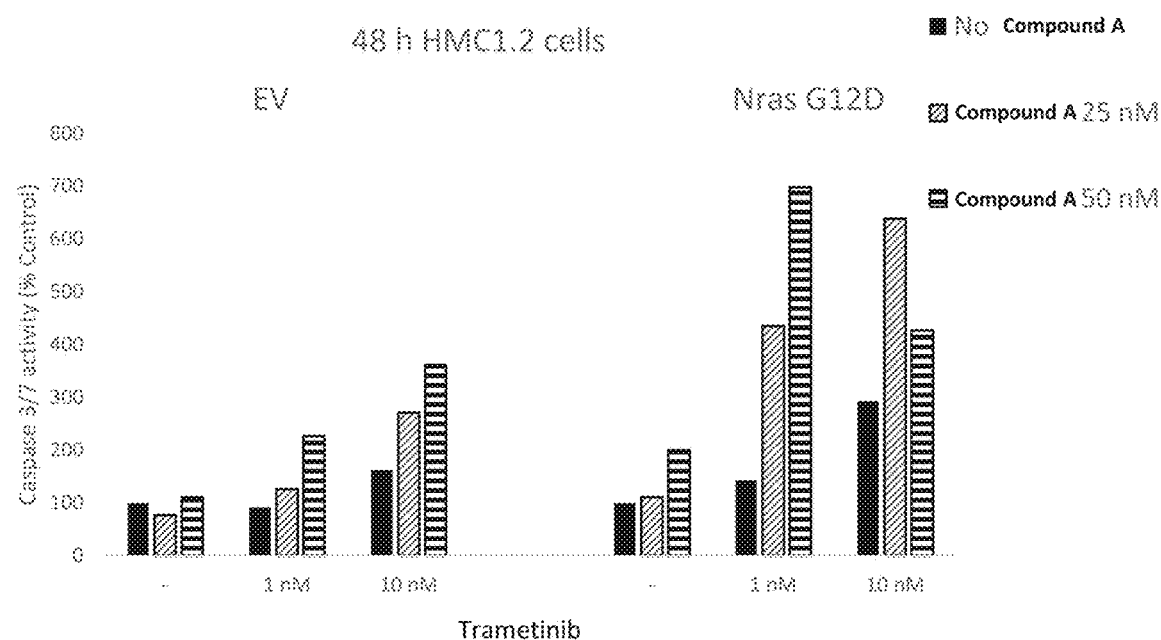
FIG. 15B shows a graphical representations of caspase activity following various treatments with Compound A and trametinib at 48 hours in empty vector (left panel) or N-ras G12D (right panel) transfected HMC1.2 V560G/D816V cells.

FIG. 15B is a graphical representation showing the relative percentage of caspase activity determined for various treatments at 48 hours. Combination treatment with Compound A and trametinib for 48 hours induced apoptosis of empty vector (EV)-transfected (left panel) HMC1.2 V560G/D816V cells or mutant N-ras G12D transfected (right panel) HMC1.2 V560G/D816V cells. Combination of Compound A with trametinib led to a synergistic increase in apoptosis in EV-transfected and in N-ras G12D transfected HMC1.2 cells. Apoptosis was higher in N-ras transfected cells than EV transfected cells.

Example 25

Figure 16A:
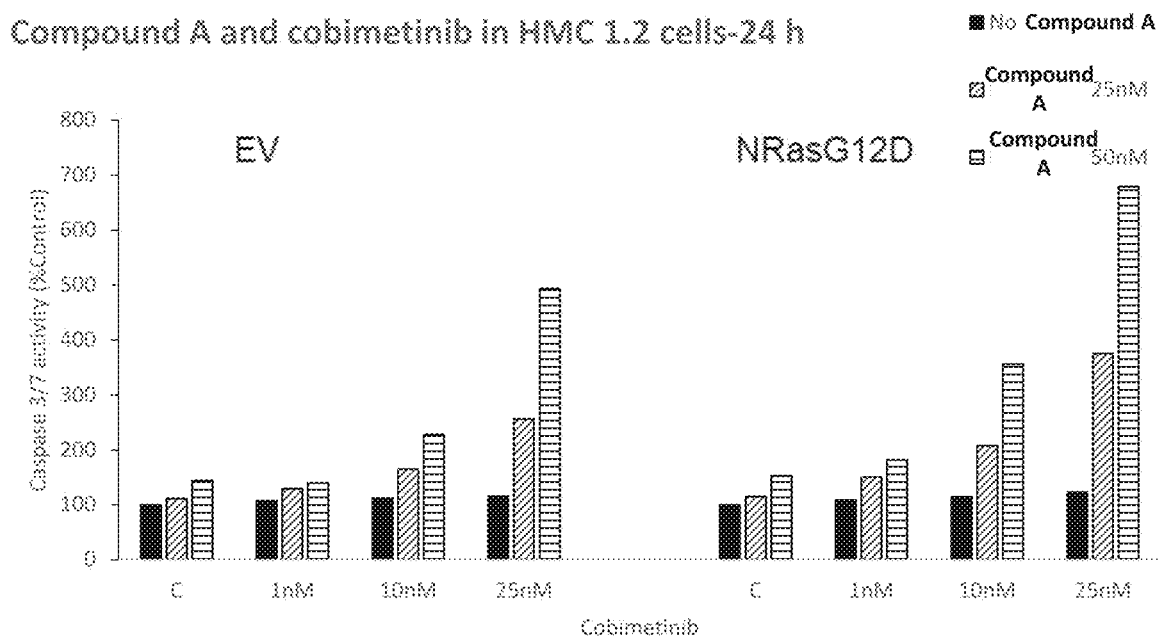
FIG. 16A shows a graphical representations of caspase activity following various treatments with Compound A and cobimetinib at 24 hours in empty vector (EV, left panel) or N-ras G12D (right panel) transfected HMC1.2 V560G/D816V cells.

Combination Treatment with Compound A and the MEK Inhibitor Cobimetinib Induces Apoptosis in Mutant N-ras G12D Transfected HMC1.2 KIT V560G/D816V Mastocytosis Cell Line FIG. 16A is a graphical representation showing the relative percentage of caspase activity determined for various treatments at 24 hours. Combination treatment with Compound A and cobimetinib for 24 hours induced apoptosis of empty vector (EV)-transfected (left panel) HMC1.2 V560G/D816V cells or mutant N-ras G12D transfected (right panel) HMC1.2 V560G/D816V cells. Combination of Compound A with cobimetinib led to a synergistic increase in apoptosis in EV-transfected and in N-ras G12D transfected HMC1.2 cells. Apoptosis was higher in N-ras transfected cells than in EV transfected cells.

Figure 16B:
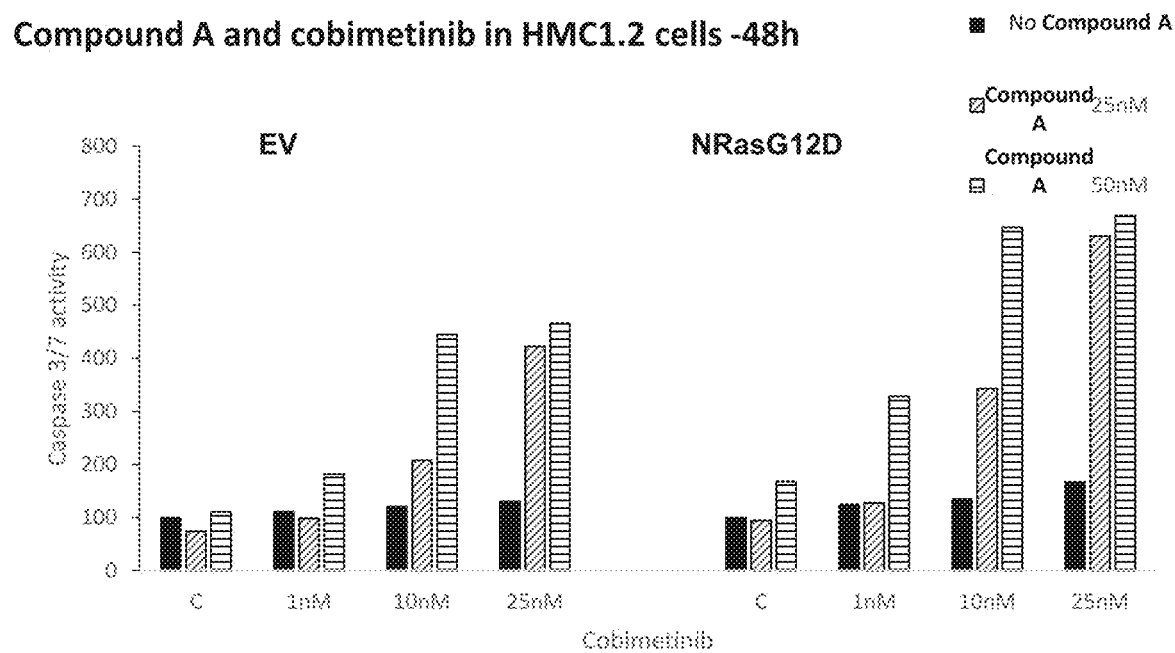
FIG. 16B shows a graphical representations of caspase activity following various treatments with Compound A and cobimetinib at 48 hours in empty vector (left panel) or N-ras G12D (right panel) transfected HMC1.2 V560G/D816V cells.

FIG. 16B is a graphical representation showing the relative percentage of caspase activity determined for various treatments at 48 hours. Combination treatment with Compound A and cobimetinib for 48 hours induced apoptosis of empty vector (EV)-transfected (left panel) HMC1.2 V560G/D816V cells or mutant N-ras G12D transfected (right panel) HMC1.2 V560G/D816V cells. Combination of Compound A with cobimetinib led to a synergistic increase in apoptosis in EV-transfected and in N-ras G12D transfected HMC1.2 cells. Apoptosis was higher in N-ras transfected cells than in EV transfected cells.

Example 26

Combination Treatment with Compound A and the MEK Inhibitor Trametinib Leads to Synergistic Decrease in Colony Outgrowth of HMC1.2 KIT D816V Mast Cell Line Transfected with N-ras G12D or Empty Vector A study was performed to demonstrate that combination treatment with Compound A and trametinib leads to decreased colony out growth of HMC1.2 transfected with empty vector (EV) or transfected with N-ras G12D, compared to treatment with either single agent. HMC1.2 cells were incubated with various concentrations of Compound A, trametinib, or a combination of Compound A and trametinib for 10 days. Drug treatments were removed and colony outgrowth of viable cells was monitored after 5 or 13 additional days.

Figure 17A:
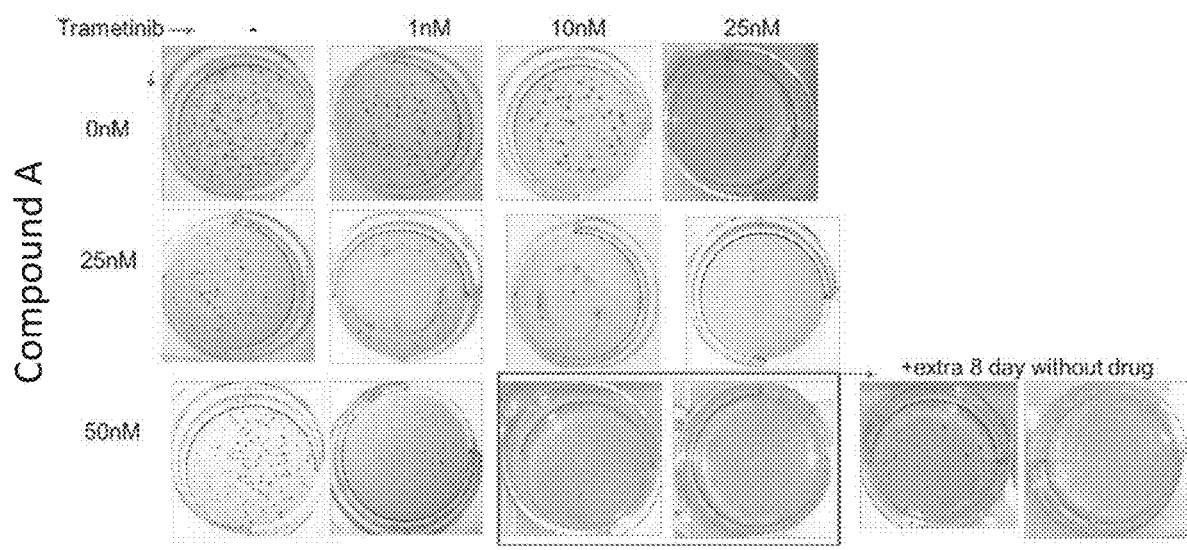
FIG. 17A shows the inhibition of colony outgrowth from treatment with single agent Compound A, single agent trametinib, and the combination of Compound A with the MEK inhibitor trametinib in an empty vector (EV) transfected HMC1.2 V560G/D816V cells.

FIG. 17A is a representative picture of colony outgrowth of EV-transfected HMC1.2 mast cells after treatment with trametinib (0, 1, 10, or 25 nM), Compound A (0, 25, or 50 nM) as single agents or as a matrix combination of various concentrations of Compound A with various concentrations of trametinib. Whereas the single agent treatment with Compound A or trametinib resulted in colony outgrowth at all concentrations 5 days after drug removal, the combination of Compound A with trametinib resulted in less colony outgrowth 5 days after drug removal. Combination of Compound A (50 nM) with trametinib (1 nM) resulted in a significant reduction in colony outgrowth in combination with 1 nM trametinib compared to single agent Compound A or single agent trametinib. Combination of Compound A (50 nM) with trametinib (10 or 25 nM) unexpectedly resulted in complete eradication of outgrowth of viable HMC1.2 cells to the limit of detection as determined by visualization with 5× objective microscopy after 5 days of drug removal, whereas eradication was not observed upon treatment with single agent Compound A or single agent trametinib. Further extension of colony outgrowth for 8 additional days after drug removal (total of 13 days after drug removal) still maintained eradication to the limit of detection of colony outgrowth with the combination of Compound A (50 nM) and trametinib (25 nM).

Figure 17B:
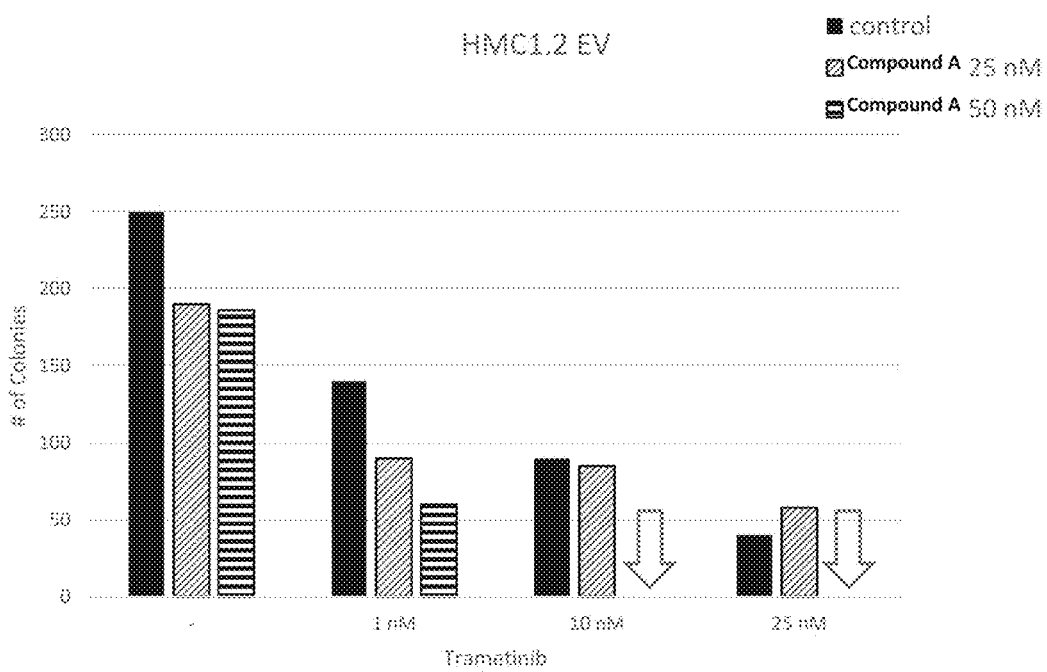
FIG. 17B shows a graphical representation of inhibition of colony outgrowth from treatment with single agent Compound A, single agent trametinib, and the combination of Compound A with the MEK inhibitor trametinib in an empty vector (EV) transfected HMC1.2 V560G/D816V cells. Arrows indicate no colony outgrowth.

FIG. 17B is a graphical representation quantifying colony outgrowth of EV-transfected HMC1.2 mast cells after the various treatments from FIG. 17A. Combination treatment with Compound A at 50 nM and trametinib at either 10 nM or 25 nM unexpectedly resulted in eradication of colony outgrowth to the limit of detection as determined by visualization with 5× objective microscopy, whereas eradication was not observed upon treatment with either single agent Compound A or trametinib (see arrows, FIG. 17B).

Figure 17C:
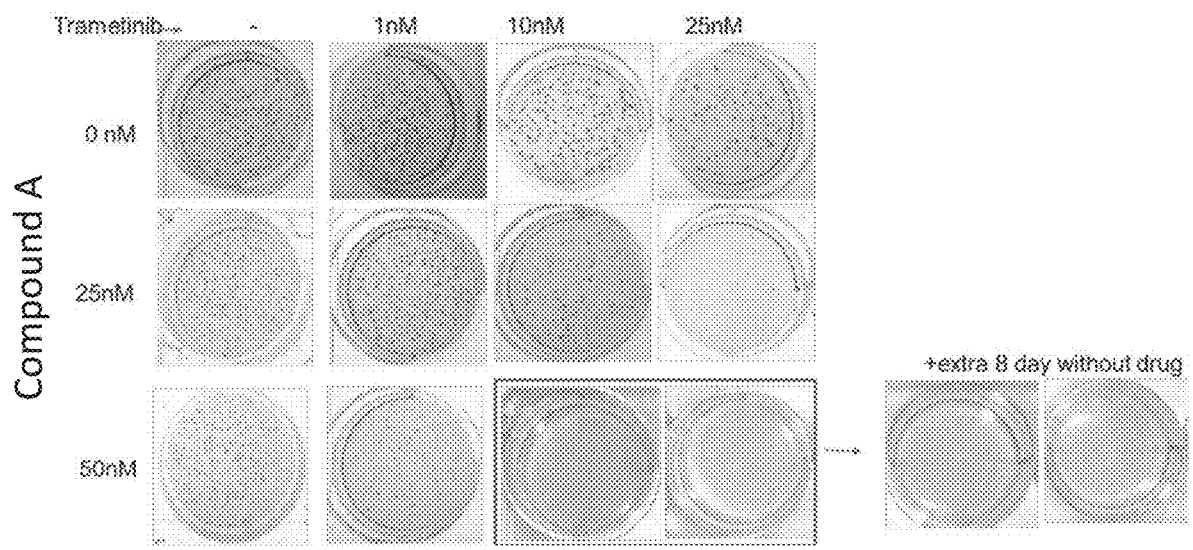
FIG. 17C shows the inhibition of colony outgrowth from treatment with single agent Compound A, single agent trametinib, and the combination of Compound A with the MEK inhibitor trametinib in an N-ras G12D transfected HMC1.2 V560G/D816V cells.

FIG. 17C is a representative picture of colony outgrowth of N-ras G12D -transfected HMC1.2 cells after treatment with trametinib (0, 1, 10, or 25 nM), Compound A (0, 25, or 50 nM) as single agents or as a matrix combination of various concentrations of Compound A with various concentrations of trametinib. Whereas the single agent treatment with Compound A or trametinb resulted in colony outgrowth at all concentrations 5 days after drug removal, the combination of Compound A with trametinib resulted in less colony outgrowth 5 days after drug removal. Combination of Compound A (25 nM) with trametinib (25 nM) resulted in a significant decrease in outgrowth of viable HMC1.2 cells after 5 days of drug removal, and combination of Compound A (50 nM) with trametinib (10 or 25 nM) unexpectedly resulted in complete eradication of outgrowth of viable N-ras G12D transfected HMC1.2 cells to the limit of detection as determined by visualization with 5× objective microscopy after 5 days of drug removal, whereas eradication was not observed upon treatment with either single agent Compound A or trametinib. Further extension of colony outgrowth by 8 additional days after drug removal (total of 13 days after drug removal) still maintained eradication of colony outgrowth with the combination of Compound A (50 nM) and trametinib (25 nM) (FIG. 17C).

Figure 17D:
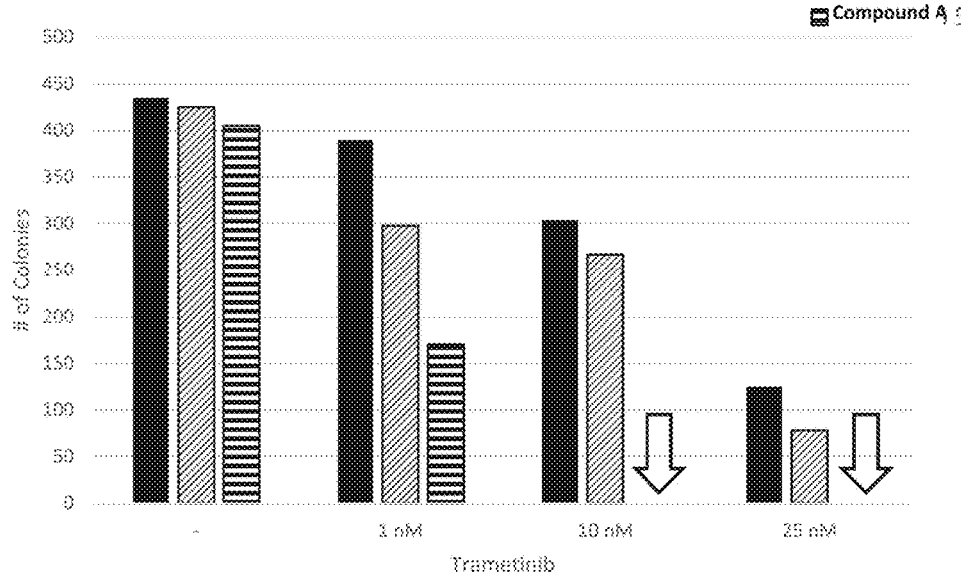
FIG. 17D shows a graphical representation of inhibition of colony outgrowth from treatment with single agent Compound A, single agent trametinib, and the combination of Compound 1 with the MEK inhibitor trametinib in an N-ras G12D transfected HMC1.2 V560G/D816V cells. Arrows indicate no colony outgrowth.

FIG. 17D is a graphical representation quantifying colony outgrowth of the various treatments from FIG. 17C. Combination treatments with Compound A and trametinib resulted in superior blockade of colony outgrowth compared to treatment with either single agent. Combination treatment with Compound A at 50 nM and trametinib at either 10 nM or 25 nM unexpectedly resulted in eradication of colony outgrowth to the limit of detection as determined by visualization with 5× objective microscopy after 5 days of drug removal, whereas eradication was not observed upon treatment with either single agent Compound A or trametinib (see arrows, FIG. 17D).

Example 27

Combination treatment with Compound A and Cobimetinib Leads to Synergistic Decrease in Colony Outgrowth of HMC1.2 KIT D816V Mast Cell Line Transfected with N-ras G12D or Empty Vector A study was performed to demonstrate that combination treatment with Compound A and cobimetinib leads to decreased colony out growth of HMC1.2 transfected with empty vector (EV) or transfected with N-ras G12D, compared to treatment with either single agent. HMC1.2 cells were incubated with various concentrations of Compound A, cobimetinib, or a combination of Compound A and cobimetinib for 10 days. Drug treatments were removed and colony outgrowth of viable cells was monitored after 5 or 10 additional days.

Figures 18A, 18B:
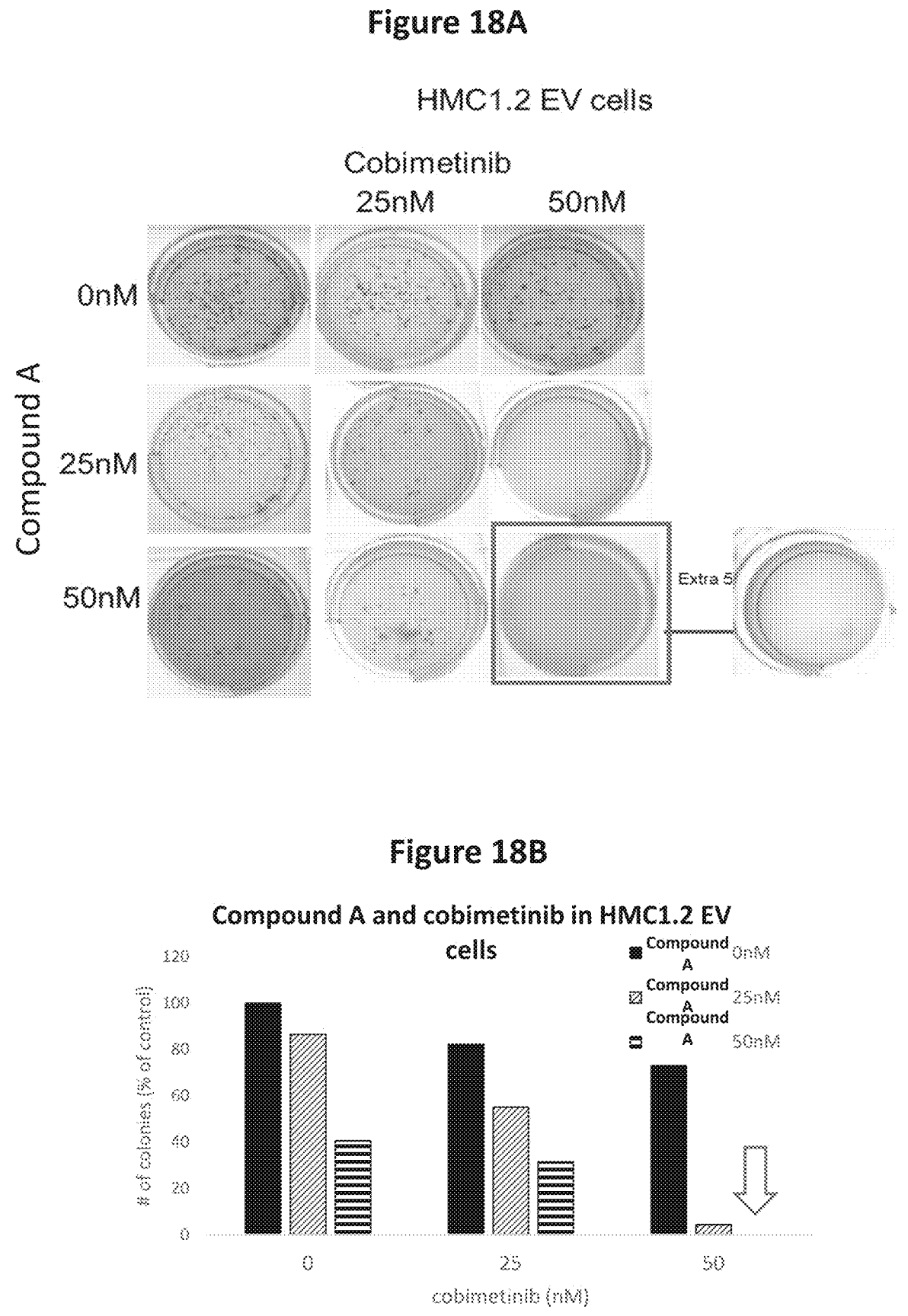

FIG. 18A is a representative picture of colony outgrowth of EV-transfected HMC1.2 mast cells after treatment with cobimetinib (25 or 50 nM), Compound A (0, 25, or 50 nM) as single agents or as a matrix combination of various concentrations of Compound A with various concentrations of cobimetinib. Whereas the single agent treatment with Compound A or cobimetinib resulted in colony outgrowth at all concentrations 5 days after drug removal, the combination of Compound A with cobimetinib resulted in less colony outgrowth 5 days after drug treatment removal. Combination of Compound A (25 nM) with cobimetinib (25 and 50 nM) resulted in a significant decrease in outgrowth of viable HMC1.2 cells after 5 days of drug treatment removal. Combination of Compound A (50 nM) with cobimetinib (50 nM) unexpectedly resulted in complete eradication of outgrowth of viable HMC1.2 cells to the limit of detection as determined by visualization with 5× objective microscopy after 5 days of drug treatment removal, whereas eradication was not observed upon treatment with single agent Compound A or single agent cobimetinib. Further extension of colony outgrowth by 5 additional days after drug treatment removal (total of 10 days after drug removal) still maintained eradication to the limit of detection of colony outgrowth with the combination of Compound A (50 nM) and cobimetinib (50 nM).

FIG. 18B is a graphical representation quantifying colony outgrowth of EV-transfected HMC1.2 mast cells after the various treatments from FIG. 18A. Combination treatment with Compound A at 50 nM and cobimetinib at 50 nM unexpectedly resulted in eradication of colony outgrowth to the limit of detection as determined by visualization with 5× objective microscopy, whereas eradication was not observed upon treatment with either single agent Compound A or cobimetinib (see arrows, FIG. 18B).

Figure 18C:
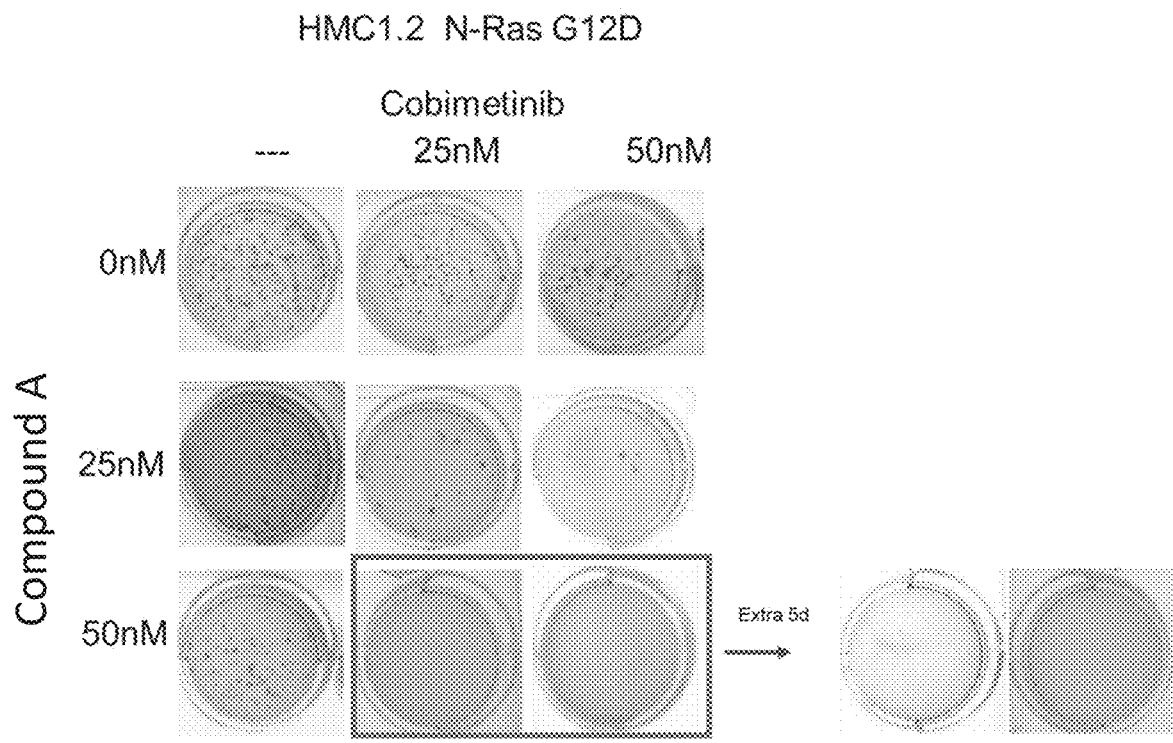
FIG. 18C shows the inhibition of colony outgrowth from treatment with single agent Compound A, single agent cobimetinib, and the combination of Compound A with the MEK inhibitor cobimetinib in an N-ras G12D transfected HMC1.2 V560G/D816V cells.

FIG. 18C is a representative picture of colony outgrowth of N-ras G12D -transfected HMC1.2 mast cells after treatment with cobimetinib (0, 25 or 50 nM), Compound A (0, 25, or 50 nM) as single agents or as a matrix combination of various concentrations of Compound A with various concentrations of cobimetinib. Whereas the single agent treatment with Compound A or cobimetinib resulted in colony outgrowth at all concentrations 5 days after drug treatment removal, the combination of Compound A with cobimetinib resulted in less colony outgrowth 5 days after drug treatment removal. Combination of Compound A (25 nM) with cobimetinib (25 and 50 nM) resulted in a significant decrease in outgrowth of viable HMC1.2 cells after 5 days of drug removal. Combination of Compound A (50 nM) with cobimetinib (25 or 50 nM) unexpectedly resulted in complete eradication of outgrowth of viable HMC1.2 cells to the limit of detection as determined by visualization with 5× objective microscopy after 5 days of drug treatment removal, whereas eradication was not observed upon treatment with single agent Compound A or single agent cobimetinib. Further extension of colony outgrowth to 10 additional days after drug treatment removal still maintained eradication to the limit of detection of colony outgrowth with the combination of Compound A (50 nM) and cobimetinib (25 or 50 nM).

Figure 18D:
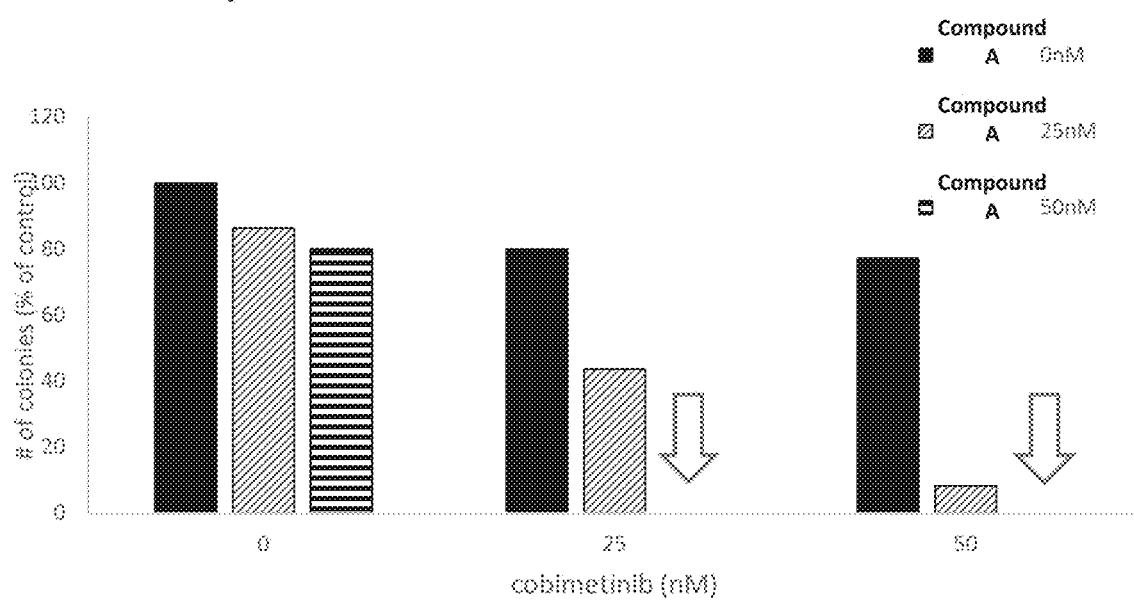
FIG. 18D shows a graphical representation of inhibition of colony outgrowth from treatment with single agent Compound A, single agent cobimetinib, and the combination of Compound A with the MEK inhibitor cobimetinib in an N-ras G12D transfected HMC1.2 V560G/D816V cells. Arrows indicate no colony outgrowth.

FIG. 18D is a graphical representation quantifying colony outgrowth of the various treatments from FIG. 18C. Combination treatments with Compound A and cobimetinib resulted in superior blockade of colony outgrowth compared to treatment with either single agent. Combination treatment with Compound A at 50 nM and cobimetinib at 25 or 50 nM unexpectedly resulted in eradication of colony outgrowth to the limit of detection as determined by visualization with 5× objective microscopy after 5 days of drug removal, whereas eradication was not observed upon treatment with either single agent Compound A or cobimetinib (see arrows, FIG. 18D).

Equivalents

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed is:

1. A method of treating mastocytosis in a patient in need thereof, comprising administering to the patient:
an effective amount of a c-KIT inhibitor, wherein the c-KIT inhibitor is 1-[4-bromo-5-[1- ethyl-7-(methylamino)-2-oxo-1,2-dihydro-1,6-naphthyridin-3-yl]-2-fluorophenyl]-3-phenylurea, or a pharmaceutically acceptable salt thereof; and
an effective amount of one or more MAPKAP pathway inhibitors selected from the group consisting of trametinib, cobimetinib, binimetinib, and ulixertinib.

2. The method of claim 1, wherein the mastocytosis has a c-KIT mutation.

3. The method of claim 2, wherein the c-KIT mutation is an activating mutation.

4. The method of claim 1, wherein the mastocytosis comprises mast cells having a primary mutation in exon 17 of a c-KIT gene.

5. The method of claim 4, wherein the primary mutation is one of D816V, D816Y, D816F, D816H, F522C, K509I, V560G, V559G, and del419.

6. The method of claim 1, wherein the mastocytosis is systemic mastocytosis.

7. The method of claim 6, wherein the systemic mastocytosis is selected from the group consisting of indolent systemic mastocytosis, systemic smoldering mastocytosis, systemic mastocytosis with associated clonal hematological non-mast cell lineage disease, aggressive systemic mastocytosis, mast cell leukemia, and mast cell sarcoma.

8. The method of claim 1, wherein the mastocytosis is cutaneous mastocytosis.

9. The method of claim 8, wherein the mastocytosis is selected from the group consisting of: maculopapular cutaneous mastocytosis, mastocytoma, and diffuse cutaneous mastocytosis.

10. The method of claim 1, wherein the c-KIT inhibitor and the MAPKAP pathway inhibitor are administered substantially concurrently or sequentially.

11. The method of claim 1, further comprising administering another cancer-targeted therapeutic agent, cancer-targeted biological, immune checkpoint inhibitor, or chemotherapeutic agent.

12. A method of treating a systemic mastocytosis in a patient in need thereof, comprising administering to the patient:
an effective amount of 1-[4-bromo-5-[1-ethyl-7-(methylamino)-2-oxo-1,2-dihydro-1,6-naphthyridin-3-yl]-2-fluorophenyl]-3-phenylurea, or a pharmaceutically acceptable salt thereof;
and an effective amount of one or more MAPKAP pathway inhibitors selected from the group consisting of trametinib, cobimetinib, binimetinib, and ulixertinib, SCH772984, LY3214996, LY3009120, vemurafenib, and dabrafenib.

* * * * *